United States Patent [19]
Kriegler et al.

[11] Patent Number: 5,874,077
[45] Date of Patent: Feb. 23, 1999

[54] HUMAN TIL CELLS EXPRESSING RECOMBINANT TNF PROHORMONE

[75] Inventors: Michael Kriegler, San Francisco; Carl F. Perez, Berkeley, both of Calif.

[73] Assignee: Chiron Corporation, Emeryville, Calif.

[21] Appl. No.: 448,889

[22] Filed: May 24, 1995

Related U.S. Application Data

[60] Continuation of Ser. No. 237,783, Jun. 6, 1994, which is a division of Ser. No. 839,017, Feb. 18, 1992, Pat. No. 5,324,655, which is a continuation of Ser. No. 488,706, Mar. 2, 1990, abandoned, which is a continuation-in-part of Ser. No. 474,169, Feb. 2, 1990, abandoned, which is a continuation-in-part of Ser. No. 426,986, Oct. 24, 1989, abandoned.

[51] Int. Cl.⁶ .............................. A61K 45/05; C12N 5/22
[52] U.S. Cl. .................................. 424/93.21; 435/372.3; 435/69.7
[58] Field of Search .................... 530/351, 395; 430/144; 435/372.3, 69.7; 424/93.21; 514/44

[56] References Cited

U.S. PATENT DOCUMENTS

| | | |
|---|---|---|
| 4,405,712 | 9/1983 | Vande Woude et al. . |
| 4,518,584 | 5/1985 | Mark et al. . |
| 4,603,112 | 7/1986 | Paoletti et al. . |
| 4,650,764 | 3/1987 | Temin et al. . |
| 4,663,281 | 5/1987 | Gillies et al. . |
| 4,677,063 | 6/1987 | Mark et al. . |
| 4,677,064 | 6/1987 | Mark et al. ............................. 435/69.1 |
| 4,678,751 | 7/1987 | Goeddel . |
| 4,708,818 | 11/1987 | Montanier et al. . |
| 4,725,669 | 2/1988 | Essex et al. . |
| 4,738,922 | 4/1988 | Haseltine et al. . |
| 4,752,565 | 6/1988 | Folks et al. . |
| 4,769,330 | 9/1988 | Paoletti et al. . |
| 4,822,605 | 4/1989 | Powell . |
| 4,847,201 | 7/1989 | Kaswasaki et al. . |
| 4,861,719 | 8/1989 | Miller . |
| 4,868,116 | 9/1989 | Morgan et al. . |
| 4,868,119 | 9/1989 | Clark et al. . |
| 4,873,316 | 10/1989 | Meade et al. . |
| 4,879,226 | 11/1989 | Wallace et al. ........................ 435/68.1 |
| 4,894,439 | 1/1990 | Dorin et al. . |
| 4,980,286 | 12/1990 | Morgan et al. . |
| 4,980,289 | 12/1990 | Temin et al. . |
| 4,990,455 | 2/1991 | Yamagishi et al. . |
| 5,028,420 | 7/1991 | Masegi et al. . |
| 5,081,021 | 1/1992 | Mizuno et al. . |
| 5,091,309 | 2/1992 | Schesinger et al. . |
| 5,126,132 | 6/1992 | Rosenberg ............................. 424/85.2 |
| 5,206,352 | 4/1993 | Robinson et al. . |
| 5,246,924 | 9/1993 | Fox et al. . |
| 5,262,309 | 11/1993 | Nakamura et al. . |
| 5,288,852 | 2/1994 | Yamada et al. . |
| 5,304,489 | 4/1994 | Rosen . |
| 5,306,631 | 4/1994 | Harrison et al. . |
| 5,324,655 | 6/1994 | Kriegler et al. . |
| 5,399,346 | 3/1995 | Anderson et al. . |
| 5,487,984 | 1/1996 | Allet et al. . |
| 5,652,130 | 7/1997 | Kriegler et al. ...................... 435/172.3 |

FOREIGN PATENT DOCUMENTS

B-19201/88  1/1989  Australia .
0 092 182 A2  10/1983  European Pat. Off. .

(List continued on next page.)

OTHER PUBLICATIONS

Adam, et al., "Identification of a Signal in a Murine Retrovirus That is Sufficient for Packaging of Nonretroviral RNA into Virions," *J. Virology*, 62(10):3802–3806 (Oct., 1988).
Baltimore, Intracellular Immunization, *Nature*, 335:395–396 (1988).

(List continued on next page.)

*Primary Examiner*—David L. Fitzgerald
*Attorney, Agent, or Firm*—Donald Pochopien; Norman J. Kruse; Robert P. Blackburn

[57] ABSTRACT

Tumor Infiltrating Lymphocyte (TIL) cells transformed with exogenous DNA encoding tumor necrosis factor (TNF) prohormone variants are disclosed. Among such variants are the TNF γ sig construct, which facilitates expression of the mature TNF polypeptide, and the noncleavable cytotoxic prohormone variants TNFΔ(1→12) and TNF(1+12). The transformed TIL cells are useful in antitumor therapy.

14 Claims, 12 Drawing Sheets

FOREIGN PATENT DOCUMENTS

| | | |
|---|---|---|
| 0 178 220 A2 | 4/1986 | European Pat. Off. . |
| 0 196 864 A2 | 10/1986 | European Pat. Off. . |
| 0 237 676 A2 | 9/1987 | European Pat. Off. . |
| 0 243 204 A2 | 10/1987 | European Pat. Off. . |
| 0 245 136 A1 | 11/1987 | European Pat. Off. . |
| 0 273 782 A1 | 7/1988 | European Pat. Off. . |
| 0 293 181 A1 | 11/1988 | European Pat. Off. . |
| 0 317 649 A1 | 5/1989 | European Pat. Off. . |
| 0 288 163 A2 | 9/1989 | European Pat. Off. . |
| 0 334 301 A1 | 9/1989 | European Pat. Off. . |
| WO91/06658 | 5/1991 | European Pat. Off. . |
| 2 559 159 | 2/1984 | France . |
| 2 606 030 | 10/1986 | France . |
| 63-32486 | 2/1988 | Japan . |
| WO 85/05619 A | 12/1985 | WIPO . |
| WO 86/00922 | 2/1986 | WIPO . |
| WO 86/00930 | 2/1986 | WIPO . |
| WO 89/01972 | 3/1989 | WIPO . |
| WO 89/01973 | 3/1989 | WIPO . |
| WO 89/02468 | 3/1989 | WIPO . |
| WO 89/05345 | 6/1989 | WIPO . |
| WO 89/05349 | 6/1989 | WIPO . |
| WO 89/07150 | 8/1989 | WIPO . |
| WO 89/09271 | 10/1989 | WIPO . |

OTHER PUBLICATIONS

Bartram et al., "Translocation of c–abl Oncogene Correlates with the Presence of a Philadelphia Chromosome in Chronic Myelocyutic Leukaemia," *Nature*, 306:277–280 (1983).

Bastin, et al., "Use of Syntehtic Peptides of Influenza Nucleoprotein to Define Epitopes Recognized by Class I–Restricted Cytotoxic T Lymphocytes," *Journal of Experimental Medicine*, 150:1508–1523 (1987).

Bishop, J.M. "Cancer Genes Come Of Age," *Cell*, 32:1018–1020 (Apr., 1983).

Bjorkman, et al., "The foreign antigen binding site and T cell recognition regions of class I histocompatibility antigens," *Nature*, 329:512–518 (1987).

Braciale, et al., "Role of Viral Infectivity in the Induction of Influenza Virus–Specific Cytotoxic T Cells," *Journal of Experimental Medicine*, pp. 1236–1252 (1977).

Calabretta et al., "Altered expression of $G_1$–specific genes in human malignant myeloid cells," *Proc. Natl. Acad. Sci USA*, 83:1495–1498 (Mar., 1986).

Cepko, et al., "Construction and Applications of a Highly Transmissible Murine Retrovirus Shuttle Vector," *Cell*, 37:1053–1062 (Jul., 1984).

Cone, et al., "Regulated Expression of a Complete Human β–Globin Gene Encoded by a Transmissible Retrovirus Vector," *Mol. & Cell. Biol.*, 7(2):887–897 (Feb., 1987).

Danos, et al., "Safe and Efficient Generation of Recombinant Retroviruses With Amphotropic and Ecotropic Host Ranges," *Proc. Nat'l Acad. Sci., USA*, 85:6460–6464 (Sep., 1988).

Davis et al., "Expression of hepatitis B surface antigen with a recombinant adenovirus," *Proc. Natl. Acad. Sci., USA*, 82:7560–7564 (Nov., 1985).

Dayton, et al., "The Trans–Activator Gene of the Human T Cell Lymphotropic Virus Type III is Required for Replication," *Cell*, 44:941–947 (Mar. 28, 1986).

DeVries et al., "Interplay between the TCR/CD3 Complex and CD4 or CD8 in the Activation of Cytotoxic T Lymphocytes," *Immunological Reviews*, 109:119–141 (1989).

Dewar, et al., "Synthesis and Processing of Human Immunodeficiency Virus Type 1 Envelope Proteins Encoded by a Recombinant Human Adenovirus," *Journal of Virology*, 63:129–136 (1989).

Dzierzak et al., "Lineage–Specific Expression of a Human β–Globin Gene In Murine Bone Marrow Transplant Recipients Reconstituted With Retrovirus–Transduced Stem Cells," *Nature*, 331:35–41 (Jan. 7, 1988).

Felber, et al., "A Quantitative Bioassay for HIV–1 Based on Trans–Activation," *Science*, 239:184–187 (Jan. 8, 1988).

Felgner et al., "Lipofection: A Highly Efficient, Lipid–Mediated DNA–Transfection Procedure," *Proc. Nat'l Acad. Sci., USA*, 84:7413–7417 (Nov., 1987).

Frankel, et al., "Dimerization of the Tat Protein from Human Immunodeficiency Virus: A Cysteine–Rich Peptide Mimics the Normal Metal–Linked Dimer Interface," *Proc. Nat'l Acad. Sci., USA*, 85:6297–6300 (Sep., 1988).

Frankel, et al., "Tat Protein From Human Immunodeficiency Virus Forms a Metal–Linked Dimer," *Science*, 240:70–73 (Apr., 1988).

Friedman, et al., "Expression of a Truncated Viral Trans–Activator Selectively Impedes Lytic Infection by Its Cognate Virus," *Nature*, 335:452–454 (Sep. 29, 1988).

Furman, et al., Inhibition of Herpes Simplex Virus–Induced DNA Polymerase Activitiy and Vital DNA Replication by 9–(2–Hydroxyethoxymethyl)guanine and Its Triphosphate,: *J. Virology*, 32(1):72–77 (Oct., 1979).

Ganz, et al., "Defensins Natural Peptide Antibiotics of Human Neutrophils," *J. Clin, Invest.*, 76:1427–1435 (Oct., 1985).

Gilboa, et al., "Transfer and Expression of Cloned Genes Using Retroviral Vectors," *BioTechniques*, 4(6):504–512 (1986).

Goelz, S.E., "Hypomethylation of DNA from Benign and Malignant Human Colon Neoplasms," *Science*, 228:187–190 (Apr. 12, 1985).

Guild, et al., "Development of Retrovirus Vectors Useful for Expressing Genes in Cultured Murine Embryonal Cells and Hematopoietic Cells In Vivo," *J. Virol.*, 62(10):3795–3801 (1988).

Haj–Ahmad et al., "Development of a Helper–Independent Human Adenovirus Vector and Its Use in the Transfer of the Herpes Simplex Virus Thymidine Kinase Gene," *Journal of Virology*, 57(1)267–274 (Jan. 1986).

Hellström and Hellström , "Cellular Immunity Against Tumor Antigens," *Adv. Cancer Res.* 12:167–223 (1969).

Hellström and Hellström , "Oncogene–associated Tumor Antigens as targets for Immunotherapy," *FASEB J.*, 3:1715–1722 (1989).

Hickling, et al., Varicella–Zoster Virus–Specific Cytotoxic T Lymphocytes (TC): Detection and Frequency Analysis of HLA Class I–Restricted Tc in Human Peripheral Blood, *Journal of Virology*, 61:3463–3469 (1987).

Hirochika et al., "Functional mapping of the human papillomavirus type II transcriptional enhancer and its interaction with the trans–acting E2 proteins," *Genes & Development*, 2:54–67 (1988).

Hirsch, M.S., "Aids Commentary: Azidothymidine," *J. Infect. Dis.*, 157(3):427–431 (1988).

Ho et al., "A T–Cell–Specific Transcriptional Enhancer Element 3' of $C_\alpha$ in the Human T–Cell Receptor a Locus," *Proc. Nat'l Acad. Sci., USA*, 86:6714–6718 (Sep., 1989).

Hoffenbach, et al., "Unusually High Frequencies of HIV–Specific Cytotoxic T Lymphocytes in Humans," *Journal of Virology*, 142:452–462 (1989).

Hwang et al., "Expression of Genes Introduced into Cells by Retroviral Infection Is More Efficient Than That of Genes Introduced into Cells by DNA Transfection," *Journal of Virology*, 50(2):417–424 (May 1984).

Johnston, et al., "Genetic evidence that zinc is an essential co–factor in the DNA binding domain of GAL4 protein," *Nature*, 328:353–355 (Jul., 1987).

Jolly, et al., "Variable Stability of a Selectable Provirus After Retroviral Vector Gene Transfer Into Human Cells," *Molecular and Cellular Biology*, 6(4):1141–1147 (Apr., 1986).

Jolly, et al., "High–Efficiency Gene Transfer into Cells," *Methods in Enzymology*, 149:10–25, (1987).

Joyner, et al., "Construction and Transfer of Recombinant Retrovirus Clones Carrying the HSV–1 Thymidine Kinase Gene," Development Biology Using Purified Genes, Academic Press 1981.

Kantoff, et al., "Correction of Adenosine Dearninase Deficiency in Cultured Human T and B Cells by Retrovirus–mediated Gene Transfer," *Proc. Nat'l Acad. Sci. USA*, 83:6563–6567 (Sep., 1986).

Klein, G., "Tumor Antigens," *Ann. Rev. Microbiol.*, 20:223–252 (1966).

Kwon et al., "Sequence Analysis of Mouse Tyrosinase cDNA and the Effect of Melanotropin on its Gene Expression," *Biochemical and Biophysical Research Communications*, 153(3):1301–1309 (Jun. 30, 1988).

Ledley, Fred D., "Somatic gene therapy for human disease: Background and prospects. Part II," *The Journal of Pediatrics*, 110(2):167–174.

Lundwall et al., "Molecular cloning of human prostate specific antigen cDNA," *FEBS Letters*, 214(2):317–322 (Apr. 1987).

Lundwall, Ake, "Characterization of the gene for Prostate–specific antigen, a human glandular kallikrein," *Biochemical and Biophysical Research Communications*, 161(3):1151–1159 (Jun. 30, 1989).

Malim, et al., "The HIV–1 rev trans–activator Acts Through a Structured Target Sequence to Activate Nuclear Export of Unspliced Vital mRNA," *Nature*, 338:254–257 (1989).

Maniatis, et al., "Regulation of Inducible and Tissue–Specific Gene Expression," *Science*, 236:1237–1245 (Jun. 5, 1987).

Maniatis, et al., *Molecular Cloning: A Laboratory Manual*, Cold Spring Harbor Laboratory, Cold Spring Harbor Press, pp. 22–26 (1982).

Mariman, E.C.M., "New Strategies for AIDS therapy and Prophylaxis," *Nature*, 318:414 (1985).

McCormick, D., "Human Gene Therapy: The First Round," *BioTechnology*, 3(8):689–693 (1985).

Miller, et al., "Treatment of B–Cell Lymphoma With Monoclonal Anti–Idiotype Antibody," *New England J. Med.*, 386:517–522, (1982).

Mitsuya, et al., Strategies for Antiviral Therapy in AIDS, *Nature*, 325:773–778 (Feb. 26, 1987).

Monsour, et al., "Disruption of the Proto–Oncogene int–2 In Mouse Embryo–Derived Stem Cells: A General Strategy for Targeting Mutations to Non–Selectable Genes," *Nature*, 336:348–352 (Nov., 1988).

Moolten, F.L., An Alternative to the Magic Bullet Paradigm for Specific Cancer Therapy,: *Medical Hypotheses*, 24:43–51 (1987).

Morin et al., "Recombinant adenovirus induces antibody response to hepatitis B virus surface antigen in hamsters," *Proc. Natl. Acad. Sci., USA* 84:4626–4630 (Jul., 1987).

Muesing, et al., Regulation of mRNA Accumulation by a Human Immunodeficiency Virus Trans–Activator Protein,: *Cell*, 48:691–701 (1987).

Nabel, et al., "Alternative Mechanisms for Activation of Human Immunodeficiency Virus Enhancer in T Cells," *Science*, 239:1299–1302 (1988).

Nelson, et al., "Gene replacement therapy for inborn errors of purine metabolism," Cold Spring Harbor Symp. Quant. Biol., 51(2):1065–1071 (1986).

Orme, Ian M., "The Kinetics of Emergence and Loss of Mediator T Lymphocytes Acquired in Response to Infection With *Mycobacterium Tuberculosis*,"*Journal of Immunology*, 138:293–298 (Jan. 1, 1987).

Overhauser, et al., "Generation of Glucocorticoid–Responsive Moloney Murine Leukemia Virus by Insertion of Regulatory Sequences from Murine Mammary Tumor Virus into the Long Terminal Repeat," *J. Virol.*, 54(1):133–144 (1985).

Palmer et al., "Efficient retrovirus–mediated transfer and expression of a human adenosine deaminase gene in diploid skin fibroblasts from an adenosine deaminase–deficient human," *Proc. Natl. Acad. Sci. USA*, 84:1055–1059 (Feb. 1987).

Palmiter, et al., "Cell Lineage Ablation In Transgenic Mice By Cell–Specific Expression of A Toxin Gene," *Cell*, 80:435–443 (1987).

Patarca, et al., rpt–1, An Intracellular Protein From Helper/Inducer T Cells That Regulates Gene Expression of Interleukin 2 Receptor and human Immunodeficiency Virus Type 1,: *Proc. Nat'l Acad. Sci.*, 85:2733–2737 (1988).

Peterlin, et al., Elevated Levels of mRNA Can Account for the Trans–Activation of Human Immunodeficiency Virus,: *Proc. Nat'l Acad. Sci., USA*, 83:9734–9738 (Dec., 1986).

Phelps, et al., "The Human Papillomavirus Type 16 E7 Gene Encodes Transactivation and Transformation Functions Similar to Those of Adenovirus EIA," *Cell*, 53:539–547 (May 20, 1988).

Piatak, et al., "Expression of Soluble and Fully Functional Ricin A Chain in *Escherichia coli* is Temperature–Sensitive," *J. Biol. Chem.*, 263(10):4837–4843 (Apr., 5, 1988).

Pizer, et al., "A Mammalian Cell Line Designed to Test the Mutagenic Activity of Anti–Herpes Nucleosides," *Int. J. Cancer*, 40:114–121 (1987).

Reddehase, et al., "CD8–Positive T Lymphocytes Specific for Murine Cytomegalovirus Immediate–Early Antigens Mediate Protective Immunity," *Journal of Virology*, 61(10):3102–3108 (1987).

Riegman et al., "Molecular Cloning and Characterization of Novel Prostate Antigen cDNA's," *Biochemical and Biophysical Research Communications*, 155(1):181–188 (Aug. 30, 1988).

Roman, et al., "Immunoselection of Stably Transformed MDCK Cells Expressing the Vesicular Stomatitis Virus G–Protein at the Basolateral Surface," *Experimental Cell Research*, 175:376–387 (1988).

Ruppert et al., "Multiple transcripts of the mouse tyrosinase gene are generated by alternative splicing," *The EMBO Journal*, 7(9):2715–2722 (1988).

Satoshi, et al., "Construction of plasmids for recombinanat manufacture and extracellular secretion of tumor necrosis factor (TNF) or its muteins," *Chemical Abstracts*, 111:168668 (1989).

Sawyer et al., "Mapping of the Varicella Zoster Virus Deoxypyrimidine Kinase Gene and Preliminary Identification of its Transcript," *Virology*, 149:1–9 (1986).

Schulz et al., "Sequence of cDNA clone encompassing the complete mature human Prostate Specific Antigen (PSA) and an unspliced leader sequence," *Nucleic Acids Research*, 16(13):6226 (1988).

Selsted, et al., "Primary Structures of Three Human Neutrophil Defensins," *J. Clin. Invest.*, 76:1436–1439 (Oct., 1985).

Shibahara et al., "Cloning and expression of cDNA encoding mouse tyrosinase," *Nucleic Acids Research*, 14(6):2413–2427 (1986).

Shinnick, et al., "Nucleotide Sequence of Moloney Murine Leukaemia Virus," *Nature*, 293:543–548 (1981).

Short, et al., "Characterization of the phosphoenolpyruvate carboxykinase (GTP) promoter–regulatory region," *J. Biol. Chem.*, 261:9721–9726 (Jul. 25, 1986).

Simmons, et al., "ICAM, an adhesion ligand of LFA–1, is homologous to the neural cell adhesion molecule NCAM," *Nature*, 331:624–626 (1988).

Smith, et al., "Blocking of HIV–1 Infectivity by a Soluble, Secreted Form of the CD4 Antigen," *Science*, 238:1704–1707 (Dec. 18, 1987).

Sodroski, et al., "Location of the Trans–Activating Region On the Genome of Human T–Cell Lymphotropic Virus Type III," *Science*, 229:74–77 (Jul. 5, 1985).

Sodroski, et al., "Trans–Acting Transcriptional Regulation of Human T–Cell Leukemia Virus Type III Long Terminal Repeat," *Science*, 22:171–173 (Jan. 11, 1985).

Sorge et al., "Complete correction of the enzymatic defect of type I Gaucher disease fibroblasts by retroviral–mediated gene transfer," *Proc. Natl. Acad. Sci. USA*, 84:906–909 (Feb., 1987).

Tellier, et al., "New Strategies for AIDS Therapy and Prophylaxis," *Nature*, 318:414 (1985).

Tevethia et al., "Biology of Simian Virus 40 (SV40) Tranplantation Antigen (TrAg)," *Journal of Virology*, 107:13–23 (1980).

Torseth, et al., Native and Recombinant Herpes Simplex Virus Type 1 Envelope Protein Induce Human Immune T–Lymphocyte Responses, *J. Virol.*, 61(5):1532–1539 (1987).

Townsend, et al., "The Epitopes of Influenza Nucleoprotein Recognized by Cytotoxic T Lymphocytes Can Be Defined with Short Synthetic Peptides," *Cell*, 44:959–968 (Mar. 28, 1986).

Treisman, "Identification of a Protein–Binding Site That Mediates Transcriptional Response of the C–fos Gene to Serum Factors," *Cell*, 46:567–574 (Aug. 15, 1986).

Uchida, et al., "High Efficiency Gene Transfer Into Murine T Cell Clones Using a Retroviral Vector," *The Journal of Immunology*, 136(5):1876–1879 (Mar. 1, 1986).

Van Beveran, et al., "Nucleotide Sequence of the Genome of a Murine Sarcoma Virus," *Cell*, 27:97–108 (1981).

Walbot, et al., "Plant Development and Ribozymes for Pathogens," *Nature*, 334:196–197 (Jul. 21, 1988).

Wasmoen, et al., Biochemical and Amino Acid Sequence Analysis of Human Eosinophil Granule Major Basic Protein,: *J. Biol. Chem.*, 263:12559–12563 (1988).

Willis, et al., "Partial Phenotypic Correction of Human Lesch–Nyhan (Hypoxanthine–Guanine Phosphoribosyltransferase–deficient) Lymphoblasts with a Transmissble Retroviral Vector," *The Journal of Biological Chemistry*, 259(12):7842–7849 (Jun. 25, 1984).

Yamamoto et al., "Cloning and sequencing of mouse tyrosinase cDNA," *Jpn J. Genet*, 62:271–274 (1987).

Yasukawa and Zarling, "Human Cytotoxic T Cell Clones Directed Against Herpes Simplex Virus–Infected Cells. III. Analysis of Viral Glycoproteins Recognized by CTL Clones by Using Recombinant Herpes Simplex Viruses," *J. Immunol.*, 134(4):2679–2682, (1985).

Yee, et al., "Gene Expression From Transcriptionally Disabled Retroviral Vectors," *Proc. Nat'l Acad. Sci., USA*, 84:5197–5201 (Aug., 1987).

Yu, et al., "Self–Inactivating Retroviral Vectors Designed for Transfer of Whole Genes into Mammalian Cells," *Proc. Nat'l Acad. Sci., USA*, 83:3194–3198 (May, 1986).

Zagury, et al., "A group specific anamnestic immune reaction against HIV–1 induced by a candidate vaccine against AIDS," *Nature*, 332:728–731 (Apr. 21, 1988).

Zarling, et al., "Herpes Simplex Virus (HSV)–Specific Human T–Cell Clones Recognize HSV Glycoprotein D Expressed by a Recombinant Vaccinia Virus," *J. Virol.* 59(2):506–509 (1986).

Zarling, et al., Human Cytotoxic T Cell Clones Directed Against Herpes Simplex Virus–Infected Cells, IV. Recognition and Activation by Cloned Glycoproteins gB and gD,: *J. Immunol.*, 136(12):4669–4673 (Jun. 15, 1986).

Zinkernagel, et al., "MHC–Restricted Cytotoxic T Cells: Studies on the Biological Role of Polymorphic Major Transplantation Antigens Determining T–Cell Restriction–Specificity, Function, and Responsiveness," *Adv. In Immunol.*, 27:51–177 (1979).

Chong, et al., "Tumor Targets Stimulate IL–2 Activated Killer Cells to Produce Interferon–$\gamma$ and Tumor Necrosis Factor," *The Journal of Immunology*, 142:2133–2139 (Mar. 15, 1989).

Chouaib, et al., "Generation of lymphokine–activated killer cells: Synergy between tumor necrosis factor and interleukin 2," *Proc. Natl. Acad. Sci. USA* 85:6875–6879 (Sep., 1988).

Expevik, et al., "Transforming Growth Factor–$\beta$ (TGF–$\beta_1$) and Recombinant Human Tumor Necrosis Factor–$\alpha$ Reciprocally Regulate the Generation of Lymphokine–Activated Killer Cell Activity," *The Journal of Immunology*, 140(7):2312–2316.

Zarling, et al., "Herpes Simplex Virus (HSV)–Specific Human T–Cell Clones Recognize HSV Glycoprotein D Expressed by a Recombinant Vaccinia Virus," *J. Virol.* 59(2):506–509 (1986).

Migliori, et al., "Lymphokine–activated killer (LAK) cells can be focused at sites of tumor growth by products of macrophage activation," *Surgery*, 102(2):155–162.

Owen–Schaub, et al., "Synergy of Tumor Necrosis Factor and Interleukin 2 in the Activation of Human Cytotoxic Lymphocytes: Effects of Tumor Necrosis Factor $\alpha$ and Interleukin 2 in the Generation of Human Lymphokine–activated Killer Cell Cytotoxity," *Cancer Research*,48, 788–792 (Feb. 15, 1988).

Plate, et al., Cytokines Involved in the Generation of Cytolytic Effector T Lymphocytes", Annals of the New York Academy of Sciences, 532:149–157.

Tashiro, et al., "Signal Sequence Trap: A Cloning Strategy for Secreted Proteins and Type I Membrane Proteins," *Science*, 261:600–603 (Jul. 30, 1993).

Randall, et al., "Unity in Function in the Absence of Consensus in Sequence: Role of Leader Peptides in Export," *Science*, 243:1156–1159 (Mar. 3, 1989).

Watson, "Compilation of published signal sequences," *Nucleic Acids Research*,12(13):5145–5164 (1984).

Yang, et al., "Induction of lymphokine–activated killer cytotoxicity with interleukin–2 and tumor necrosis factor α against primary lung cancer targets," *Cancer Immunol. Immunother*, 29:193–198 (1989).

Rosenberg et al., "Gene Transfer Into Humans — Immunotherapy of Patients With Advanced Melanoma, Using Tumor–Infiltrating Lymphocytes Modified by Retroviral Gene Transduction," *The New England Journal of Medicine*, 323(9):570–578 (Aug. 30, 1990).

Hwu et al., "Functional and Molecular Characterization of Tumor–Infiltrating Lymphocytes Transduced with Tumor Necrosis Factor–α cDNA for the Gene Therapy of Cancer in Humans," *J. Immunol.*, 9(1):4104–4115 (1993).

Rosenberg, S.A., "Gene Therapy for Cancer," *JAMA*, 268(17):2416–2419 (1992).

Rosenberg, et al., "The Development of Gene Therapy for the Treatment of Cancer," *Annals of Surgery* 218(4):455–464 (1993).

Annual Report for 1995, IND Application to the FDA by Division of Cancer Treatment, Diagnosis and Centers, National Cancer Institute, "TNF–Transduced Tumor Infiltrating Lymphocytes With Or Without Interleukin–2" Serial No. 14, Jan. 22, 1996.

Rosenberg S.A., "The Immunotherapy and Gene Therapy of Cancer," *J. of Clinical Oncology* 10:(2):180–199 (Feb. 1992).

Miller et al., "Redesign of Retrovirus Packaging Cell Lines To Avoid Recombination Leading to Helper Virus Production," *Molecular And Cellular Biology*, 6(8):2895–2902 (Aug. 1986).

Kowalski et al., "Functional Regions of the Envelope Glycoprotein of Human Immunodeficiency Virus Type 1," *Science*, 237:1351–1355 (Sep. 11, 1987).

Rosenberg, S.A., "Adoptive Immunotherapy for Cancer," *Scientific American*, pp. 62–69 (May 1990).

Ueda et al., *Proc. Nat. Acad. Sci.* 84:3004–3008 (1987).

Yamada et al., *EMBO J.* 6(9):2705–2709 (1987).

Tang, P., et al. (1996) *Biochemistry* 35(25):8226–33.

Aggarwal et al., "Human Tumor Necrosis Factor," *J. Biol. Chem.*, 260(4):2345–2354 (Feb. 25, 1985).

Anderson, W.F. "Prospects for Human Gene Therapy," *Science*, 226:401–409 (Oct. 26, 1984).

Belldegrum et al., "Interleukin 2 Expanded Tumor–infiltrating Lymphocytes in Human Renal Cell Cancer: Isolation, Characterization, and Antitumor Activity," *Cancer Research*, 48:206–214 (Jan. 1, 1988).

Bender et al., "Evidence that the Packaging Signal of Maloney Murine Leukemia Virus Extends into the gag Region," *J. Virol.*, 61(5):1639–1646 (May, 1987).

Beutler et al., "Purification of Cachectin, A Lipoprotein Lipase–Suppressing Hormone Secreted by Endotoxin–Induced RAW 264.7 Cells," *J. Exp. Med.*, 161:984–995 (May, 1985).

Beutler et al., "Identity of Tumor Necrosis Factor and the Macrophage–Secreted Factor Cachectin," *Nature*, 316:552–554 (Aug, 1985).

Carswell et al., "An Endotoxin Induced Serum Factor that Causes Necrosis of Tumors," *Proc. Nat'l Acad. Sci., USA*, 72(9):3666–3670 (Sep., 1975).

Clewell, D.B., "Nature of Col $E_1$ Plasmid Replication in *Escherichia coli* in the Presence of Chloramphenicol," *J. Bacteriol.*, 110(2):667–676 (May, 1972).

Clewell et al., "Supercoiled Circular DNA–Protein Complex in *Escherichia coli*: Purification and Induced Conversion to an Open Circular DNA Form," *Proc. Nat'l Acad. Sci., USA*, 62:1159–1166 (1969).

Coffin, J., Genome Structure, In: *RNA Tumor Viruses*, vol. 2, Weiss et al., (Eds.), 2nd Edition, Cold Spring Harbor Monograph Series, Cold Spring Harbor Laboratory, Cold Spring Harbor, New York, pp. 17–73.

Cohen et al., "Nonchromosomal Antibiotic Resistance in Bacteria: Genetic Transformation of *Escherichia coli* by R–Factor DNA," *Proc. Nat'l Acad. Sci., USA*, 69(8):2110–2114 (Aug., 1972).

Cone et al., "High–efficiency Gene Transfer into Mammalian Cells: Generation of Helper–free Recombinant Retrovirus With Broad Mammalian Host Range," *Proc. Nat'l Acad. Sci., USA*, 81:6349–6353 (Oct., 1984).

Graham & Van Der Eb, "A New Technique for the Assay of Infectivity of Human Adenovirus 5 DNA," *Virology*, 52:456–467 (1973).

Gray et al., "Expression of Human Immune Interferon cDNA in *E. coli* and Monkey Cells," *Nature*, 295:503–508 (Feb. 11, 1982).

Jacobs et al., "Molecular Cloning, Sequencing, and Expression in *Escherichia coli* of Human Preprourokinase cDNA," *DNA*, 4(2):139–146 (1985).

Kriegler et al., "Transformation Mediated by the SV40 T Antigens: Separation of the Overlapping SV40 Early Genes with a Retroviral Vector," *Cell*, 38:483–491 (Sep., 1984).

Lang et al., "Expression of a Hemopoietic Growth Factor cDNA in a Factor–Dependent Cell Line Results in Autonomous Growth and Tumorigenicity," *Cell*, 43:531–542 (Dec., 1985).

Maniatis et al., *Molecular Cloning: A Laboratory Manual*, Cold Spring Harbor Laboratory, Cold Spring Harbor, New York, pp. 252–253 (1982).

Mann et al., "Construction of a Retrovirus Packaging Mutant and Its Use to Produce Helper–Free Defective Retrovirus," *Cell*, 33:153–159 (May, 1983).

Matteucci et al., "Synthesis of Deoxyoligonucleotides on a Polymer Support," *J. Am. Chem. Soc.*, 103:3185–3191 (1981).

Maxam et al., "Sequencing End–Labeled DNA with Base–Specific Chemical Cleavages," *Meth. Enzymol.*, 65:499–561 (1980).

McCormick, D., "Human Gene Therapy: The First Round," *Bio/Technology*, 3:689–693 (1985).

Messing et al., "New M13 Vectors for Cloning," *Methods in Enzymology*, 101:20–78 (1983).

Miller et al., "Improved Retroviral Vectors for Gene Transfer and Expression," *BioTechniques*, 7(9):980–988 (1989).

Miller et al., "Retrovirus–mediated Gene Transfer into Human Skin Fibroblasts," In: *Current Communications in Molecular Biology*, pp. 122–127 (1988).

Pennicia et al., "Human Tumor Necrosis Factor: Precursor, Structure, Expression, and Homology to Lymphotoxin," *Nature*, 312:724–729 (1984).

Rosenberg et al., "Use of Tumor Infiltrating Lymphocytes and Interleukin–2 in Immunotherapy of Patients with Metastatic Melanoma," *New England Journal of Medicine*, 319:1676–1680 (Dec. 22, 1988).

Rosenberg et al., "A New Approach to the Adoptive Immunotherapy of Cancer with Tumor–Infiltrating Lymphocytes," *Science*, 233:1318–1321 (Sep. 19, 1986).

Sanger et al., "DNA Sequencing with Chain–Terminating Inhibitors," *Proc. Nat'l Acad. Sci., USA*, 74(12):5463–5467 (Dec., 1977).

Smith et al., "In Vitro Mutagenesis," *Ann. Rev. Genet.*, 19:423–462 (1985).

Southern et al., "Transformation of Mammalian Cells to Antibiotic Resistance with a Bacterial Gene Under Control of the SV40 Early Region Promotor," *J. Mol. Appl. Gen.*, 1:327–341 (1982).

Topalian et al., "Immunotherapy of Patients with Advanced Cancer Using Tumor–infiltrating Lymphocytes and Recombinant Interleukin–2: A Pilot Study," *J. Clin. Oncol.*, 6:839–853 (1988).

Wang et al., "Molecular Cloning of the Complementary DNA for Human Tumor Necrosis Factor," *Science*, 228:149–154 (Apr. 12, 1985).

Weck et al., "Antiviral Activities of Hybrids of Two Major Human Leukocyte Interferons," *Nucleic Acids Research*, 9(22):6153–6166 (1981).

Wigler et al., "Biochemical Transfer of Single Copy Eukaryotic Genes Using Total Cellular DNA as Donor," *Cell*, 14:725–731 (Jul., 1978).

Williamson et al., "Human Tumor Necrosis Factor Produced by Human B–Cell Lines: Synergistic Cytotoxic Interaction with Human Interferon," *Proc. Nat'l Acad. Sci., USA*, 80:5397–5401 (Sep., 1983).

Zoller & Smith, "Oligonucleotide–Directed Mutagenesis: A Simple Method Using Two Oligonucleotide Primers and a Single–Stranded DNA Template," *Meth. Enzymol.*154:329–350 (1987).

Ledley et al., "Retroviral Mediated Gene Transfer of Human Phenylalanine Hydroxylase Into NIH 3T3 and Hepatoma Cells," *Proc. Nat'l Acad. Sci. USA*, 83:409–413 (1986).

Maxwell et al., "Regulated Expression of a Transfected Toxin Gene," *J. Cell. Biochem., Supplement 10D*, p. 39 (Mar. 30, 1986) (Abstract N93).

Maxwell et al., "Regulated Expression of a Diphtheria Toxin A–Chain Gene Transfected into Human Cells: Possible Strategy for Inducing Cancer Cell Suicide," *Cancer Res.*, 46:4660–4664 (Sep., 1986).

Rein et al., "Myristylation Site in Pr65$^{gag}$ Is Essential For Virus Particle Formation By Moloney Murine Leukemia Virus," *Proc. Nat'l acad. Sci., USA*, 83:7246–7250 (Oct., 1986).

Maxwell et al., "HTLV–Regulated Expression of a Transfected Diphtheria Toxin Gene," *J. Cell. Biol., Supplement 11D*, p. 314, p. 67 (Mar. 29, 1987) (Abstract).

Harrison et al., "Toward HIV–Regulated Expression of a Diphtheria Toxin A Gene In Transfected Cells," *J. Cell Biol., Supplement 13B*, p. 302 (Jan. 31, 1989) (Abstract G418).

Klein et al., "Separation and Characteristics of Tumor–Infiltrating Lymphocytes In Man," In: *Contemporary Topics In Immunobiology*, vol. 10, Witz and Manna, Jr., (Eds.), Plenum Press, New York, pp. 79–107 (1980).

Vose et al., "Separation of Tumor And Host Cell Populations from Human Neoplasms," In: *Cancer Cell Organelles*, Reid et al., (Eds.), Chinchester, Ellis Harwood Ltd., pp. 45–56 (1982).

Rosenberg et al., "A New Approach To the Adoptive Immunotherapy of Cancer with Tumor–Infiltrating Lymphocytes," *Science*, 223:1318–1321 (1986).

Spiess et al., "In Vivo Antitumor Activitiy of Tumor–Infiltrating Lymphocytes Expanded In Recombinant Interleukin–2," *JNCI*, 79:1067–1075 (Nov., 1987).

Muul et al., "Identification of Specific Cytolytic Immune Responses Against Autologous Tumor In Humans Bearing Malignant Melanoma," *J. Immunol.* 138:989–995 (1987).

Itoh et al., "Interleukin 2 Activation Of Cytotoxic T–lymphocytes Infiltrating Into Human Metastatic Melanoma," *Cancer Res.*, 46:3011–3017 (1986).

Kurnick, "Functional Characterization of T Lymphocytes Propagated From Human Lung Carcinomas," *Clin. Immunol. Immunopath.*, 38:367–80 (1986).

Rabinowich et al., "A Functional Analysis of Mononuclear Cells Infiltrating Into Tumors: Lysis of Autologous Human Tumor Cells By Cultured Infiltrating Lymphocytes," *Cancer Res.*, 47:173–177 (1987).

Miescher et al., "Clonal and Frequency Analyses of Tumor–Infiltrating T Lymphocytes From Human Solid Tumors," *J. Immunol.*, 138:4004–4011 (1987).

Topalian et al., "Expansion of Human Tumor Infiltrating Lymphocytes For Use in Immunotherapy Trials," *J. Immunol. Methods*, 102:127–141 (1987).

Belldegrun et al., "Interleukin 2 Expanded Tumor–Infiltrating Lymphocytes in Human Renal Cell Cancer: Isolation, Characterization, and Antitumor Activity," *Cancer Res.*, 48:206–214 (1988).

Buchan et al., "Interleukin–1 and Tumor Necrosis Factor mRNA Expression in Rheumatoid Arthritis: Prolonged Production of IL–1α," *Clin. Exp. Immunol.*, 73:449–455 (1988).

Altmann et al., "Contransfection of ICAM–1 and HLA–DR Reconstitutes Human Antigen–Presenting Cell Function in Mouse L Cells," *Nature*, 338:512–514 (1989).

Anderson et al., "Gene Expression in Implanted Rat Hepatocytes Following Retroviral–Mediated Gene Transfer," *Som. Cell and Mol. Genetics*, 15:215–227 (1989).

Anderson, W.F., "Prospects for Human Gene Therapy," *Science*, 226:401–409 (1984).

Armentano et al., "Effect of Internal Viral Sequences on the Utility of Retroviral Vectors," *J. Virology*, 61:1647–1650 (1987).

Arnold et al., "Vaccine Development for Aids Through Molecular Surgery of a Human Common Cold Virus Surface," *J. Cell. Biochem.*, L401:145 (1990).

Barnd et al., "Specific, Major Histocompatibility Complex–Unrestricted Recognition of Tumor–Associated Mucins By Human Cytotoxic T Cells," *Proc. Nat'l Acad. Sci., USA*, 86:7159–7163 (1989).

Berkner, K.L., "Development of Adenovirus Vectors for the Expression of Heterologous Genes," *BioTechniques*, 6:616–629 (1988).

Bernards et al. "Effective Tumor Immunotherapy Directed Against an Oncogene–Encoded Product Using a Vaccinia Virus Vector," *Proc. Nat'l Acad. Sci., USA*, 84:6854–6858 (1987).

Bernards et al., "N–myc Amplification Causes Down–Modulation of MHC Class I Antigen Expression in Neuroblastoma," *Cell*, 47:667–674 (1986).

Bolognesi et al., "Prospects of Treatment of Human Retrovirus–Associated Diseases," *Cancer Research, Supplement*, 45:4700s–4705s (1985).

Braciale et al., "Antigen Presentation Pathways to Class I and Class II MHC–Restricted T Lymphocytes," *Immunology Reviews*, 98:95–114 (1987).

Bubenik et al., "Local Administration of Cells Containing an Inserted IL–2 Gene and Producing IL–2 Inhibits Growth to Human Tumors in nu/nu Mice," *Immunology Letters*, 19:279–282 (1988).

Carey, J., "Human Gene Therapy: After a Lot of Looking, Now the Leap," *Business Week*, Science & Technology, pp. 133 & 136 (May 1, 1989).

Carr et al., "Genetic Transformation of Murine Bone Marrow Cells to Methotrexate Resistance," *Blood*, 62(1):180–185 (1983).

Cepko, C., "Retrovirus Vectors and Their Applications in Neurobiology," *Neuron*, 1:345–353 (1988).

Chakrabarti et al., "Expression of the HTLV–III Envelope Gene by a Recombinant Vaccinia Virus," *Nature*, 320:535–537 (1986).

Chan et al., "Mammalian Sarcoma–Leukemia Viruses. I. Infection of Feline, Bovine, and Human Cell Cultures With Snyder–Theilen Feline Sarcoma Virus," *J. Nat'l Cancer Inst.*, 52(2):473–481 (1974).

Cline et al., "Gene Transfer in Intact Animals," *Nature*, 284:422–425 (1980).

Collins et al., "Transfer of Functional EGF Receptors to an IL3–Dependent Cell Line," *J. Cell. Physiology*, 137:293–298 (1988).

Cone et al., "HLA–DR Gene Expression in a Proliferating Human Thyroid Cell Clone (12S)" *Endocrinology*, 123(4):2067–2074 (1988).

Cortes et al., "Successful Immuotherapy in a Murine Metastasizing Fibrosarcoma Model," *J. Surg. Onco.*, 25:289–295 (1984).

Crowley et al., "Generation of Human Autologous Melanoma–specific Cytotoxic T–Cells Using HLA–A2–matched Allogeneic Melanomas," *Cancer Research*, 50:492–498 (1990).

Culliton, B.J., "Designing Cells to Deliver Drugs," *Science(News & Comment)*, 246:746–751 (1989).

Dallo et al., "Humoral Immune Response Elicited by Highly Attenuated Variants of Vaccinia Virus and by an Attenuated Recombinant Expressing HIV–1 Envelope Protein," *Virology*, 173:323–329 (1989).

De Baetselier et al., "Differential Expression of H–2 Gene Products in Tumour Cells is Associated with Their Metastatogenic Properties," *Nature*, 288:179–181 (Nov. 13, 1980).

Deen et al., "A Soluble Form of CD4(T4) Protein Inhibits AIDS Virus Infection," *Nature*, 331:82–84 (Jan. 7, 1988).

Doherty et al., "Recombinant Vaccinia Viruses and the Development of Immunization Strategies Using Influenza Virus," *J. Inf. Diseases*, 159(6):1119–1122 (Jun., 1989).

Donner et al., "McDonough Feline Sarcoma Virus: Characterization of the Molecularly Cloned Provirus and Its Feline Oncogene (v–fms)," *J. Virol*, 41(2):489–500 (1982).

Ellrodt et al., "The Hidden Dangers of AIDS Vaccination," *Nature*, 325:765 (1987).

Embretson et al., "Pseudotyped Retroviral Vectors Reveal Restrictions to Reticuloendotheliosis Virus Replication in Rat Cells," *J. Virology*, 60(2):662–668 (1986).

Episkopou et al, "Cell–specified Expression of a Selectable Hybrid Gene," *Proc. Nat'l Acad. Sci., USA*, 81:4657–4661 (1984).

Estin et al., "Recombinant Vaccinia Virus Vaccine Against the Human Melanoma Antigen p97 for Use in immunotherapy," *Proc. Nat'l Acad. Sci., USA*, 85:1052–1056 (1988).

Evans et al., "An Engineered Poliovirus Chimaera Elicits Broadly Reactive HIV–1 Neutralizing Antibodies," *Nature*, 339:385–388 (1989).

Fauci et al., "Development and Evaluation of a Vaccine for Human Immunodeficiency Virus (HIV) Infection," *Ann. Intern. Med.*, 110(5):373–385 (1989).

Fisher–Hoch et al., "Protection of Rhesus Monkeys From Fatal Lassa Fever by Vaccination With a Recombinant Vaccinia Virus Containing the Lassa Virus Glycoprotein," *Proc. Nat'l Acad. Sci. USA*, 86:317–321 (1989).

Flexner et al., "Characterization of Human Immunodeficiency Virus gag/pol Gene Products Expressed by Recombinant Vaccinia Viruses," *Virology*, 166:339–349 (1988).

Friedmann, T., "Progress Toward Human Gene Therapy," *Science*, 244:1275–1281 (1989).

Friedmann, T., "The Future For Gene–Therapy—A Reevaluation," *Ann. N.Y. Acad. Sci.*, 265:141–152 (1975).

Gattoni–Celli et al., "Partial Suppression of Anchorage–Independent Growth and Tumorigenicity in Immunodeficient Mice by Transfection of the H–2 Class I Gene H–2L$^d$ into a Human Colon Cancer Cell Line (HCT)," *Proc. Nat'l Acad. Sci., USA*, 85:8543–8547 (1988).

Gilboa, E. "Retroviral Gene Transfer: Applications to Human Therapy," Memorial Sloan–Kettering Cancer Center, Program in Molecular Biology, New York, New York, *Prog. Clin. Biol. Res., USA*, 352:301–311 (1990).

Gruber et al., "Retroviral Vector–Mediated Gene Transfer into Human Hematopoietic Progenitor Cells," *Science*, 230:1057–1061 (1985).

Guarini et al., "In Vitro Differentiation and Antigenic Changes in Human Melanoma Cell Lines," *Cancer Immunol. Immunother.*, 30:262–268 (1989).

Hatzoglou et al., "Hormonal Regulation of Chimeric Genes Containing the Phosphoenolpyruvate Carboxykinase Promoter Regulatory Region in Hepatoma Cells Infected by Murine Retroviruses," *J. Biol. Chem.*, 263(33):17798–17808 (1988).

Hellerman et al., "Secretion of Human Parathyroid Hormone From Rat Pituitary Cells Infected With a Recombinant Retrovirus Encoding Preproparathyroid Hormone," *Proc. Nat'l Acad. Sci., USA*, 81:5340–5344 (1984).

Hoffenbach et al., "Unusually High Frequencies of HIV–Specific Cytotoxic T Lymphocytes in Humans," *J. Immunol.*, 142:452–462 (1989).

Holt et al., "Inducible Production of c–fos Antisense RNA Inhibits 3T3 Cell Proliferation," *Proc. Nat'l Acad. Sci., USA*, 83:4794–4798 (1986).

Howell et al., "Gene Therapy for Thioguanine–resistant Human Leukemia," *Mol. Biol. Med.*, 4:157–168 (1987).

Hu et al., "Effect of Immunization with a Vaccinia–HIV env Recombinant on HIV Infection of Chimpanzees," *Nature*, 328:721–723 (1987).

Hunt et al., "Retrovirus–Expressed Hemagglutinin Protects against Lethal Influenza Virus Infections," *J. Virology*, 62:3014–3019 (1988).

Hussey et al., "A Soluble CD4 Protein Selectively Inhibits HIV Replication and Syncytium Formation," *Nature*, 331:78–81 (1988).

Isobe et al., "Induction of Antitumor Immunity in Mice by Allo–Major Histocompatibility Complex I Gene Tranfectant With Strong Antigen Expression," *J. Nat. Cancer Inst.*, 81:1823–1828 (1989).

Izant and Weintraub, "Constitutive and Conditional Suppression of Exogenous and Endogenous Genes by Anti–Sense RNA," *Science*, 229:345–352 (1985).

Jolly et al., "Induction of Anti–HIV–1 Immune Responses by Retroviral Vectors," *Biotechnology Therapeutics*, 2(12):179–193 (1990–1991).

Joly et al., "Cell–Mediated Suppression of HIV–Specific Cytotoxic T Lymphocytes," *J. Immunol.*, 143(7):2193–2201 (1989).

Joyner et al., "Construction and Transfer of Recombinant Retrovirus Clones Carrying the HSV–1 Thymidine Kinase Gene," *The Ontario Cancer Institute, Department of Medical Biophysics, University of Toronto, Toronto, Canada, Developmental Biology Using Purified Genes*, pp. 535–546 (1981).

Joyner et al., "Retrovirus Transfer of a Bacterial Gene Into Mouse Hematopoietic Progenitor Cells," *Nature*, 305:556–558 (1983).

Kantoff et al., "Expression of Human Adenosine Deaminase in Nonhuman Primates After Retrovirus–Mediated Gene Transfer," *J. Exp. Med.*, 166:219–234 (1987).

Kasid et al., "Human Gene Transfer; Characterization of Human Tumor–Infiltrating Lymphocytes as Vehicles for Retroviral–Mediated Gene Transfer in Man," *Proc. Nat'l Acad. Sci., USA*, 87:473–477 (1990).

Kast et al., "Eradication of Adenovirus E1–Induced Tumors by E1A–Specific Cytotoxic T Lymphocytes," *Cell*, 59:603–614 (1989).

Katoh et al., "Inhibition of Retroviral Protease Activity by an Aspartyl Proteinase Inhibitor," *Nature*, 329:654–656 (Oct. 15–21, 1987).

Keller et al., "Expression of a Foreign Gene in Myeloid and Lymphoid Cells Derived From Multipotent Haematopoietic Precursors," *Nature*, 318:149–154 (1985).

Klavinskis et al., "Molecularly Engineered Vaccine Which Expresses an Immunodominant T–Cell Epitope Induces Cytotoxic T Lymphocytes That Confer Protection from Lethal Virus Infection," *J. Virol.*, 63(10):4311–4316 (1989).

Kohn et al., "Retroviral–Mediated Gene Transfer into Mammalian Cells," *Blood Cells*, 13:285–298 (1987).

Korman et al., "Expression of Human Class II Major Histocompatibility Complex Antigens Using Retrovirus Vectors," *Proc. Nat'l Acad. Sci., USA*, 84:2150–2154 (1987).

Kourilsky et al., "MHC–Antigen Interaction: What Does the T Cell Receptor See?," *Adv. in Immunol.*, 45:107–193 (1989).

Lang et al., "Expression of a Hemopoietic Growth Factor cDNA in a Factor–Dependent Cell Line Results in Autonomous Growth and Tumorigenicity," *Cell*, 43(2 Pt 1):531–542 (Dec., 1985).

Lathe et al., "Tumour Prevention and Rejection With Recombinant Vaccinia," *Nature*, 326:878–880 (Apr. 30, 1987).

Ledley, F.D., "Somatic Gene Therapy for Human Disease: Background and Prospects (Part I)," *J. Pediatrics*, 110(1):1–8 (Jan., 1987).

Lee, R.E., "Gene Therapy: Clipping the Wings of Nature's Own Gene Transfer Vectors," *Can. Med. Assoc. J.*, 134:311–313 (Feb. 15, 1986).

Linial et al., "An Avian Oncovirus Mutant (SE 21Q1b) Deficient in Genomic RNA: Biological and Biochemical Characterization," *Cell*, 15:1371–1381 (1978).

Linial, M., "Transfer of Defective Avian Tumor Virus Genomes by a Rous Sarcoma Virus RNA Packaging Mutant," *J. Virology*, 38(1):380–382 (Apr., 1981).

Lotteau et al., "Modulation of HLA Class II Antigen Expression by Transfection of Sense and Antisense DRα cDNA," *J. Exp. Med.*, 169:351–356 (1989).

Lotze et al., "Recent Advances in Cellular Immunology: Implication for Immunity to Cancer," *Immunology*, 11:190–193 (1990).

Luytjes et al., "Amplification, Expression, and Packing of a Foreign Gene by Influenza Virus," *Cell*, 59:1107–1113 (1989).

Mason et al., "The Hypogonadal Mouse: Reproductive Functions Restored by Gene Therapy," *Science*, 234:1372–1378 (1986).

McAleer et al., "Human Hapatitis B Vaccine from Recombinant Yeast," *Nature*, 307:178–180 (1984).

McCune et al., "Endoproteolytic Cleavage of gp160 Is Required for the Activation of Human Immunodeficiency Virus," *Cell*, 53:55–67 (1988).

McMichael et al., "Cytotoxic T–Cell Immunity to Influenza," *The New England J. Med.*, 309:13–17 (1983).

Mercola et al., "Insertion of a New Gene of Viral Origin into Bone Marrow Cells of Mice," *Science*, 208:1033–1035 (1980).

Merz, B., "Gene Therapy May Have Future Role in Cancer Treatment," *JAMA*, 257:150–151 (1987).

Michel et al., "HIV–Specific T Lymphocyte Immunity in Mice Immunized with a Recombinant Vaccinia Virus," *Eur. J. Immunol.*, 18:1917–1924 (1988).

Miller, A.D., "Retrovirus Packaging Cells," *Human Gene Therapy*, 1:5–14 (1990).

Miller et al., "Expression of a Retrovirus Encoding Human HPRT in Mice," *Science*, 225:630–632 (1984).

McMichael et al., "Cytotoxic T–Cell Immunity to Influenza," *The New England J. Med.*, 309:13–17 (1983).

Miller et al., "A Transmissible Retrovirus Expressing Human Hypoxanthine Phosphoribosyltransferase (HPRT): Gene Transfer into Cells Obtained From Humans Deficient in HPRT," *Proc. Nat'l Acad. Sci., USA*, 80:4709–4713 (1983).

Morgan et al., "Expression of an Exogenous Growth Hormone Gene by Transplantable human Epidermal Cells," *Science*, 237:1476–1479 (1987).

Morrow, J.F., "The Prospects for Gene Therapy in Humans," *Ann. N.Y. Acad. Sci.*, 265:13–21 (1975).

Mulligan, R.C., "Construction of Highly Transmissible Mammalian Cloning Vehicles Derived from Murine Retroviruses," *Experimental Manipulation of Gene Expression*, 8:155–173 (1983).

Nabel et al., "Recombinant Gene Expression in Vivo Within Endothelial Cells of the Arterial Wall," *Science*, 244:1342–1344 (1989).

Newell et al., "Herpes Simplex Virus–Induced Stromal Keratitis: Role of T–Lymphocyte Subsets in Immunopathology," *J. Virol.*, 63(2):769–775 (1989).

Nixon et al., "HIV–1 gag–Specific Cytotoxic T Lymphocytes Defined with Recombinant Vaccinia Virus and Synthetic Peptides," *Nature*, 336:484–487 (1988).

Overell et al., "Stably Transmitted Triple–Promoter Retroviral Vectors and Their Use in Transformation of Primary Mammalian Cells," *Mol. and Cell. Biol.*, 8:1803–1808 (1988).

Panicali et al., "Construction of Live Vaccines by Using Genetically Engineered Poxviruses: Biological activity of Recombinant Vaccinia Virus Expressing Influenza Virus Hemagglutinin," *Proc. Nat'l Acad. Sci., USA*, 80:5364–5368 (1983).

Plata et al., "AIDS Virus–Specific Cytotoxic T Lymphocytes in Lung Disorders," *Nature*, 328:348–351 (1987).

Quinnan, Jr. et al., "Cytotoxic T Cells in Cytomegalovirus Infection: HLA–Restricted T–Lymphocyte and Non–T–Lymphocyte Cytotoxic Responses Correlate with Recovery from Cytomegalovirus Infection in Bone–Marrow–Transplant Recipients," *New Eng. J. Med.*, 307:7–13 (1982).

Reif, A.E., "Vaccination of Adult and Newborn Mice of a Resistant Strain (C57BL/6J) against Challenge with Leukemias Induced by Moloney Murine Leukemia Virus," *Cancer Research*, 45:25–31 (1985).

Reimann et al., "Introduction of a Selectable Gene Into Murine T–Lymphoblasts by a Retroviral Vector," *J. Immunol. Methods*, 89:93–101 (1986).

Rota et al., "Comparison of Inactivated, Live and Recombinant DNA Vaccines Against Influenza Virus in a Mouse Model," *Virus Research*, 16:83–93 (1990).

Rouse et al., "Antiviral Cytotoxic T Lymphocyte Induction and Vaccination," *Rev. Infect. Dis.*, 10:16–33 (1988).

Rubenstein et al., "Construction of a Retrovirus Capable of Transducing and Expressing Genes in Multipotential Embryonic Cells," *Proc. Nat'l Acad. Sci., USA*, 81:7137–7140 (1984).

Ruscetti et al., "Three Independent Isolates of Feline Sarcoma Virus Code for Three Distinct gag–x Polyproteins," *J. Virol.*, 35(1):259–264 (1980).

Sabin et al., "History of Sabin Attenuated Poliovirus Oral Live Vaccine Strains," *J. Biol. Standardization*, 1:115–118 (1973).

Saito et al., "The Generation and Selection of the T Cell Repertoire: Insights from Studies of the Molecular Basis of T Cell Recognition," *Immunological Reviews*, 101:81–193 (1988).

Salk, J. "Prospects for the Control of AIDS by Immunizing Seropositive Individuals," *Nature*, 327:473–476 (1987).

Shimotohno et al., "Formation of Infectious Progeny Virus after Insertion of Herpes Simplex Thymidine Kinase Gene into DNA of an Avian Retrovirus," *Cell*, 26:67–77 (1981).

Shinitzky and Skornick, "Cancer Immunotherapy With Autologous and Allogeneic Vaccines: A Practical Overview," *EORTC Genitourinary Group Monograph Basic Research and Treatment of Renal Cell Carcinoma Metastasis*, 9:95–125 (1990).

Siu et al., "Isolation of the Murine Intercellular Adhesion Molecule 1(ICAM–1) Gene: ICAM–1 Enhances Antigen –Specific T Cell Activation," *J. Immunology*, 143:3813–3820 (1989).

Sleckman et al., "Expression and Function of CD4 in a Murine T–Cell Hybridoma," *Nature*, 328:351–353 (Jul. 23, 1987).

Smith et al., "Loss of HLA–A,B,C Allele Products and Lymphocyte Function–Associated Antigen 3 in Colorectal Neoplasia," *Proc. Nat'l Acad. Sci., USA*, 86:5557–5561 (1989).

St. Louis et al., "An Alternative Approach to Somatic Cell Gene Therapy," *Proc. Nat'l Acad. Sci., USA*, 85:3150–3154 (1988).

Strair et al., "Recombinant Retroviruses Encoding Cell Surface Antigens as Selectable Markers," *J. Virology*, 62(12):4756–4759 (1988).

Stratowa et al., "Recombinant Retroviral DNA Yielding High Expression of Hepatitis B Surface Antigen," *EMBO J.*, 1(12):1573–1578 (1982).

Strebel et al., "The HIV 'A' (sor) Gene Product is Essential for Virus Infectivity," *Nature*, 328:728–730 (1987).

Stuhlmann et al., "Introduction of a Selectable Gene into Different Animal Tissue by a Retrovirus Recombinant Vector," *Proc. Nat'l Acad. Sci.*, 81:7151–7155 (1984).

Suter et al., "Cytotoxic Immune Response of Puppies to Feline Sarcoma Virus Induced Tumors," *Veterinary Immunology and Immunopathology*, 7:131–138 (1984).

Tabin et al., "Adaptation of a Retrovirus as a Eucaryotic Vector Transmitting the Herpes Simplex Virus Thymidine Kinase Gene," *Mol. Cell. Biol.*, 2(4):426–436 (Apr., 1982).

Takahashi et al., "A Single Amino Acid Interchange Yields Reciprocal CTL Specificities for HIV–1 gp160," *Science*, 246:118–121 (1989).

Takahashi et al., "An Immunodominant Epitope of the Human Immunodeficiency Virus Envelope Glycoprotein gp160 Recognized by Class I Major Histocompatibility Complex Molecule–Restricted Murine Cytotoxic T Lymphocytes," *Proc. Nat'l Acad. Sci., USA*, 85:3105–3109 (1988).

Temin, H.M., "Retrovirus Vectors: Promise and Reality," *Science*, 246:983 (1989).

Thomason and Booth, "Stable Incorporation of a Bacterial Gene into Adult Rat Skeletal Muscle in Vivo," *Amer. J. Physiology*, 258:C578–C581 (1990).

Townsend et al., "Cytotoxic T Cells Recognize Fragments of the Influenza Nucleoprotein," *Cell*, 42:457–467 (1985).

Traversari et al., "Expression of Retrovirus–Related, Cytotoxic T Lymphocyte– and Transplantation–Defined Antigens in NIH/3T3 Transfectants After a Single Passage in Nude Mice," *J. Immunol.*, 142:2887–2894 (1989).

Van Den Eynde et al., "Presence on a Human Melanoma of Multiple antigens Recognized by Autologous CTL," *Int. J. Cancer*, 44:634–640 (1989).

Wachsman et al., "HTLV x Gene Mutants Exhibit Novel Transcriptional Regulatory Phenotypes," *Science*, 235:674–677 (Feb. 6, 1987).

Walker et al., "HIV–1 Reverse Transcriptase Is a Target for Cytotoxic T Lymphocytes in Infected Individuals," *Science*, 240:64–66 (1988).

Walker et al., "HIV–specific Cytotoxic T Lymphocytes in Seropositive Individuals," *Nature*, 328:345–348 (1987).

Wallich et al., "Abrogation of Metastatic Properties of Tumor Cells by de novo Expression of H–2K Antigens Following H–2 Gene Transfection," *Nature*, 315:301–305 (1985).

Watanabe et al., "Construction of a Helper Cell Line for Avian Reticuloendotheliosis Virus Cloning Vectors," *Mol. And Cell. Biol.*, 3(12):2241–2249 (1983).

Watanabe et al., "Encapsidation Sequences for Spleen Necrosis Virus, An Avian Retrovirus, are Between the 5' Long Terminal Repeat and the Start of the gag Gene," *Proc. Nat'l Acad. Sci., USA*, 79:5986–5990 (1982).

Wathen et al., "Immunization of Cotton Rats with the Human Respiratory Syncytial Virus F Glycoprotein Produced Using a Baculovirus Vector," *J. Infect. Disease*, 159:255–264 (Feb., 1989).

Weber and Jay, "MHC Class I Gene Expression by Tumors: Immunotherapeutic Implications," *Curr. Top. Microbiol. Immunol.*, 137:140–147 (1988).

Weber et al., "Immunotherapy of a Murine Tumor with Interleukin 2," *J. Exp. Med.*, 166:1716–1733 (1987).

Wei et al., "Construction and Isolation of a Transmissible Retrovirus Containing the src Gene of Harvey Murine Sarcoma Virus and the Thymidine Kinase Gene of Herpes Simplex Virus Type 1," *J. Virology*, 39(3):935–944 (1981).

Weis et al., "Eukaryotic Chromosome Transfer: Linkage of the Murine Major Histocompatibility Complex to an Inserted Dominant Selectable Marker," *Proc. Nat'l Acad. Sci., USA*, 81:4879–4883 (1984).

Weis et al., "H–2L$^d$ Antigen Encoded by a Recombinant Retrovirus Genome Is Expressed on the Surface of Infected Cells," *Mol. & Cell. Biol.*, 5(6):1379–1384 (1985).

Wilson et al., "Correction of CD18–Deficient Lymphocytes by Retrovirus–Mediated Gene Transfer," *Science*, 248:1413–1416 (Jun., 1990).

Wilson et al., "Implantation of Vascular Grafts Lined with Genetically Modified Endothelial Cells," *Science*, 244:1344–1346 (1989).

Wolff et al., "Grafting Fibroblasts Genetically Modified to Produce L–dopa in a Rat Model of Parkinson Disease," *Proc. Nat'l Acad. Sci., USA*, 86:9011–9014.

Wong et al., "Retroviral Transfer and Expression of the Interleukin–3 Gene in Hemopoietic Cells," *Genes Dev.*, 1:358–365 (1987).

Xu et al., "Factors Affecting Long–Term Stability of Moloney Murine Leukemia Virus–Based Vectors," *Virology*, 171:331–341 (1989).

Yap et al., "Transfer of Specific Cytotoxic T Lymphocytes Protects Mice Inoculated with Influenza Virus," *Nature*, 273:238–239 (1978).

Zagury et al., "Immunization Against AIDS in Humans," *Nature*, 326:249–250 (1987).

Zarling et al., "Proliferative and Cytotoxic T Cells to AIDS Virus Glycoproteins in Chimpanzees Immunized with a Recombinant Vaccinia Virus Expressing AIDS Virus Envelope Glycoproteins," *J. Immunol.*, 139:988–990 (1987).

Zarling et al., "T–Cell Responses to Human AIDS Virus in Macaques Immunized with Recombinant Vaccinia Viruses," *Nature*, 323:344–346 (1986).

Zarling et al., "Herpes Simplex Virus (HSV)–Specific Proliferative and Cytotoxic T–Cell Responses in Humans Immunized with an HSV Type 2 Glycoprotein Subunit Vaccine," *J. Virol.*, 62(12):4481–4485 (Dec., 1988).

Zbar et al., "Tumor Rejection Mediated by an Amphotrophic Murine Leukemia Virus," *Cancer Research*, 43:46–53 (1983).

Zinkernagel et al., "Antiviral Protection By Virus–Immune Cytotoxic T Cells: Infected Target Cells Are Lysed Before Infectious Virus Progeny Is Assembled," *J. Exp. Med.*, 145:644–651 (1977).

Zwiebel et al., "Drug Delivery by Genetically Engineered Cell Implants," *Ann. N.Y. Acad. Sci.*, 618:394–404 (1990).

Verma et al., "Expression and Regulation of Rat Growth Hormone Gene in Mouse Fibroblasts," In: *Eukaryotic Viral Vectors*, Gluzman, Y, (Ed.), Cold Spring Harbor Laboratory, pp. 159–164 (1982).

Czarniecki et al., "Synergistic Antiviral and Antiproliferative Activities of *Escherichia coli*–Derived Human Alpha, Beta, and Gamma Interferons," *J. Virology*, 49(2):490–496 (1984).

Davison et al., "The Complete DNA Sequence of Varicella–Zoster Virus," *J. Gen. Virol.*, 67:1759–1816 (1986).

Temin, H.M., "Retrovirus Vectors For Gene Transfer: Efficient Integration Into and Expression of Exogenous DNA in Vertebrate Cell Genomes," In: *Gene Transfer*, Kucherlapati, R., (Ed.), Plenum Press, New york, pp. 149–187 (1986).

Field et al., "Isolation and Characterization of Acyclovir–resistant Mutants of Herpes Simplex Virus," *J. General Virology*, 49:115–124 (1980).

Moolten, "Tumor Chemosensitivity Conferred by Inserted Herpes Thymidine Kinase Genes Paradigm for a Prospective Cancer Control Strategy," *Cancer Res.*, 46:5276–5281 (1986).

Besnard et al., "Selection Against Expression of the *Escherichia coli* Gene gpt in hprt$^+$ Mouse Teratocarcinoma and Hybrid Cells," *Mol. Cell. Biol.*, 7(11):4139–4141 (1987).

Borrelli et al., "Targeting of an Inducible Toxic Phenotype in Animal Cells," *Proc. Nat'l Acad. Sci.*, 85:7572–7576 (1988).

Toohey et al., "Multiple Hormone–Inducible Enhancers as Mediators of Differential Transcription," *Mol. Cell. Biol.*, 6(12):4526–4538 (1986).

Doppler et al., "Prolactin and Glucocorticoid Hormones Synergistically Induce Expression of Transfixed Rat β–Casein Gene Promoter Constructs in a Mammary Epithelial Cell Line," *Proc. Nat'l Acad. Sci.*, 86:104–108 (1989).

Searle et al., "The Potential of Carboxypeptidase G$_2$–Antibody Conjugates as Anti–Tumour Agents. I. Preparation of Antihuman Chorionic Gonadotropin–Carboxypeptidase G$_2$ and Cytotoxicity of the Conjugate Against JAR Choriocarcinoma Cells in Vitro," *Brit. J. Can.*, 263(33):17798–17808 (1988).

Deng et al., "The Mouse Thymidylate Synthase Promoter: Essential Elements Are in Close Proximity to the Transcriptional Initiation Sites," *Mol. Cell. Biol.*, 9(9):4079–4082 (1989).

Rosen et al., "Intragenic Cis–Acting art Gene–Responsive Sequences of the Human Immunodeficiency Virus," *Proc. Nat'l Acad. Sci., USA*, 85:2071–2075 (1988).

Irvin, "Purification and Partial Characterization of the Antiviral Protein from *Phytolacca americana* Which Inhibits Eukaryotic Protein Synthesis," *Archives of Biochemistry and Biophysics*, 169:522–528 (1975).

Mulligan et al., "Synthesis of Rabbit β–Globulin in Cultured Monkey Kidney Cells Following Infection with a SV40 β–Globulin Recombinant Genome," *Nature*, 277:108–114 (1979).

Irvin et al., Purification and Properties of a Second Antiviral Protein from *Phytolacca americana* Which Inactivates Eukaryotic Ribosomes: *Archives of Biochemistry and Biophysics*, 200(2):418–425 (1980).

Stripe et al., "Gelonin, a New Inhibitor of Protein Synthesis, Nontoxic to Intact Cells," *J. Biol. Chem.*, 255(14):6947–6953 (1980).

Parnes et al., "Mouse β$_2$–Microglobulin cDNA Clones: A Screening Procedure for cDNA Clones Corresponding to Rare mRNAs," *Proc. Nat'l Acad. Sci. USA*, 78(4):2253–2257 (1981).

Barbieri et al., "Purification and Partial Characterization of Another Form of the Antiviral Protein From the Seeds of *Phytolacca americana* L. (Pokeweed)," *Biochem. J.*, 203:55–59 (1982).

Ball et al., "Monoclonal Antibodies to Myeloid Differentiation Antigens: In Vivo Studies of Three Patients With Acute Myelogenous Leukemia," *Blood*, 62(6):1203–1210 (1983).

Mekalanos et al., "Cholera Toxin Genes: Nucleotide Sequence, Deletion Analysis and Vaccine Development," *Nature*, 306:551–557 (1983).

Dubensky et al., "Direct Transfection of Viral and Plasmid DNA into the Liver or Spleen of Mice," *Proc. Nat'l Acad. Sci., USA*, 81:7529–7533 (1984).

Stanton et al., "Nucleotide Sequence Comparison of Normal and Translocated Murine c–myc Genes," *Nature*, 310:423–425 (1984).

Eglitis et al., "Gene Expression in Mice After High Efficiency Retroviral–Mediated Gene Transfer," *Science*, 230:1395–1398 (1985).

Coussens et al., "Tyrosine Kinase Receptor with Extensive Homology to EGF Receptor Shares Chromosomal Location with neu Oncogene," *Science*, 230:1138–1139 (1985).

Lamb et al., "Nucleotide Sequence of Cloned cDNA Coding for Preproricin," *Eur. J. Biochem.*, 148:265–270 (1985).

Tweten et al., "Diptheria Toxin — Effect of Substituting Aspartic Acid for Glutamic Acid 148 on ADP Ribosyltransferase Activity," *J. Biol. Chem.*, 260:10392–10394 (1985).

Rosenberg et al., "Observations on the Systemic Administration of Autologous Lymphokine–Activated Killer Cells and Recombinant Interleukin–2 to Patients with Metastatic Cancer," *New Eng. J. Med.*, 313(23):1485–1492 (1985).

Furman et al., "Phosphorylation of 3'–azido–3'deoxythymidine and lective Interaction of the 5'–trisphosphate with Human Immunodeficiency Virus Reverse Transcriptase," *Proc. Nat'l Acad. Sci., USA*, 83:8333–8337 (1987).

Lifson et al., "AIDS Retrovirus Induced Cytopathology: Giant Cell Formation and Involvement of CD4 Antigen," *Science*, 232:1123–1127 (1986).

Lifson et al., "Role od Envelope Glycoprotein Carbohydrate in Human Immunodeficiency Virus (HIV) Infectivity and Virus–Induced Cell Fusion," *J. Exper. Med.*, 164:2101–2106 (1986).

McDougal et al., "Binding of HTLV–III/LAV to T4+T Cells by a Complex of the 110K Viral Protein and the T4 Molecule," *Science*, 231:382–385 (1986).

Pert et al., "Octapeptides Deduced from the Neuropeptide Receptor–like Pattern of Antigen T4 in Brain Patently Inhibit Human Immunodeficiency Virus Receptor Binding and T–Cell Infectivity," *Proc. Nat'l Acad. Sci., USA*, 83:9254–9258 (1986).

To et al., "Inhibition of Retroviral Replication by Anti–Sense RNA," *Mol. Cell. Biol.*, 6:4758–4762 (1986).

Goodbourn et al., "The Human β–Interferon Gene Enhancer Is Under Negative Control," *Cell*, 45:601–610 (1986).

Krissansen et al., "Chromosomal Locations of the Gene Coding for the CD3 (T3) Gamma Subunit of the Human and Mouse CD3/T–Cell Antigen Receptor Complexes," *Immunogenetics*, 26:258–266 (1987).

Wang and Huang, "pH–Sensitive Immunoliposomes Mediate Target–Cell–Specific Delivery and Controlled Expression of a Foreign Gene in Mouse," *Proc. Nat'l Acad. Sci., USA*, 84:7851–7855 (1987).

Jackson et al., "Nucleotide Sequence Analysis of the Structural Genes for Shiga–like Toxin I Encoded by Bacteriophage 900J from *Escherichia coli*," *Microbial Pathogenesis*, 2:147–153 (1987).

Maher, III and Dolnick, "Specific Hybridization Arrest of Dihydrofolate Reductase mRNA in Vitro Using Anti–Sense RNA or Anti–Sense Oligonucleotides," *Archives of Biochemistry and Biophysics*, 253(1):214–220 (1987).

Carroll and Collier, "Active Site of *Psuedomonas aeruginosa* Exotoxin A," *J. Biol. Chem.*, 262(18):8707–8711 (1987).

Bzik et al., "Molecular Cloning and Sequence Analysis of the *Plasmodium falciparum* Dihyrofolate Reductase–Thymidylate Synthase Gene," *Proc. Nat'l Acad. Sci., USA*, 84:8360–8364 (1987).

Calderwood et al., "Nucleotide Sequence of the Shiga–like Toxin Genes of *Escherichia coli*," *Proc. Nat'l Acad. Sci., USA*, 84:4364–4368 (1987).

Wallner et al., "Primary Structure of Lymphocyte Function–Associated Antigen 3 (LFA–3): The Ligand of the T Lymphocyte CD2 Glycoprotein," *J. Exper. Med.*, 166:923–932 (1987).

Tal et al., "Human HER2 (neu) Promoter: Evidence for Multiple Mechanisms for Transcriptional Initiation," *Mol. Cell. Biol.*, 7(7):2597–2601 (1987).

Dillman, "Antibody Therapy," *Principles of Cancer Biotherapy*, Chapter 13, pp. 395–432 (1987).

Mendelson et al., "Expression and Rescue of a Nonselected Marker from an Integrated AA Vector," *Virology*, 166:154–165 (1988).

Simmons et al., "ICAM, an Adhesion Ligand of LFA–1, is Homologous to the Neural Cell Adhesion Molecule NCAM," *Nature*, 331:624–627 (1988).

Bodner et al., "The Pituitary–Specific Transcription Factor GHF–1 Is a Homeobox–Containing Protein," *Cell*, 55:505–518 (1988).

Ingraham et al., "A Tissue–Specific Transcription Factor Containing a Homeodomain Specifies a Pituitary Phenotype," *Cell*, 55:519–529 (1988).

Anderson et al., "A Conserved Sequence in the T–Cell Receptor β–Chain Promoter Region," *Proc. Nat'l Acad. Sci., USA*, 85:3551–3554 (1988).

Ohlsson et al., "A Beta–Cell–Specific Protein Binds to the Two Major Regulatory Sequences of the Insulin Gene Enhancer," *Proc. Nat'l Acad. Sci., USA*, 85:4228–4231 (1988).

Moss and Flexner, "Vaccinia Virus Expression Vectors," *Annals of the N.Y. Academy of Sciences*, 569:86–103 (1989).

Kit, "Recombinant–derived Modified–live Herpesvirus Vaccines," *Adv. Exp. Med. Biol.*, 251:219–236 (1989).

Samulski et al., "Helper–Free Stocks of Recombinant Adeno–Associated Viruses: Normal Integration Does Not Require Viral Gene Expression," *J. Virology*, 63(9):3822–3828 (1989).

Wu et al., "Targeting Genes: Delivery and Persistent Expression of a Foreign Gene Driven by Mammalian Regulatory Elements in Vivo," *J. Biol. Chem.*, 264(29):16985–16987 (1989).

Xiong et al., "Sindbis Virus: An Efficient, Broad Host Range Vector for Gene Expression in Animial Cells," *Science*, 243:1188–1191 (1989).

Sanchez and Holmegren, "Recombinant System for Overexpression of Cholera Toxin B Subunit in *Vibro cholerae* as a Basis for Vaccine Development," *Proc. Nat'l Acad. Sci., USA*, 86:481–485 (1989).

Swift et al., "Differential Requirements for Cell–Specific Elastase I Enhancer Domains in Transfected Cells and Transgenic Mice," *Genes & Development*, 3:687–696 (1989).

Benvenisty et al., "Separate Cis–Regulatory Elements Confer Expression of Phophoenolpyruvate Carboxykinase (GTP) Gene in Different Cell Lines," *Proc. Nat'l Acad. Sci., USA*, 86:1118–1122 (1989).

Fan and Maniatis, "Two Different Virus–Inducible Elements are Required for Human β–Interferon Gene Regulation," *EMBO J.*, 8(1):101–110 (1989).

Winoto and Baltimore, "A Novel, Inducible and T Cell–Specific Enhancer Located at the 3' End of the T Cell Receptor α Locus," *EMBO J.*, 8(3):729–733 (1989).

Camper and Tilghman, "Postnatal Repression of the α–Fetoprotein Gene is Enhancer Independent," *Genes & Development*, 3:537–546 (1989).

Karlsson et al., "Individual Protein–Binding Domains of the Insulin Gene Enhancer Positively Activate β–Cell–Specific Transcription," *Mol. Cell. Biol.*, 9:823–827 (1989).

Baldwin and Burden, "Muscle–Specific Gene Expression Controlled by a Regulatory Element Lacking a MyoD1–Binding Site," *Nature*, 341:716–720 (1989).

McDonnell et al., "Reconstitution of the Vitamin D–Responsive Osteocalcin Transcription Unit in *Saccharomyces cerevisiae*," *Mol. Cell. Biol.*, 9:3517–3523 (1989).

Van Assendelft et al., "The β–Globin Dominant Control Region Activates Homologous and Heterologous Promoters in a Tissue–Specific Manner," *Cell*, 56:969–977 (1989).

Feuerman et al., "Tissue–Specific Transcription of the Mouse α–Fetoprotein Gene Promoter Is Dependent on HFN–1," *Mol. Cell. Biol.*, 9:4204–4212 (1989).

Vaulont et al., "Analysis by Cell–Free Transcription of the Liver–Specific Pyruvate Kinase Gene Promoter," *Mol. Cell. Biol.*, 9:4409–4415 (1989).

Kerner et al., "Sequence Elements in the Human Osteocalcin Gene Confer Basal Activation and Inducible Response to Hormonal Vitamin $D_3$," *Proc. Nat'l Acad. Sci., USA*, 86:4455–4459 (1989).

Gross and Merrill, "Thymidine Kinase Synthesis is Repressed in Nonreplicating Muscle Cells a Translational Mechanism that Does not Affect the Polysomal Distribution of Thymidine Kinase mRNA," *Proc. Nat'l Acad. sci., USA*, 86:4987–4991 (1989).

Tussey and Felder, "Tissue–Specific Genetic Variation in the Level of Mouse Alcohol Dehydrogenase is Controlled Transcriptionally in Kidney and Posttranscriptionally in Liver," *Proc. Nat'l Acad. Sci., USA*, 86:5903–5907 (1989).

Forrester et al., "Molecular Analysis of the Human β–Globin Locus Activation Region," *Proc. Nat'l Acad. Sci., USA*, 86:5439–5443 (1989).

Flexner et al., "Attenuation and Immunogenicity in Primates of Vaccinia Virus Recombinants Expressing Human Interleukin–2," *Vaccine*, 8:17–21 (1990).

Kerr et al., "Antibody–Penicillin–V–Amidase Conjugates Kill Antigen–Positive Tumor Cells When Combined With Doxorubicin Phenoxyacetamide," *Cancer Immunol. Immunother.*, 31:202–206 (1990).

Markose et al., "Vitamin D–Mediated Modifications in Protein–DNA Interactions at Two Promoter Elements of the Osteoclacin Gene," *Proc. Nat'l Acad. Sci., USA*, 87:1701–1705 (1990).

Kriegler et al., "A Novel Form of TNF/Cachectin is a Cell Surface Cytotoxic Transmembrane Protein: Ramifications for the Complex Physiology of TNF," Cell, 53:45–53 (Apr. 8, 1988).

Kriegler et al., "Two Forms of Tumor Necrosis Factor/Cachectin and Their Roles in Local and Systemic Inflammatory Responses," *Growth Inhibitory and Cytotoxic Polypeptides, UCLA Symposium on Molecular and Cellular Biology*, vol. 103, pp. 203–222 (1989).

Randall et al., "Unity in Function in the Absence of Consensus in Sequence: Role of Leader Peptides in Export," *Science*, 243:1156–1159 (1989).

von Heijne, G. "A New Method for Predicting Signal Sequence Cleavage Sites," *Nucleic Acids Research*, 14(11):4683–4691 (1986).

Watson, M.E.E., "Compilation of Published Signal Sequences," *Nucleic Acids Research*, 12(13):5145–5164 (Jul., 1984).

Hock et al., "Retrovirus–mediated Transfer and Expression of Drug Resistance Genes in Human Haematopoietic Progenitor Cells," *Nature*, 320:275–277 (Mar. 20, 1986).

Culver et al., "Retroviral Mediated Gene Transfer into Cultured Lymphoid Cells as a Vehicle for Gene Therapy," *J. Cellular Biochemistry*, Supplement 12B, p. 171 (1988) (Abstract H105).

Guild et al., "Retroviral Transfer of a Murine cDNA for Multidrug Resistance Confers Pleiotropic Drug Resistance to Cells Without Prior Drug Selection," *Proc. Nat'l Acad. Sci., USA*, 85:1595–1599 (Mar., 1988).

Culliton, B.J., "Gene Test Begins," *Science*, 244:913 (May 26, 1989).

Culliton, B.J., "Gene Transfer Test: So Far, So Good," *Science*, 245:1325 (Sep. 22, 1989).

FIG. 11C

```
                                                   -76
                                                   ATG AGC ACT GAA AGC
                                                   Met Ser Thr Glu Ser

ATG ATC CGG GAC GTG GAG CTG GCC GAG GAG GCG CTC CCC AAG AAG ACA GGG
Met Ile Arg Asp Val Glu Leu Ala Glu Glu Ala Leu Pro Lys Lys Thr Gly

GGG CCC CAG GGC TCC AGG CGG TGC TTG TTC CTC AGC CTC TTC TCC TTC
Gly Pro Gln Gly Ser Arg Arg Cys Leu Phe Leu Ser Leu Phe Ser Phe

CTG ATC GTG GCA GGC GCC ACC ACG CTC TTC TGC CTG CTG CAC TTT GGA GTG
Leu Ile Val Ala Gly Ala Thr Thr Leu Phe Cys Leu Leu His Phe Gly Val

ATC GGC CCC CAG AGG GAA GAG TCC CCC AGG GAC CTC TCT CTA ATC AGC
Ile Gly Pro Gln Arg Glu Glu Ser Pro Arg Asp Leu Ser Leu Ile Ser
                         ▼ 1
CCT CTG GCC CAG GCA GTC AGA TCA TCT TCT CGA ACC CCG AGT GAC AAG CCT
Pro Leu Ala Gln Ala Val Arg Ser Ser Ser Arg Thr Pro Ser Asp Lys Pro

GTA GCC CAT GTT GTA GCA AAC CCT CAA GCT GAG GGG CAG CTC CAG TGG CTG
Val Ala His Val Val Ala Asn Pro Gln Ala Glu Gly Gln Leu Gln Trp Leu

AAC CGC CGG GCC AAT GCC CTC CTG GCC AAT GGC GTG GAG CTG AGA GAT AAC
Asn Arg Arg Ala Asn Ala Leu Leu Ala Asn Gly Val Glu Leu Arg Asp Asn

CAG CTG GTG GTG CCA TCA GAG GGC CTG TAC CTC ATC TAC TCC CAG GTC
Gln Leu Val Val Pro Ser Glu Gly Leu Tyr Leu Ile Tyr Ser Gln Val

CTC TTC AAG GGC CAA GGC TGC CCC TCC ACC CAT GTG CTC CTC ACC CAC ACC
Leu Phe Lys Gly Gln Gly Cys Pro Ser Thr His Val Leu Leu Thr His Thr

ATC AGC CGC ATC GCC GTC TCC TAC CAG ACC AAG GTC AAC CTC CTC TCT
Ile Ser Arg Ile Ala Val Ser Tyr Gln Thr Lys Val Asn Leu Leu Ser

GCC ATC AAG AGC CCC TGC CAG AGG GAG ACC CCA GAG GGG GCT GAG GCC AAG
Ala Ile Lys Ser Pro Cys Gln Arg Glu Thr Pro Glu Gly Ala Glu Ala Lys

CCC TGG TAT GAG CCC ATC TAT CTG GGA GGG GTC TTC CAG CTG GAG AAG GGT
Pro Trp Tyr Glu Pro Ile Tyr Leu Gly Gly Val Phe Gln Leu Glu Lys Gly

GAC CGA CTC AGC GCT GAG ATC AAT CGG CCC GAC TAT CTC GAC TTT GCC GAG
Asp Arg Leu Ser Ala Glu Ile Asn Arg Pro Asp Tyr Leu Asp Phe Ala Glu
                                            157
TCT GGG CAG GTC TAC TTT GGG ATC ATT GCC CTG
Ser Gly Gln Val Tyr Phe Gly Ile Ile Ala Leu
```

HUMAN TIL CELLS EXPRESSING RECOMBINANT TNF PROHORMONE

This application is a continuation of U.S. Ser. No. 08/237,783, filed Jun. 6, 1994, which is a division of U.S. Ser. No. 07/839,017, filed Feb. 18, 1992, now U.S. Pat. No. 5,324,655, which is a continuation of U.S. Ser. No. 07/488,706, filed Mar. 02, 1990, now abandoned, which is a continuation-in-part of U.S. Ser. No. 07/474,169, filed Feb. 02, 1990, now abandoned, which is a continuation-in-part of U.S. Ser. No. 07/426,986, filed Oct. 24, 1989, now abandoned.

TECHNICAL FIELD

The invention relates to the use of DNA recombinant technology to effect protein delivery to cells. In particular, it concerns the use of high and low titer recombinant retroviral vectors to deliver one or more desired protein(s) to cells, or a host organism that would benefit from the presence of the protein. A wide variety of proteins can be delivered including tumor necrosis factor, Interleukins, in particular Interleukin-2, and the protein that confers multiple drug resistance on cells.

BACKGROUND ART

So many approaches have been used to effect delivery of proteins, particularly proteins that have medically beneficial applications, to desired target cells that a survey of this field would be both inappropriate and unhelpful. It should be noted, however, that virtually all delivery systems presently employed address the problem of penetrating barriers to the circulatory system of the subject organism and do not address the problem of uptake by particular cells targeted for treatment with the protein. Thus, in the simplest form of ensuring penetration of these barriers, intravenous injection of a solution of an active ingredient, delivery of the protein merely results in the active ingredient circulating in the blood, but without provision for any special mechanism to ensure that the protein will find its way into the cytoplasm or nucleus of a cell that it is expected either to treat or to kill. While a specific cell may be targeted, e.g., through the use of antibody, penetration through cellular membranes is effected by whatever mechanism(s) is normally used by cells, or the appropriate site of treatment is necessarily extracellular.

It is, of course, established that viral particles are capable of introducing foreign nucleic acids and proteins into cells in the normal course of infection. Use of viral particles to transport genetic material into target mammalian cells for purposes of gene therapy appears to be the major approach now being followed to develop this technique. See, e.g., McCormick, D., Bio/Technolony (1985) 3:689–693. In addition, Lang, R. A., et al., Cell (1985) 43:531–542 were able to use a similar system with GM-CSF to induce autocrine growth in a murine blood-cell line. In the Lang work, a cDNA-encoding GM-CSF was inserted into a Moloney murine leukemia-based vector under control of the promoter/enhancer of the viral long-terminal repeat, and infectious, helper-free virus was produced by transfecting into the ψ psi-2-packaging cell line. The GMV virus produced was able to effect GM-CSF production in a hemopoietic cell line. This ability has not heretofore been used to transport designated protein drugs in an intact organism, however.

Retroviruses in particular have been used as vectors for foreign gene insertion, and the biology of retroviruses is, to a significant degree, understood: Retroviruses consist of a single stranded RNA genome encapsulated in a protein envelope. The genome itself, reading from the 5' to 3' end, contains a cap, a 5' untranslated region, a segment of RNA designated "ψ" which is necessary for the RNA to be packaged into protein -i.e., a packaging site, and then the coding sequences for several proteins -the retroviral core protein (gag); reverse transcriptase, to facilitate an intermediate stage consisting of a DNA transcript (pol) and the viral envelope or capsid protein (env), all followed by some 3' untranslated sequences. The three viral proteins are needed for the infectivity of the viral genome; the packaging site is needed to produce additional infective virus.

Retroviruses experience a "proviral" stage which contains a double-stranded cDNA copy of the protein-encoding region of the RNA. However, in this stage, the untranslated 3' and 5' regions are modified to obtain, at either end of this protein-encoding cDNA, a long terminal repeat (LTR) which provides the appropriate promoter and enhancer sequences to effect DNA transcription as well as transcription-terminating sequences at operable positions with respect to the coding portions.

In ordinary infection, the proviral double-stranded cDNA can be integrated into the host cell genome and from there effect the production of additional virus particles containing the RNA genome packaged in its protein capsule. For this procedure to take place, it is critical that the ψ packaging site be present in the provirus.

It has occurred to others that the protein encoding sequences of the retroviruses could be replaced with those for a desired protein so as to employ the expression systems of the virus when the modified virus infects host cells. See, e.g., U.S. Pat. No. 4,405,712 and Lang (supra). However, in order to achieve this, the modified viral genome requires a helper virus capable of synthesizing the capsid proteins and packaging the RNA transcripts of the foreign DNA.

Thus, for "gene therapy" the proviral DNA form is inserted into a suitable vector, replicated and packaged into viral envelopes with the aid of a helper virus. For a general review, see Anderson, W. F., Science (1984) 226:401–409; Coffin, J., "Genome Structure", in RNA Tumor Viruses, Vol 2, Weiss et al., eds, 2d ed, (1985), Cold Spring Harbor, N.Y.

The most commonly used retroviruses for study of gene therapy have been either the murine sarcoma virus (MSV) or the Moloney murine leukemia virus (MoMLV). (Mann, R., et al., Cell (1983) 33:153–159.) The proviral form of these retroviruses is isolated and inserted into more or less standard bacterial cloning vectors for amplification. The proviral insert, which contains the gag-, pol and env-encoding mRNA flanked by long terminal repeats containing the control sequences, along with a packaging site is then manipulated to replace the region containing the protein-encoding RNA with the desired foreign gene. If this DNA is transfected into host cells which have been infected with complete virus or with defective virus lacking only the packaging site, the RNA which is synthesized from the modified provirus is then packaged into virions for reinfection of another cell. This provides a mechanism for introduction of the DNA encoding the desired active ingredient or drug into the cell by infection.

There are two ways to go about this. In one approach, the modified proviral DNA is transfected into cells which bear an infection from the unmodified virus, co-residing in the cell. The normal viral vectors will synthesize the packaging materials and some of the mRNA produced by the modified provirus will be packaged in a manner analogous to the normal viral RNA and then can be used to infect target cell for the production of protein. Along with these commandeered viral envelopes, however, will be a certain number of repackaged normal viral RNAs which, if not separated from the "delivery truck" viruses simply cause additional virus infection in host cells infected with the products of this virion production round.

In a more useful approach, the provirus cloning vector containing the desired gene is used to transfect a cell which has been genetically modified to produce defective viral envelopes which contain no viral genomic RNA -in effect, empty delivery trucks. These cells are obtained by integration of the proviral form of a mutant retrovirus lacking the ψ packaging site, and several such cell lines are available in the art to all that request them. Two of these lines, designated ψ-1 or ψ-2 are extensively described in Mann, R., et al., *Cell* (1983) 33:153–159 (supra) and are made by transfecting host NIH 3T3 fibroblast cells with a plasmid containing MoMLV proviral inserts from which the ψ packaging site had been deleted. The ψ-2 cells apparently produce several empty viral envelopes per cell corresponding to the viral envelope of the native virus in the course of a generation. When these cells are transfected with proviral DNA containing both a foreign gene and the packaging site, ψ, they package the mRNA transcript from the proviral DNA containing the foreign gene into these empty envelopes to generate modified viruses which can infect any cells (murine in this case) which are normally hosts for MoMLV. It should be noted, however, that this recombinant, modified virus is defective in that it cannot cause the production of additional modified (or other) virions in, the cell it "infects". It is able to cause the production of the protein the gene encodes in the "infected" cell, but the infection cannot spread to additional cells because no additional virions are produced.

More useful than ψ-2 for the preparation of medicaments in the present invention are the ψ-AM lines, which are available from Cone, R. D., et al., *Proc Natl Acad Sci* (USA) (1984)81:6349–6353. These lines are also obtained by transfecting NIH 3T3 cells, but with a vector designated pMAV-ψ-. This vector also contains an insert of a defective provirus which lacks the ψ packaging site. However, pMAV-ψ- is a hybrid encoding the gag-pol sequences of MoMLV and envelope sequences derived from the amphotropic virus 4070A. The empty capsids produced by these cell lines package RNA transcripts of cotransfected modified proviral DNA to produce pseudo viruses which recognize and infect human, rat, and mouse cells.

It has recently been observed that retroviral electors carrying gag sequences exhibit higher titers than viruses that lack these sequences. Bender, et al., 1987, J. of Virology, 61(5):1639–1646. Such high titer viruses facilitate efficient infection of various cells/tissues that are targets for gene therapy. It is thought that the high titers of these viruses is related to the presence of gag region sequences that hithertofore were not thought to be involved in packaging of viral RNA into virions, and thus may allow for more efficient packaging. Regardless, such high titer retroviral vectors will have applications in gene therapy.

Thus, the art provides a system for moving genes into susceptible cells which has been, in the past, employed only for gene therapy or for generation of autocrine growth factors. These methods inevitably utilize an ex-vivo exposure of targeted cells to the retroviral vector, for example, in gene therapy, bone marrow cells are removed and treated, and then reimplanted In the present invention, an analogous system is mustered to deliver pharmaceuticals to target cells using conventional methods of administration to produce a highly dead-end, localized "infection".

DISCLOSURE OF THE INVENTION

The invention is directed to highly unusual pharmaceutical compositions and to methods for delivering active drugs to cells of organisms susceptible to viral infection. The target organisms are ordinarily vertebrates. In one embodiment, the pharmaceutical composition is composed of delivery viruses which contain envelope proteins capable of causing transient and nonreplicative infection of the cells in the subject organism to be treated with the drug. These pharmaceutical compositions are administered by injection into the blood stream or by localized injection into masses of undesirable cells such as tumor cells. Alternatively, cells susceptible to viral infection may be removed from the host organism infected with the appropriate virus and then returned to the host organism where they secrete the desired protein drug.

Thus, in one aspect, the invention relates to a drug delivery system which comprises a delivery retrovirus. The retrovirus has a "genome" comprising an RNA which encodes the desired active protein ingredient operably linked to control sequences which were derived from a retrovirus and to a ψ packaging site, and an envelope protein which is capable of effecting the infection of a target host cell with the virion, so that the target host cell alone is "infected", but unable to pass this infection to additional cells.

In a second aspect of the invention, a high titer retroviral drug delivery system is described wherein the high titer characteristics of the system are derived from the presence of gag sequences present in the vector. This vector is particularly useful for transforming cells or tissues that require high titers of virus, preferably tumor infiltrating lymphocytes or bone marrow cells.

A third object of the invention is the description of a high titer retroviral drug delivery system wherein one or more drugs are delivered and may include tumor necrosis factor, either the prohormone or hormone, interleukin-2, or proteins that confer drug resistance including the protein denoted, the multiple drug resistance protein (MDR).

A fourth object of the invention is the description of a retroviral drug delivery system wherein a retrovirus carries DNA that encodes a highly cell secretable form of tumor necrosis factor.

A fifth object of the invention relates to a method of administering one or more active protein(s) to a subject vertebrate host which comprises administering this drug delivery system either locally or systemically. Or, as alluded to above, the drug delivery system may be administered to a cell that is susceptible to viral infection, wherein the infection occurs in vitro, and the infected cell is then returned to the host organism where it produces the desired protein.

A sixth object of the invention relates to a method of delivering an active protein to vertebrate host cells that require high titers of retrovirus to effect infection of the cells thereby administering the protein to the cells and consequently to the vertebrate host.

A seventh object of the invention relates to materials and processes significant in the preparation of the above-described drug delivery system. These include proviral DNA comprising a DNA sequence encoding a desired active protein. The preferred molecules are those that can be used in cancer chemotherapy, such as tumor necrosis factor, IL-2, multiple drug resistant protein, etc. These sequences may be operably linked to control sequences derived from a retrovirus, including a packaging site, and flanked by retroviral-derived LTRs, or to homologous control sequences normally responsible for the expression of the protein drugs.

In another embodiment, the general method of the invention can also be carried out by implanting ψ- cells transfected with the proviral DNA of the previous paragraph, or cells infected with the pseudo virions they produce, to effect in situ production of the desired protein. Accordingly, the cotransfected ψ- cells and cells infected with the modified viruses they produce provide pharmaceutical compositions which are also aspects of the invention.

Also an aspect of the invention is a process to prepare the compositions thereof which comprises isolating the delivery virions produced by the foregoing ψ- packaging cells.

Culture dishes with G418-resistant colonies were overlaid with L929 cells at a density of $7.3 \times 10^4$ cells/cm2. When the cells attached, after 30 minutes, the medium was aspirated, and the cells were overlaid with DMEM supplemented with 10% FCS and 0.9% Noble agar. After incubation for 18–24 hours, clones surrounded by a lysed zone of L929 cells were isolated by cloning cylinders and expanded to mass culture.

Figure 6:
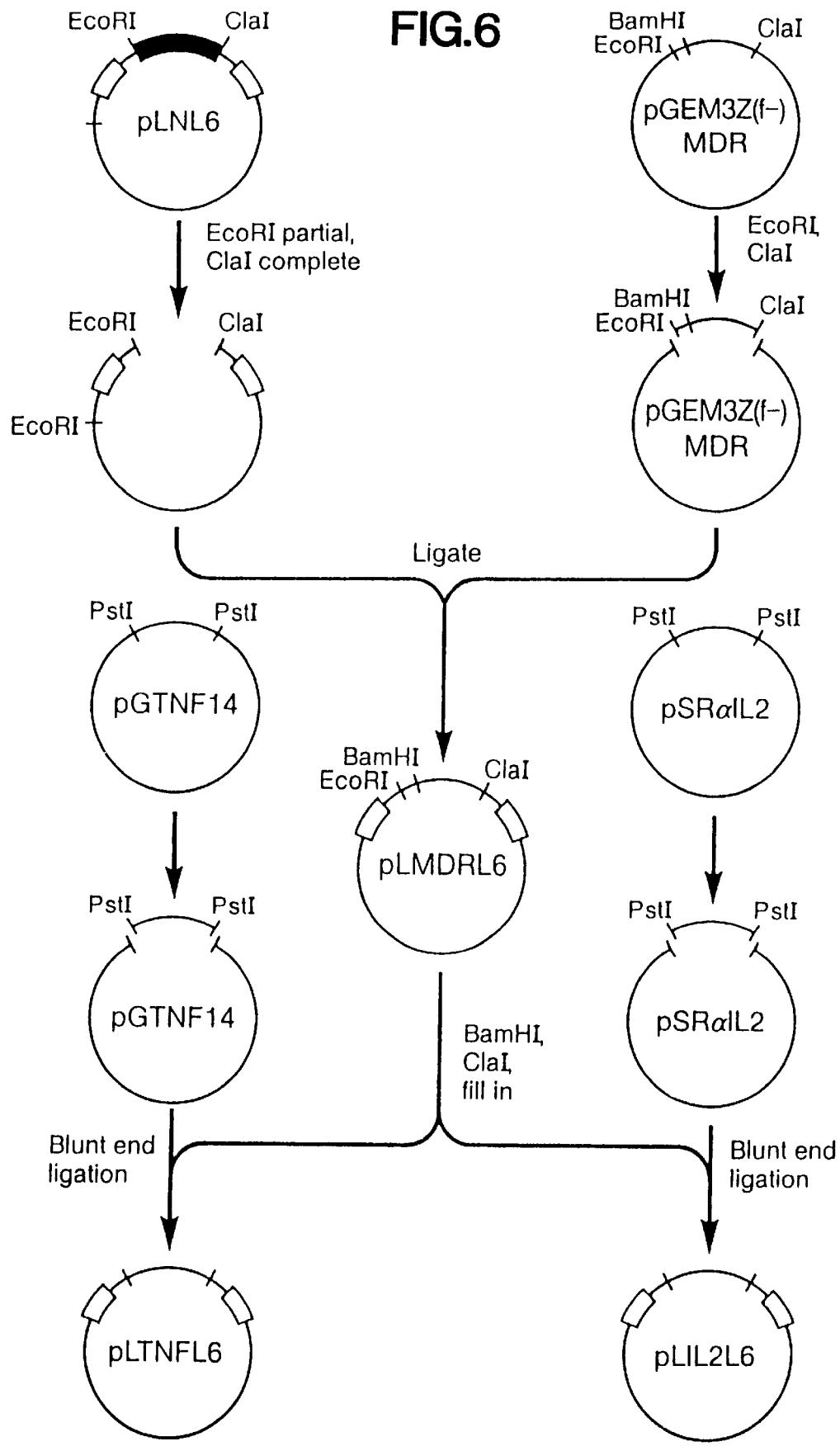

FIG. 6 shows the construction strategy for infective drug delivery retroviruses pLMDRL6, pLTNFL6 and pLIL-2L6.

Figure 7:
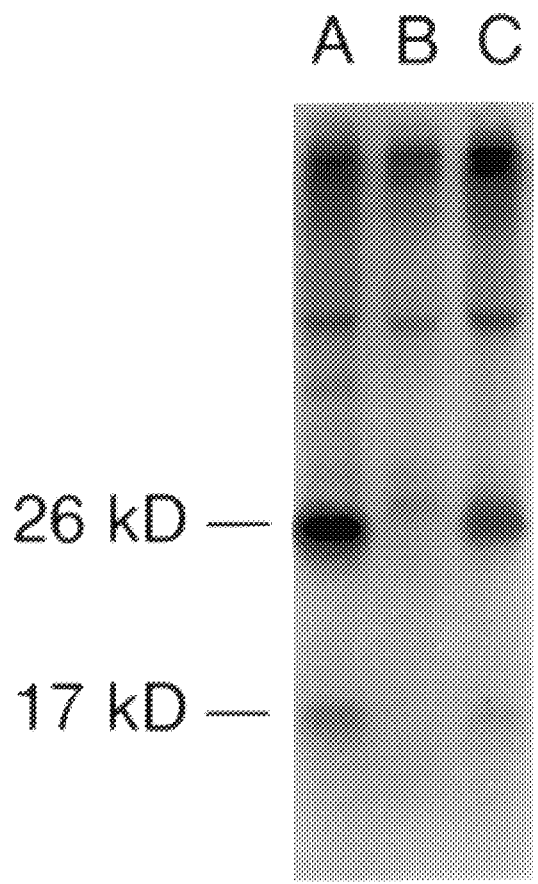

FIG. 7 shows immunoprecipitation analysis of cells transfected or infected with either the LTNFL6 plasmid or the high titer TNF retrovirus derived from LTNFL6. Lane A, PA317 cells transfected with the high titer retrovirus encoding both 26 kD and 17 kD TNF, LTNFL6; lane B, NIH 3T3 cells uninfected; and lane C, NIH 3T3 cells infected with the high titer TNF retrovirus, LTNFL6 clone 8 present in the cell culture supernatant of LTNFL6 transfected PA317 cells.

Figure 8:
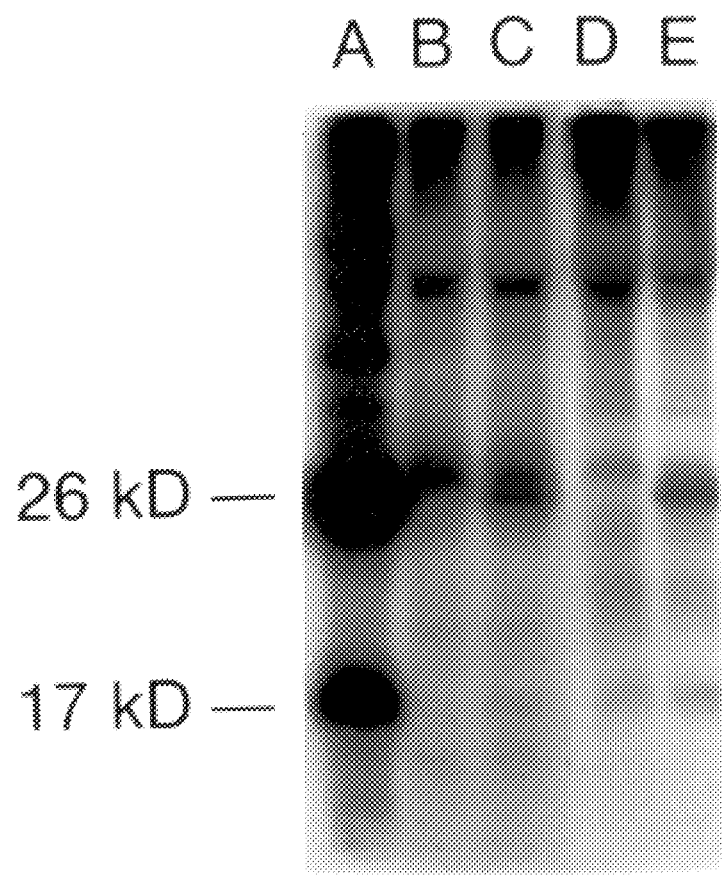

FIG. 8 shows immunoprecipitation analysis of 35S-cysteine labelled human melanoma cells infected with the TNF retrovirus LTNFL6. Lane A, PA317 cells transfected with LTNFL6; lanes B and C, uninfected and infected, respectively, NIH 3T3 cells with pLTNFL6 virus; and lanes D and E show uninfected and infected, respectively, human melanoma cells with the pLTNFL6 virus.

Figure 9:
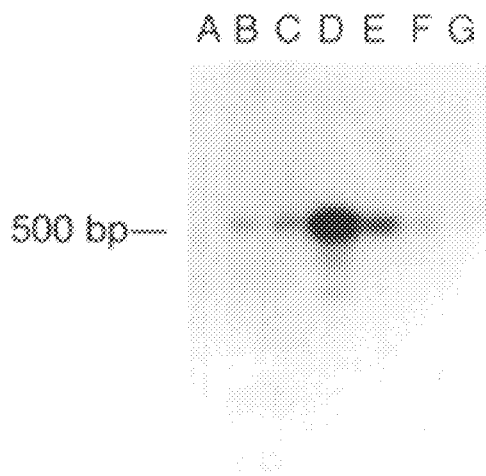
Figure 5A:
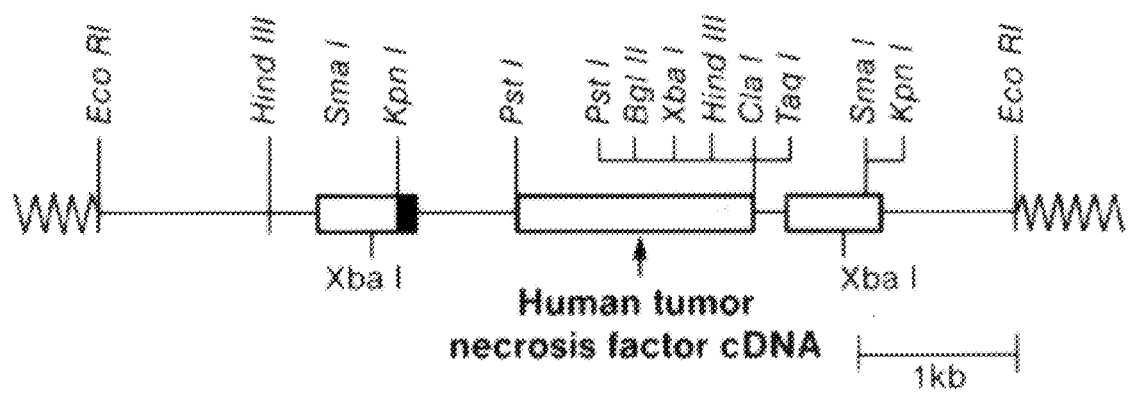
FIG. 5 shows the structure and bioactivity of the TNF retroviral genome. Lane A, restriction map of FVX TNF retroviral genome, and lane B, plaque assay of pFVXM transfected psi-am cells. The assay was performed as described below.
Figure 5B:
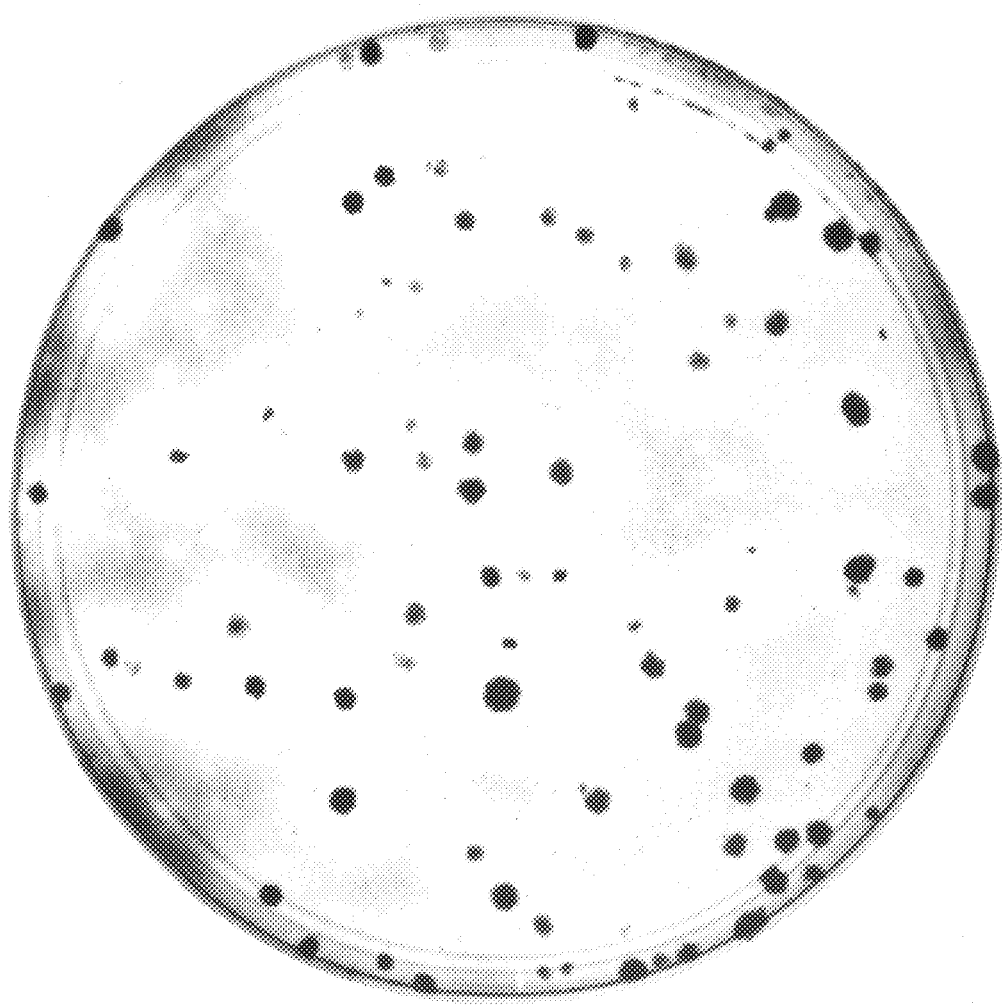

FIG. 9 shows PCR analysis of tumor infiltrating lymphocytes (TIL) infected with pLTNFL6 virus. Lane A, uninfected TIL; lanes B and C, infected human TIL; lane D PA317 transfected with pLTNFL6; and lanes E, F and G, 1:10, 1:100 and 1:1000 dilutions of same.

Figure 10:
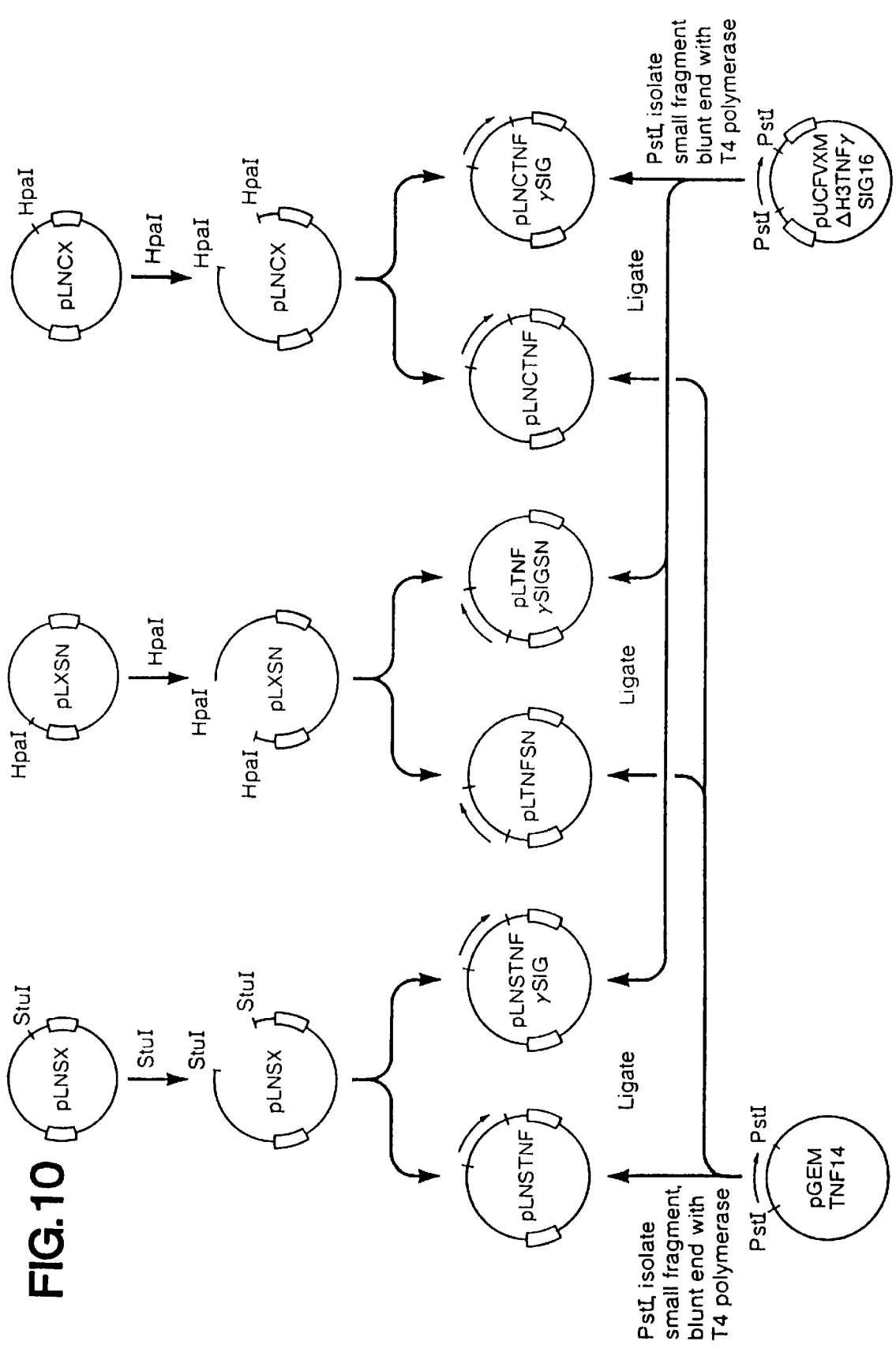

FIG. 10 shows the strategy for producing the two gene infective drug delivery retrovirus that encodes the dominate selectable marker for neomycin resistance and TNF.

Figure 11A:
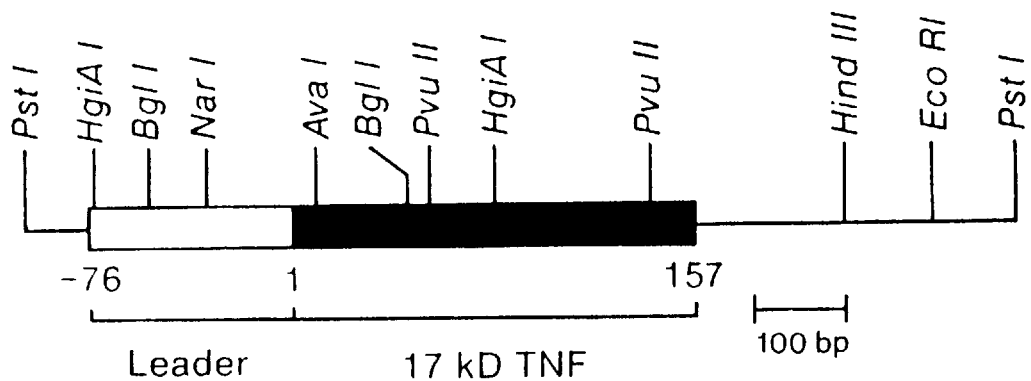
Figure 11B:
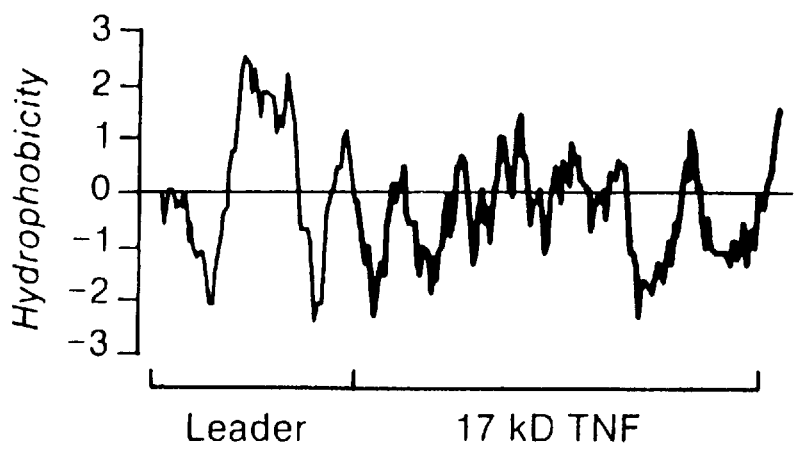

FIG. 11, panel A, shows the restriction map of the cDNA sequence that encodes 26 kD TNF. Panel B shows a hydrophobicity plot of 26 kD TNF, and panel C shows the DNA and amino acid sequences of the molecule.

Figure 12:
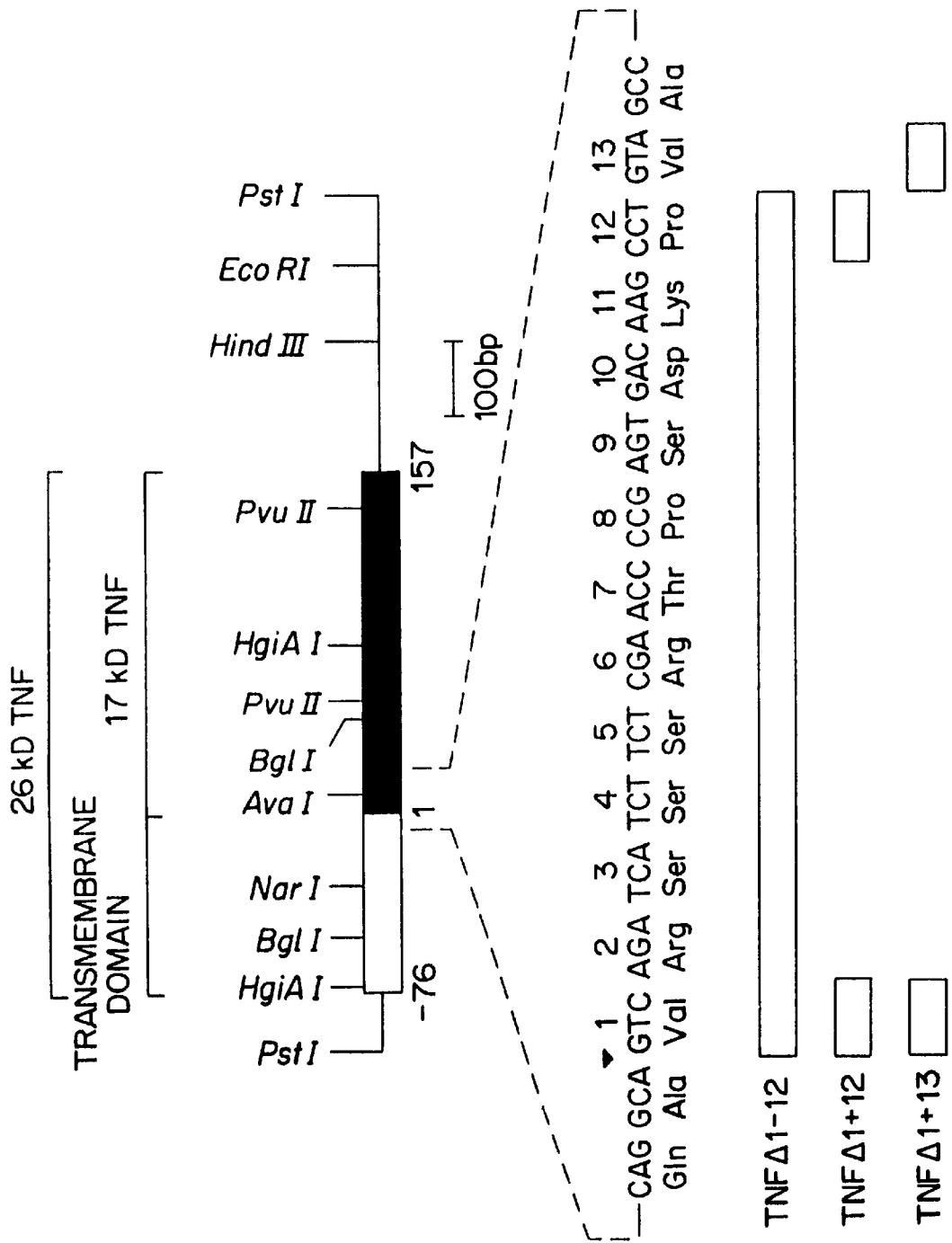

FIG. 12 shows a restriction map of the cDNA sequence that encodes 26 kD TNF and the regions of the molecule that were deleted to produce the various muteins.

Table I shows the cytotoxic activity of various TNF constructs.

MODES OF CARRYING OUT THE INVENTION

A. Definitions

As used herein, "drug delivery virion" refers to a modified retrovirus wherein the genome is an RNA which contains control sequences derived from retroviral nucleic acids operably linked to one or more coding sequences for an "active ingredient" protein(s). The genome is packaged in a protein envelope which is compatible with, and capable of causing "infection" with the contained genome in, a subject intended to be treated with the protein. The infection in this case extends only to the entry of the desired RNA into the cell and production of the protein; no additional infective virions are produced.

High titer "drug delivery virions", or "high titer retrovirus" is intended to refer to those vectors known in the art that allow production of retrovirus at titers at least $10^5$–$10^6$ cfu/ml. Examples of this type of virus are shown in Bender, et al., above.

Thus, "dead-end" infection describes a modified form of infection wherein the viral envelope facilitates the entry of the modified virus into the cytoplasm, and the contained genome is expressed, but no new virions are produced.

"Control sequences" refers to those nucleic acid sequences containing, for example, promoters and, often, enhancers which are necessary and sufficient for the production of the desired active protein ingredient by expression of the coding sequence operably linked to it.

In the case of the drug delivery retrovirions of the invention, the RNA genome and its proviral counterpart also includes the ψ packaging site.

"Tumor Necrosis Factor" or "TNF" as used herein refers to both native and recombinant forms of this known, mammalian cytokine. TNF has been referred to by other names in the literature, including "Cachectin" and "TNF-a". "Recombinant TNF" or "rTNF" refers to proteins, including muteins, produced by expression of recombinant DNA that have the same or substantially the same amino acid sequence as native TNF (or portions thereof), and retain both the in vitro and in vivo biological activity of TNF. The isolation and production of both native and recombinant mammalian TNF, including human TNF, is known in the art See, e.g., Carswell et al., 1975, *Proc. Nat'l Acad. Sci. USA*, 72: 3666–3670; Williamson et al., 1983, *Proc. Nat'l Acad. Sci. USA*, 80: 5397–5401; Wang et al., 1985, *Science*, 228:149–154; Beutler et al., 1985, *J. Exp. Med.*, 161:984;

Beutler et al., 1985, *Science*, 229: 869; Beutler et al., 1985, *Nature*, 316: 552; Pennicia et al., 1984, *Nature*, 312: 724; Aggarwal et al., 1985, *J. Biol. Chem.*, 260: 2345.

With regard to TNF, the terms "prohormone", and "mature hormone" have the following meanings. Prohormone refers to the 26 kd molecule, whereas mature hormone refers to the 17 kD molecule that results from the removal of a 76 amino acid leader sequence. The prohormone is known to be membrane bound and is not freely circulating, whereas the mature hormone is not membrane bound and is free to circulate. Thus, encompassed within the definition of TNF is the prohormone and mature hormones forms, and additionally, other forms of TNF wherein the 76 amino acid leader sequence is removed and replaced with another leader sequence that facilitates the secretion of the mature hormone. A number of leader sequences will perform this function, but preferred is the gamma interferon leader sequence, as described by Gray, P., et al., 1982, *Nature*, 295:503.

"Nucleic acid sequences" will sometimes be employed herein as a generic term covering both DNA and RNA fragments. As the materials of the invention include retroviral genomes and their proviral counterparts, particular functional sequences referred to will occur both in RNA and DNA form. The corresponding loci will be referred to interchangeably for their occurrences in both DNA and RNA, as it will be understood that in the ordinary course of infection, such functionalities are, indeed, interchangeable. For example, the ψ packaging site apparently is operable in the RNA genome to be packaged; however, the corresponding sequences occur in the proviral DNA. Similarly, promoter, enhancer, and terminator sequences occur, though in slightly different forms, in both the genomic RNA and proviral DNA forms. The interchangeability of these functionalities in the various phases of the viral life cycle is understood by those in the art, and accordingly, rather loose terminology in regard to DNA or RNA status is often used in referring to them. Specifically, sequences specified by a progression of bases should be understood to include these specific sequences and their complements, both in DNA and RNA forms.

The pharmaceutical compositions of the invention include the drug delivery virions produced by transfected intermediate cells which have been transformed with ψ- helper provirus and thus produce empty envelopes. For simplicity in referring to these cells used in the preparation of this composition, these cells will be referred to as "packaging" cells.

The resulting delivery virions can also be used to infect wild type cells in vitro, for example, as models for their ability to cause production of the desired protein in the target host These infected cells are referred to herein as "tester" cells.

B. General Description

The crucial intermediate in the preparation of the compositions of the invention is a proviral DNA vector containing the coding sequence for the protein drug(s) to be administered. The preferred embodiment protein drugs are those that are cytotoxic or cytostatic for tumor cells, preferably tumor necrosis factor (TNF) and interleukin-2 (IL-2), or drugs that can be utilized in an effective chemotherapeutic regime, such as multiple drug resistant protein. The DNA encoding such active protein ingredient may be obtained from any convenient source and, depending on the protein chosen, can be synthesized chemically, recovered from a cDNA library, isolated from genomic DNA, or otherwise obtained by means known in the art.

The proteins to be administered according to the method of the invention include any protein(s) which has a desired effect on an infected cell in the subject to be treated. Advantages of the drug delivery system of the invention are experienced especially when the protein operates within the cytoplasm of a target cell. For example, tumor necrosis factor (TNF) is capable of selectively killing tumor cells, but needs to transit the cell membrane to exert its effect. Other proteins, such as ribotoxins and the various colony-stimulating factors, also operate intracellularly.

It will be appreciated that retroviral vectors constructed to express two genes may include two proteins that have prophylactic or therapeutic value, or one gene could express a dominate selectable marker which would facilitate identifying cells transfected with the two gene construct. An example of a selectable marker would be resistance to G418 that is conferred on cells by the presence of the neomycin gene sequences.

The system of the invention is applicable also to materials whose function is carried out outside the target cells or which function by binding to receptors on the cell surface. In this case, however, the drug delivery virions are administered indirectly as an implant of transfected packaging cells or of tester cells which have been infected with the drug delivery virions. For example, tissue plasminogen activator or urokinase, which act in the bloodstream itself, directly on soluble enzymes in the blood, could be produced in situ by these implanted cells.

DNAs encoding the foregoing proteins are available in the art, and can be obtained bracketed with linker sequences for convenient manipulation, if desired. The nature of the delivery system is such that both genomic and cDNA sequences can be used, since introns can be processed in the environment transfected by the provirus. The protein drug can be encoded in the delivery virion to specify any form of the protein desired, for example, an active form, a mature form, a fused protein, a preprotein, or a preproprotein. In the example shown below, cDNA clones encoding TNF, IL-2, or MDR protein are used as the source of the coding sequence; however, clearly this is illustrative only, and any other desired coding sequence could also be employed. Further, it will be appreciated that two gene viruses can be constructed wherein one of the above molecules is expressed along with a dominant selectable marker such as resistance to G418.

The proviral transfer vector is obtained by isolation of an appropriate proviral form of a retrovirus such as the commonly used murine sarcoma virus (MSV), Moloney murine leukemia virus (MoMLV), Harvey sarcoma virus (HaSV), or a variety of other retroviruses. It is known that for certain target cells/tissues that they require a high titer of retrovirus to become infected. In these instances, the preferred retrovirus is one that includes the gag sequences, the so called gag+ vectors. Exemplary of such vectors are those described by Bender, et al., above, and Miller et al., in Current Communications in Molecular Biology—Viral Vectors, page 122, Cold Spring Harbor (eds. Gluzman, and Hughes, 1988). Since the proteins associated with the virion per se are deleted in the construction, even components derived from infectious retroviruses which cause disease in humans, such as hepatitis, HTLVI, and LAVI, could also be used, although it is not necessary to utilize such materials which, of course, have the potential for psychological resistance among the subjects to be treated. Further, infectivity host range could be altered by introducing a foreign viral envelope glycoprotein gene (i.e., rabies, VSV, etc.) into either the recombinant provirus or the packaging ψ type cell line.

The proviral form of the selected retrovirus is obtained by propagating the virus in tissue culture, isolating proviral DNA, cloning this proviral DNA into a lambda phage cloning vector, and propagating the recombinant vector in a susceptible bacterial host where the phage vector is integrated. The proviral DNA is excised and reisolated. The proviral DNA is then provided with suitable linkers and inserted into a bacterial cloning vector for amplification. Suitable bacterial cloning vectors include pBR322, pML, or vectors of the pUC series. These may need to be modified to eliminate or alter restriction sites and so forth, as is understood by those skilled in the art. The cloning vectors are restricted and then provided with inserts of the linkerframed proviral DNAs.

The native proviral DNA inserts contain the viral protein encoding sequences flanked by long terminal repeat (LTR) sequences and contain the packaging site adjacent one of the LTRs. These protein-encoding sequences between the packaging site and the other LTR are then eliminated by appropriate restriction and/or exonuclease digestion and replaced by linker or polylinker sequences. The appropriate sites may be already available in the intervening region, or if not, these can be obtained using site-directed mutagenesis, as is understood in the art.

After amplification, the vectors containing the modified provirions are cleaved with suitable restriction enzymes to open the vectors for insertion of the desired coding sequence. Since the control sequences, except for the packaging site, are in the long terminal repeats, insertion of a desired protein-encoding drug sequence into the linker places it in operable linkage with the controls. The resulting modified virion then becomes an expression system for the desired protein instead of for the viral proteins, and still retains a packaging site to permit this modified viral genome to be infective.

These drug delivery provirion DNAs are amplified and isolated using known techniques to provide a source of transfecting DNA for the $\psi$- packaging cells.

If desired, the inserted coding sequence in the modified virion, high or low titer virion, can also include a marker sequence. If a two gene retroviral vector is being used, one gene may encode neomycin resistance and thus confer resistance to G418. If a significant decrease in expression of the inserted sequence is observed then transfection of the $\psi$- packaging cells can be coincident with transformation with vectors containing a suitable marker, most appropriately the G418 resistance marker. Any suitable marker can, of course, be used, and such markers include, for example, Eco gpt conferring resistance to mycophenolic acid and DHFR sequences conferring methotrexate resistance.

The modified provirion, along with a marker plasmid, if necessary, is transfected into recipient packaging cells using standard transfection techniques such as calcium phosphate precipitation. The transformants are grown in culture appropriate to their particular cell type; the $\psi$- 3T3 cells illustrated below are cultured under conditions generally used for wild type 3T3 cells. Of course, an appropriate amount of a selective component of the medium, such as G418, is also included to select successful transformants.

The transformed packaging cells can be shown successfully to produce the proteins encoded by the inserted coding sequences in the modified virion by assessing the concentration of protein in the medium or cell lysate, as appropriate.

To obtain the packaged recombinant virions, the supernatant from the packaging cells is separated from the cells, for example, by using a 0.45 micron filter. The virus is obtained from the filtrate by, for example, high-speed centrifugation to harvest the viral particles or the filtrate is used per se. The concentrated viral particles or the filtrate are then formulated as pharmaceutical compositions.

In addition, the virion preparation can be assessed for competence to effect drug delivery to target cells by using a tester cell line, for example, the wild-type counterpart of the packaging cell line, which produces no empty viral capsules, or any cell line susceptible to infection by the virus and, preferably, also, to the protein produced by the recombinant virion. The amount of desired protein produced by this tester cell can be assessed, and, in the case of the appropriate cells, this assessment can be by the direct effect of the protein on the cells.

Both the packaging and tester cells can also be used as implants to provide a source of the protein drug in situ.

It is important to note that the LTRs contain most of the transcriptional control elements of retroviruses, including promoters and enhancers. Thus, while the inserted protein drug DNA sequences may be transcribed under the control of viral control elements, it is intended that also encompassed within the invention are viral vectors that have the viral control elements replaced with promoters/enhancers that normally regulate the transcription of a particular protein drug.

There are at least two basic approaches to obtain the expression of various protein drugs wherein the DNA sequences that encode the drugs are under the control of their normal control elements.

The first approach entails the substitution of the promoter, or the enhancer and promoter, or just the enhancer in the 3' retroviral LTR of the provirus with a promoter, or an enhancer and promoter, or an enhancer from a heterologous virus or cellular gene. Upon transfection, such a provirus would express itself from the wild type retroviral LTR. After virus rescue due to the nature of the retroviral life cycle, mutations of the U3 region of the 3' LTR are immortalized in the 5' LTR. Thus, the substitution of a heterologous expression element in the 3' LTR becomes immortalized in the 5' LTR of the newly integrated provirus. Thus, the expression of the exogenous gene inserted into the recombinant retrovirus is driven from the heterologous expression element originally resident in the 3' LTR of the recombinant provirus.

The second approach entails the deletion of the enhancer and promoter or merely the promoter resident in the 3' LTR by either restriction endonuclease digestion or through the application of site directed mutagenesis. When such a vector is rescued as an infectious retrovirus the resultant infectious provirus lacks expression elements in both the 5' and 3' LTRs. In this case, the expression defect is complemented by the insertion of an exogenous promoter or promoter/enhancer combination or a promoter enhancer combination plus an additional cis acting element (such as the U5 element of HTLV-1) between the LTRs of the recombinant provirus, just 5' to the gene to be expressed. Under these circumstances, after infection and gene transfer, the transferred gene is now subject to the regulatory controls imposed by the proximal promoter. Deletion of the expression elements in the LTRs insures that there is no interference from the LTR promoters.

Using the above approaches, retroviruses can be produced that have a variety of promoters, including the IL-2 promoter or the IL-2 receptor promoter driving the transcription of their corresponding proteins.

C. Utility and Administration

The drug delivery system of the invention is effective in the net result of transmitting protein drugs into cells where they may exert their effects. The transfer occurs by virtue of viral infection so it is merely necessary to juxtapose the drug delivery virions with the target cells. If the target cells are localized in, for example, a solid tumor the composition of the invention may be injected directly into the solid tumor. If the cells are, however, widely distributed such as in a leukemia or where, for example, red blood cells or bone marrow cells are needed to be targeted, systemic intravenous injection is required Alternatively, the drug may be delivered by infecting the cells in vitro and returning the infected cells to the host organism where they express the protein drug. The latter procedure will be particularly useful for gene therapy involving particular types of cells, including bone marrow and skin fibroblast cells.

Notable applications of the drug delivery systems described herein will involve the infection of tumor infiltrating lymphocytes, or other functionally similar cell types that act as vehicles for carrying the protein drugs to tumor cells, with retroviruses that encode a variety of protein drugs that are effective as anti-cancer agents. Preferably the protein drugs are IL-2 or TNF. Muteins of TNF that are membrane bound and cytotoxic are most preferred. For example, as will be described below the TNF deletion muteins of prohormone TNF Δ (1→12) and TNF Δ (1+12) are transmembrane proteins and thus are firmly affixed to the cell surface. Both are cytotoxic. Either of the muteins may be expressed in tumor infiltrating lymphocytes (TIL). If the cells selected are TILs, they will be highly cytotoxic because of their endogenous tumor cell cytotoxic activity, plus the cytotoxicity attributable to the TNF mutein. When used in this format, it will be appreciated that an added advantage associated with the TNF mutein Δ (1→12) is that because it is membrane bound and not released into the extra cellular environment there is little or no nonspecific cytotoxicity. A similar advantage is associated with the Δ (1+12) mutein. Although a molecule of about 17 kD is released from the mutein, it is not cytotoxic.

The virions are prepared for injection in typical ways suitable for administration of drugs by suspension in isotonic saline or other suitable pharmaceutical excipient as is known in the art.

Implantation of packaging or tester cells is conducted by formulating them into suitable compatible formulations, such as physiological saline, and directly injecting them into the desired location. The cells can also be formulated using encapsulation techniques. (See, e.g., U.S. Pat. No. 4,391,909.)

D. Standard Methods

Depending on the host cell used, transformation is done using standard techniques appropriate to such cells. The calcium treatment employing calcium chloride, as described by Cohen, S. N., *Proc. Natl. Acad. Sci.* (*USA*) (1972) 69:2110, or the $RbCl_2$ method described in Maniatis et al., *Molecular Cloning: A Laboratory Manual* (1982) Cold Spring Harbor Press, p. 254 was used for procaryotes or other cells which contain substantial cell wall barriers. For mammalian cells without such cell walls, the calcium phosphate precipitation method of Graham and Van der Eb, *Virology*, 1978, 52:546 is preferred.

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 λ of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol and resuspension in 10 mM Tris, 1 mM EDTA, pH 7.5. If desired, size separation of the cleaved fragments may be performed by polyacrylamide gel or agarose gel electrophoresis using standard techniques. A general description of size separations is found in *Methods in Enzymology*, 1980, 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 20° to 25° C. in 50 mM Tris pH 7.6, 50 mM NaCl, 6 mM $MgCl_2$, 6 mM DTT and 5–10 μM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

Synthetic oligonucleotides are prepared by the triester method of Matteucci et al., 1981, *J. Am. Chem. Soc.*, 103:3185, or using commercially available automated oligonucleotide synthesizers. Kinasing of single strands prior to annealing or for labelling is achieved using an excess, e.g., approximately 10 units of polynucleotide kinase to 0.1 nmole substrate in the presence of 50 mM Tris, pH 7.6, 10 mM MgCl2, 5 mM dithiothreitol, 1–2 mM ATP, 1.7 pmoles γ32P-ATP (2.9 mCi/mmole), 0.1 mM spermidine, 0.1 mM EDTA.

Ligations are performed in 15–30 λ volumes under the following standard conditions and temperatures: 20 mM Tris-Cl pH 7.5, 10 mM $MgCl_2$, 10 mM DTT, 33 μg/ml BSA, 10 mM-50 mM NaCl, and either 40 μM ATP, 0.01–0.02 (Weiss) units T4 DNA ligase at 4° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations (usually employing a 10–30 fold molar excess of linkers) are performed at 1 μM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 MM Tris, in the presence of $Na^+$ and $Mg^{+2}$ using about 1 unit of BAP per μg of vector at 60° C. for about 1 hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis is used. This is conducted using a synthetic primer oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered. Details of site specific mutation procedures are described below in specific examples.

More specifically, mutagenesis can be carried out using any number of procedures known in the art. These techniques are described by Smith, 1985, *Annual Review of Genetics*, 19:423, and modifications of some of the techniques are described in *Methods in Enzymology*, 154, part E, (eds.) Wu and Grossman (1987), chapters 17, 18, 19, and 20. The preferred procedure is a modification of the Gapped Duplex site-directed mutagenesis method. The general procedure is described by Kramer, et al., in chapter 17 of the *Methods in Enzymology*, above.

Conventional M13 mutagenesis methods involve annealing a short synthetic oligonucleotide to single stranded M13 DNA having a cloned target coding sequence that is sought to be mutagenized. The oligonucleotide is almost, but not entirely complementary to the target sequence and has at least one mispaired nucleotide. After the annealing reaction, the remaining portion of the single stranded DNA must be filled in to give heteroduplex DNA that can be transfected into a suitable host cell which allows for the expression of the mutation. In the gapped duplex method, a partial DNA duplex is constructed that has only the target region exposed, unlike the conventional methods which have the target region and the rest of the single stranded M13 DNA exposed. Like the conventional methods, a short oligonucleotide is annealed to the target region, and extended and ligated to produce a heteroduplex. However, because only a small portion of single-stranded DNA is available for hybridization in the gapped duplex method, the oligonucleotide does not anneal to undesired sites within the M13 genome. Further, this method has the additional advantage of introducing fewer errors during the formation of the heteroduplex since only a very small region of DNA on either side of the target region has to be filled in.

More specifically, the gapped duplex method involves cloning the target DNA sequence into an appropriate M13 phage that carries selectable markers, such as for example the stop codon amber mutation. The latter allows for negative selection in a host cell that cannot suppress the effects of the mutation. Preferably the phage is M13mp9 which contains two amber codons in critical phage genes. Thus, the sequence that encodes 26 kD TNF is cloned into M13mp9 amber+, and single stranded DNA is prepared therefrom using standard techniques. Next, double stranded replicative form DNA from M13 GAP, a genetically engineered M13 derivative that lacks the amber codons is cleaved with Hinc II restriction enzyme. The base sequence of M13 GAP is similar to M13mp18, which lacks both the amber codons and the sequence between base pairs 6172 and 6323. This deletion flanks the multiple cloning sites of the M13mp series and generates a unique Hinc II site. Gapped duplex DNA is formed, using standard DNA/DNA hybridization techniques, consisting of single stranded DNA having the amber codons, and a second strand of DNA from Hinc II digested M13 GAP lacking both the amber codons and the TNF coding sequences. Thus, the only portion of the gapped duplex that is exposed is the 26 kD TNF target sequence. The desired oligonucleotide is annealed to the gapped duplex DNA, and any remaining gaps filled in with DNA polymerase and the nicks sealed with DNA ligase to produce a heteroduplex. The latter is transfected, preferably into a mismatch repair deficient host, and mixed phage produced. From the mixed phage population, phage carrying unmutated 26 kD TNF DNA, which also have the amber mutations, can be selected against by infecting the mixed phage population into a host cell that cannot suppress the amber mutation. Clones can then be screened for phage that carry the desired TNF mutation.

Correct ligations for plasmid construction are confirmed by first transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al., 1969, *Proc. Natl. Acad. Sci.* (*USA*), 62:1159, optionally following chloramphenicol amplification (Clewell, D. B., 1972, *J. Bacteriol.*, 110:667). The isolated DNA is analyzed by restriction and/or sequenced by the dideoxy method of Sanger, F., et al., 1977, *Proc. Natl. Acad. Sci.* (*USA*), 74:5463 as further described by Messing et al., 1981, *Nucleic Acids Res.*, 9:309, or by the method of Maxam et al., 1980, *Methods in Enzymology*, 65:499.

Host strains used in cloning and expression herein are as follows:

For cloning and sequencing, *E. coli* strain HB101 was used as the host.

For M13 phage recombinants, *E. coli* strains susceptible to phage infection, such as *E.coli* K12 strain DG98 are employed. The DG98 strain has been deposited with ATCC 13 July 1984 and has accession number 1965.

E. Examples

The following examples are supplied herewith as illustrative of the invention and are not to be construed to limit the invention.

Example 1

Preparation of Modified Provirion Containing TNF

The coding sequence for human TNF was obtained from the clone pB11, a cDNA clone extensively described in U.S. Pat. No. 4,677,063, issued Jun. 30, 1987, and incorporated herein by reference. It may also be derived from clone pB11 also shown in U.S. Pat. No. 4,677,063. This clone is also on deposit at ATCC, ATCC#39894, deposited Oct. 15, 1984.

The plasmid pAW711, also there described, and deposited 8 Nov. 1984, ATCC#39918 can also be used as a source of TNF sequences.

The vector containing the retroviral control system in proviral form along with the packaging site is a derivative of pEVX; pEVX contains the LTRs and ψ site from MoMLV inserted into the EcoRI site of pML (Kriegler, M., et al., 1984, Cell, 38:483–491). pEVX was modified to eliminate a splice donor site by replacing a SmaI/BalI segment with a 978 bp SamI/SmaI fragment from the Harvey sarcoma virus (HaSV), which contains the 3' portion of the 5' LTR and the 5' portion of the HaSV genome. The resulting construct was digested completely with SstII and partially with BglII to obtain a 669 bp fragment lacking nonessential HaSV regions. This fragment was gel purified and religated to SmaI/BalI digested pEVX. The resulting vector pFVXM contains a polylinker between the LTR fragments derived from MoMLV and includes the packaging site from this virus, but lacks the splice donor site in the upstream LTR.

associated with the prohormone partially deleted, or replaced with another leader sequence that produces abundant amounts of the mature form of TNF. For example, this construct can be produced by removing the TNF Pst I fragment from pFVXMTNF and subcloning it into a suitable M13 vector, followed by mutagenesis with an appropriate oligonucleotide.

Thus, the DNA fragment encoding 26 kD TNF was excised from pFVXMTNF, and mutagenized after subcloning into M13mpl9 amber using the following oligonucleotide (Cetus number CP 383) that encodes the gamma interferon signal peptide:

5'-TCGAGAAGATGATCTGACGCCAAGAGAACCCAAAACGATGCAGAGCTGAAAAG-
CCAAGATATAACTTGTATATTTCATGGTGTCCTTTCCAGGGG-3' pFVXM, on deposit with the American Type Culture Collection, Accession No. 67,103

Figure 1:
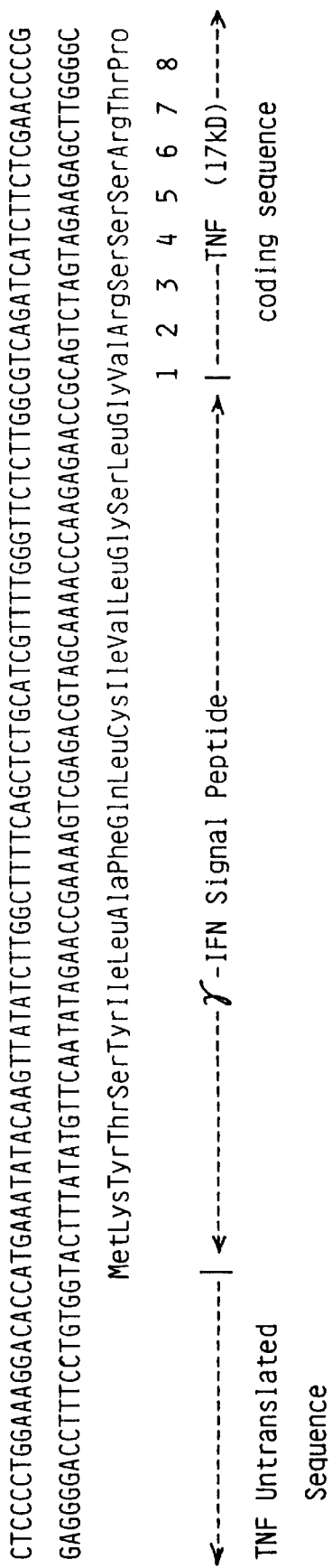
FIG. 1 shows the DNA sequence that encodes the gamma interferon signal peptide, and a portion of the DNA sequence that encodes mature TNF.

The pFVXM vector is amplified in E. coli strain HB101, and the plasmid DNA isolated. pB11 is likewise amplified in E. coli HB101 and reisolated as plasmid DNA. Both preparations of plasmid DNA are treated with Pst I (to excise the TNF-encoding region from pB11 and to open pFXVM in the polylinker region). Ligation of the fragments is carried out using standard conditions and the ligation mixture transformed into E. coli HB101 to Amp$^R$. Plasmid DNA was again isolated, and the correct orientation of the insert was established by restriction analysis. Recombinant plasmids The mutagenized construct containing the γ-interferon signal peptide was excised from the M13 vector, and cloned into a derivative of pFVXM termed pUC.FVXM δ HIII to produce pUC.FVXM δ HIII TNF γ sig. The latter construct is on deposit with the American Type Culture Collection with Accession Number 68121, and has been further deposited with Cetus Master Culture Collection, and is denoted 3688. The DNA that encodes the mature form of TNF with the γ-interferon signal peptide is shown in FIG. 1; only a portion of the DNA that encodes the 17 kD molecule is depicted. Shown below is the γ-interferon signal peptide linked to 17 kD.

```
                                                            TCC CCT GGA AAG GAC ACC

γ interferon    ─ ATG AAA TAT ACA AGT TAT ATC TTG GCT TTT CAG CTC TGC ATC GTT TTG GGT TCT CTT GGC
signal peptide    Met Lys Tyr Thr Ser Tyr Ile Leu Ala Phe Gln Leu Cys Ile Val Leu Gly Ser Leu Gly 1   2   3   4   5   6   7   8   9  10  11  12  13
17 kD TNF      ─ GTC AGA TCA TCT TCT CGA ACC CCG AGT GAC AAG CCT GTA GCC ...
                 Val Arg Ser Ser Ser Arg Thr Pro Ser Asp Lys Pro Val Ala
``` with the correct orientation of the TNF-encoding sequences are designated pFVXMTNF, and used to transfect appropriate packaging cells as described below. One such vector, pFVXMTNF6, is referred to more in detail below.

In a similar manner, for example, pFVXM may be digested with Pst I and ligated to DNA sequences encoding ricin A toxin, CSF-1, and urokinase, each provided with suitable Pst I linkers when needed. Further desirable, are vectors that encode leukocyte interferons, preferably hybrid interferon molecules as described by Weck et al., in Nucleic Acids Res., 1981, 9(22):6153, and in U.S. Pat. No. 4,678,751, to Goeddel D. V. N. Particularly preferred is the hybrid interferon designated LeIF-AD (Bgt). The resulting vectors are designated pFVXMRA, pFVXMCSF, pFVXMUK and pFVXMIF, respectively. The DNA sequence that encodes ricin A toxin is described in U.S. patent application, Ser. No. 06/837,583, while the cDNA sequences that encode mCSF, and urokinase are described in U.S. Pat. Nos. 4,847,201, 4,868,119, and EPO 92,182 and in Jacobs et al., 1986, DNA, 4(2):139–146, respectively.

It is will also be understood that the TNF sequence present in pFVXMTNF may have the 76 amino acid leader sequence pUC.FVXM δ HIII is similar to pFVXM with the exception that it lacks 1110 base pairs upstream of the 5'-LTR. Immunoprecipitation followed by SDS-PAGE of cell extracts, both lysates and supernatants obtained from NIH-3T3 cells transfected with pUC.FVXM δ HIII TNF γ sig revealed no detectable 26 kD TNF, but considerable amounts of the 17 kD molecule.

In addition to 17 kD or 26 kD TNF, retrovirions can be constructed that encode muteins of these molecules. The preferred muteins are those that maintain TNF in a membrane bound, cytotoxic form. More preferred are muteins that have deleted the first 12 amino acids, TNF A (1→12), or the first and twelfth amino acids, TNF δ (1+12), of the mature form of TNF (i.e. 17 kD TNF). In contrast to these two muteins, it was determined that TNF δ (1+13) is membrane bound but not cytotoxic. It was thus employed as a control in some of the examples presented below. The numbering of the amino acids corresponds to the amino acid sequence of the prohormone form of TNF shown in FIG. 11. The muteins can be generated using standard mutagenesis techniques and the following oligonucleotides to perform the mutagenesis.

CP 467: Δ (1 → 12)
5'-TAC AAC ATG GGC TAC TGC CTG GGC CAG AGG-3'
CP 472: screens Δ (1 → 12)
5'- TGG GCT ACT GCC TGG G-3'

CP 495: Δ VAL 1
5'-TCG AGA AGA TGA TCT TGC CTG GGC CAG AGG-3'
CP 496: screens Δ VAL 1
5'- TGA TCT TGC CTG-3'

CP 497: Δ PRO 12
5'-TAC AAC ATG GGC TAC CTT GTC ACT CGG GGT-3'
CP 498: screens Δ PRO 12
5'- GGC TAC CTT GTC-3'

CP 499: Δ VAL 13
5'-TGC TAC AAC ATG GGC AGG CTT GTC ACT CGG-3'
CP 500: screens Δ 13
5'- ATG GGC AGG CTT-3'

Briefly, the oligonucleotides are kinased using the following reaction solution and conditions: 3 μl 10×KB buffer, 3 λ 10 mM rATP (1:10 dilution of 0.1M rATP stock), 2λ mutagenic oligonucleotide (100 pmole/λ), 21 λ H₂O, and 1 λ polynucleotide kinase (10 units/λ). The reaction is run at 37° C. for 45 minutes, and then at 65°–68° C. for 5 minutes. Next, 24 λ of the kinased oligonucleotide is diluted with 56 λ of H₂O to give 2 pmole/λ.

The gapped duplex is formed as described below, followed by annealing the oligonucleotides. The following reagents are combined in a total volume of 40 λ:8 λ 5×GDB buffer, 0.50 pmole ssDNA, and 0.10 pmole Hinc II linearized M13 GAP RF DNA. 10 λ is removed for future use, and the remaining 30 λ is treated sequentially as follows: 100° C. for 3 minutes, 65° C. for 5 minutes, followed by cooling to room temperature for 30 minutes, and then placing the reaction mixture on ice. Next, 10 λ of gapped duplex and 10 λ of control ungapped material is subject to electrophoresis on a agarose gel to check gapped duplex formation. Assuming the gel shows the presence of a third band, the gapped duplex has formed and the kinased oligonucleotides can be annealed to the duplex by combining 16 λ of gapped duplex reaction mixture, and 4 λ of diluted kinased oligonucleotide, and heating the mixture to 65° C. for 3 minutes, followed by cooling to room temperature for 20 minutes.

To produce TNF δ (1+12) and TNF δ (1+13), two kinased oligonucleotides were annealed to the same gapped duplex. CP 495, CP 497, and CP 499 were kinased as before, but diluted to a concentration of 4 pmole/λ. To produce TNF δ (1+12), 2 λ of CP 495 and 2 λ of CP 497 was added to 16 λ of gapped duplex and annealed. To produce TNF δ (1+13), 2 λ of CP 495 and 2 λ of CP 499 was added to 16 λ of gapped duplex and annealed.

The heteroduplex is completed by the appropriate extension and ligation reactions consisting of combining the following reagents in a total volume of 40λ:10 λ gapped duplex and primer, 4λ 10×PEL buffer, 4 λ dNTP's (0.25 mM solution made from 10 mM stocks, 3 λ ATP (10 λ of 0.1M ATP stock+1490 λ H₂O=0.662 mM), 17 λ H₂O, 1 λ Klenow (5 u/λ), and 1 λ T4 DNA ligase (0.6 Weiss u/λ, diluted stock with 1×PEL). The reaction is conducted at 16° C. for 2 hours, followed by transformation of 10 λ of the extension/ligation mixture into 200 λ of thawed competent HB2154 cells. The cells are kept at 0° C. for 30 minutes, and then 42° C. for 1.5 minutes, followed by plating various volumes of the transformation mix (e.g., 50λ, 10 λ, etc.) with 100 λ of fresh overnight culture of HB2151 cells+3.0 λ of soft agar.

The resulting plaques are screened using the plaque hybridization procedure. While a variety of such procedures are known, a description of the preferred procedure follows. Plates are replicated onto duplicate nitrocellulose filter papers.(S & S type BA-85) and the DNA fixed to the filter by sequential treatment for 5 minutes with 0.5N NaOH plus 1.5M NaCl; 1.0M NaCl plus 0.5M Tris-HCl pH 7.4; and 2×SSC (standard saline citrate). Filters are air dried and baked at 80° C. for 2 hours, in vacuo.

The duplicate filters are prehybridized at 55° C. for 2 hours with 10 ml per filter of DNA hybridization buffer, 5×SSC, pH 7.0, 5×Denhardt's solution (polyvinylpyrrolidone, plus Ficoll and bovine serum albumin; 1×0.02% of each), 50 mM sodium phosphate buffer at pH 7.0, 5 mM EDTA, 0.1% SDS, and 100 μg/ml salmon sperm DNA. The prehybridization buffer is removed and the samples hybridized with the appropriate kinased probe, that is to say kinased oligonucleotides as shown above, under conditions which depend on the stringency desired. About 2×10⁶ cpm/ml total is used. Typical moderately stringent conditions employ a temperature of 42° C. plus 50% formamide for 24–36 hours with 1–5 ml/filter of DNA hybridization buffer containing probe. For higher stringencies high temperatures and shorter times are employed. The preferred hybridization conditions consists of hybridizing the probes to the filters in 5×SSC, Denhardt's solution, 50 mM NaPO4, pH 7.0, 5 mM EDTA, 0.1% SDS, and 100 μg/ml salmon sperm DNA at 100 below the TM of the oligonucleotide used to do the screening. Next, the filters are washed twice, 30 minutes each wash, at room temperature with 2×SSC, 0.1% SDS, then washed once with 2×SSC and 0.1% SDS at 5° C. below the TM of the oligonucleotide used to screen, and air dried. Finally, the filters are autoradiographed at -70° C. for 36 hours. Autoradiography reveals those plaques containing the virus that carries the muteins of interest.

To screen for double mutants, one set of filters were probed with one screening oligonucleotide and a replicate set of filters (lifted from the same plates) were probed with the other appropriate screening oligonucleotide. The resultant autoradiographs were aligned and plaques that hybridized to both screening oligonucleotides were picked and sequenced.

The mutagenized constructs containing the various TNF muteins are excised from the M13 vectors, and cloned into one of several possible vectors to produce infectious retrovirions. Exemplary vectors include pFVXM, pUCFVXM δ HIII, high titer retroviral vectors, preferably pLNL6 described in Example 5, or vectors that yield two gene retrovirions, preferably pLNSX, pLXSN and pLNCX as described in Example 7. The latter three vectors all carry the neomycin gene sequences.

Example 2

Production of Drug Delivery Retrovirions that encode TNF

The pFVXM-TNF prepared as described in Example 1 (10 μg) is mixed with 1 μg of pSV2-NEO (Southern et al., 1982, *J. Mol. Appl. Gen.*, 1:327–341), which contains the marker sequences conferring resistance to the antibiotic G418. Transfection was conducted using a modification of the calcium phosphate method of Wigler, et al., 1978, *Cell*, 14:725. Briefly, 10 μg of carrier DNA, diluted with sterile 1 mM Tris, pH 8.1, 0.1 mM EDTA, was added to 100 mm Petri dishes, along with plasmid DNA, 50–1,000 ng per 100 mm Petri dish, followed by the addition of 2.5M CaCl₂. This mixture was agitated thoroughly to assure uniform suspension, and an equal volume of 2×HEPES (N-2-hydroxyethyl diperazine N'-2-ethanesulfonic acid) buffered saline, pH 7.1, was added. This mixture was also agitated to assure uniform suspension, after which a precipitate was allowed to form. Thirty minutes later, 1 ml of the suspension was added to psi AM cells in 100 mm Petri dishes containing 10 ml of DMEM supplemented with 10% fetal calf serum. The cultures were incubated at 37° C. for 16 hours and subsequently the medium replaced with fresh growth medium. Next, the growth medium was replaced again with fresh medium, but supplemented with 400 μg/ml of G418, obtained from Gibco. After an initial growth period, the cells were grown on selection medium containing 400 μg/ml G418 and resistant colonies were picked, and transferred to 24-well tissue culture dishes for testing for TNF production.

The cellular proteins were labelled with either $^{35}$S-cysteine or $^{35}$S-methionine. The cells were first cultured on DMEM lacking cysteine or methionine, but containing 5% dialyzed fetal calf serum, for 30 minutes at 37° C. to effect cysteine or methionine starvation. One hundred μCi of $^{35}$S-cysteine or $^{35}$S-methionine having a specific activity of approximately 400 Ci/mmol was added and the cells further incubated for 2 hours at 37° C. The supernatant was removed and saved. The cells were lysed with lysis buffer and the lysate supernatant was also recovered by centrifugation. Both the clarified lysate and culture supernatant were tested for the presence of TNF as follows.

Polyclonal antisera to recombinant TNF prepared in rabbits were added to each test material in a centrifuge tube and incubated at 4° C. for 1 hour with shaking. This was followed by the addition of a 50% suspension (v/v) of protein A attached to Sepharose CL4B and followed by incubation at 4° C. for 30 minutes.

The beads were pelleted in a microfuge and washed. The precipitated material was removed from the beads by boiling in SDS. The solubilized TNF-containing solutions were loaded onto 12.5% polyacrylamide gel for electrophoresis and the proteins were fixed and stained as well as read by autoradiography. The results are shown in FIGS. 2 and 3.

Figure 2:
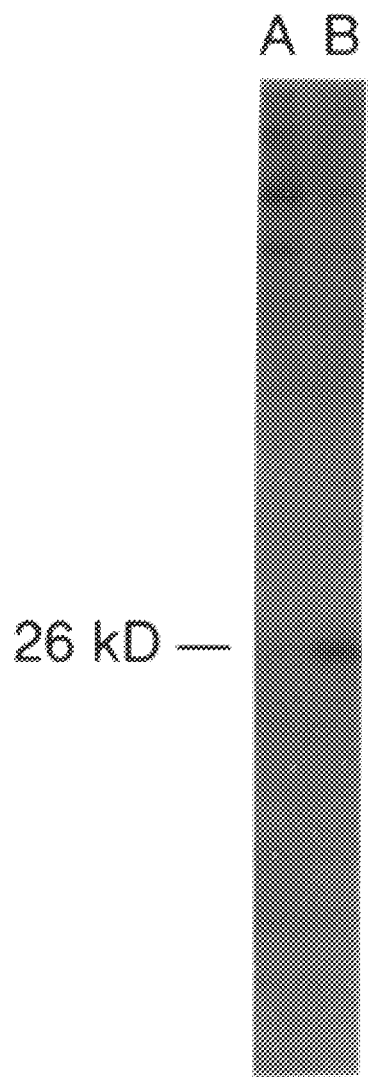
FIG. 2 shows immunoprecipitation analysis of 35S-methionine labelled TNF encoded by pFVX TNF. Lane A, untransfected cells and lane B, cells transfected with pFVX TNF. Methionine labels only the 26 kD precursor, not the 17 kD "mature" form (as predicted from the amino acid sequence).

FIG. 2 shows the results of labelling with $^{35}$S-methionine. Label appears only in the leader sequence of the 26 kD unprocessed protein in the lysate; no label is present in the mature, 17 kD, secreted form (which does not contain methionine residues).

Figure 3:
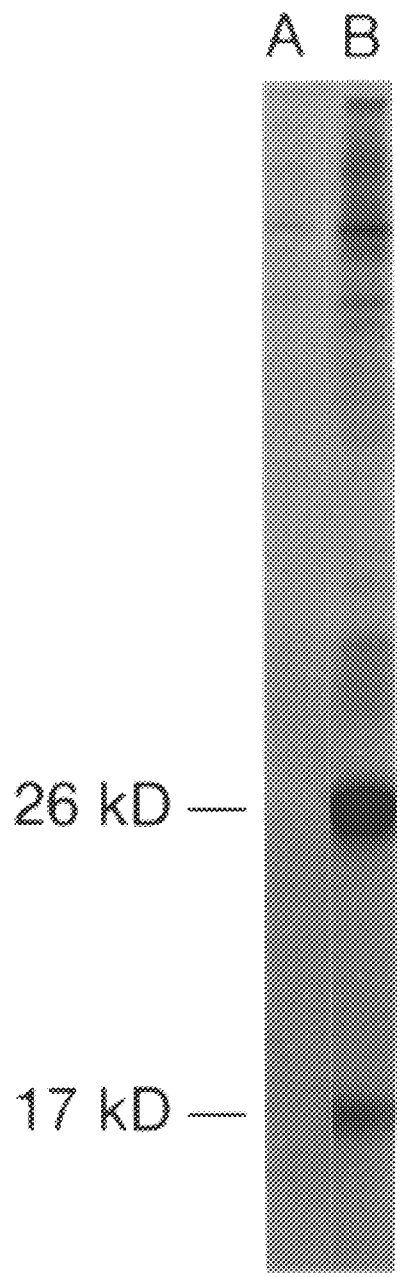
FIG. 3 shows immunoprecipitation analysis of 35S-cysteine labelled TNF encoded by pFVX TNF. Lane A, untransfected cells and lane B, cells transfected with pFVX TNF. Cysteine labels both the 26 kD precursor and the 17 kD mature form (as predicted from the amino acid sequence).
Figure 4:
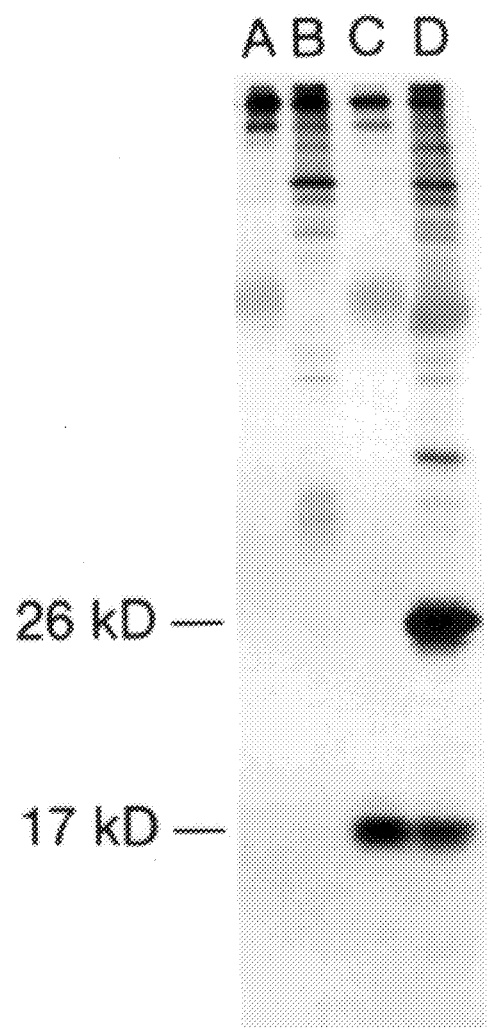
FIG. 4 shows immunoprecipitation analysis of TNF retrovirus infected 35S-cysteine labelled 3T3 cells. Lane A, supernatant derived from NIH 3T3 cells; lane B, cytoplasmic lysates of NIH 3T3 cells; lane C supernatant derived from cells infected with the FVX TNF retrovirus (TNF-V); and lane D, cytoplasmic lysates derived from cells infected with same. Note that the 26 kD form of TNF is found in the cytoplasmic extracts and is not secreted, whereas the 17 kD "mature" or secreted form is found in both the cytoplasmic extracts and the supernatants.

FIG. 3 shows the results of $^{35}$S-cysteine labelling; both the unprocessed and mature forms are labelled, as expected.

Cell supernatants were also assayed for TNF using the L-929 assay below. The ability of these supernatants to show TNF activity was completely destroyed by preincubation with the rabbit anti-TNF antisera.

Example 3

Recovery of Drug Delivery Virions

The supernatants from the cells of Example 2 which secrete TNF into the medium were filtered through 0.45 micron Millipore filters to ensure that no cells were transferred. Similarly, one can centrifuge the supernatants at 3,000×g to pellet any cells or cellular debris. The supernatant contains the recombinant virion designated TNF-V.

Example 4

Dead-End Infection of Tester Cells

The TNF-V prepared in Example 2 was used to infect $1\times10^5$ NIH 3T3 or RAT2 cells by incubation with 4 μg/ml of polybrene at 37° C. overnight in a $CO_2$ incubator. Cell supernatants and lysates were analyzed for TNF production using $^{35}S$-cysteine labelling, immunoprecipitation and radioautography exactly as described above in Example 2. The results for infected cells are shown in FIG. 4. Both the 17 kD and 26 kD forms of TNF contain label.

Supernatant from these cells also showed TNF activity using the L-929 cytotoxicity assay, which activity was removed by incubation with rabbit anti-TNF antisera.

Assay for TNF Activity

FIG. 5 shows the structure and bioactivity of the TNF retroviral genome. Lane A, restriction map of FVX TNF retroviral genome, and lane B, plaque assay of pFVXM transfected psi-am cells. To assay biological activity of the TNF, the L-929 assay system was used. The L-929 cells are prepared overnight as monolayers in microtiter plates. The test samples are diluted 2-fold across the plate, UV irradiated, and then added onto the prepared cell monolayers. The culture media in the wells are then brought to 1 μg/ml actinomycin D. The plates are allowed to incubate 18 hr at 37° C. and the plates are scored visually under the microscope. Each well is given a 25, 50, 75 or 100% mark signifying the extent of cell death in the well. One unit of TNF activity is defined as the reciprocal of the dilution at which 50% killing occurs.

In addition, a more sensitive version of this assay was developed that monitors the release of $^{35}S$ labelled peptides from prelabelled cells, when treated with the test sample and actinomycin D. This version of the assay can be used to quantitate potency, e.g., to evaluate the relative potency of oocyte translated material. Briefly, actively growing L-929 cultures are labelled with $^{35}S$ methionine (200 μCi/ml) for 3 hours in methionine-free media supplemented with 2% dialyzed fetal calf serum. The cells are then washed and plated into 96 well plates, incubated overnight, and treated the next day with 2-fold dilutions of test samples and 1 μg/ml actinomycin D. The cultures were then incubated at 37° C. for 18 hours. One hundred λ supernatant aliquots from each well were then transferred onto another 96 well plate, acid (TCA) precipitated, and harvested onto glass fiber filters. The filters were washed with 95% ethanol, dried and counted. An $NP_{40}$ detergent control is included in every assay to measure maximum release of radioactivity from the cells. The percent $^{35}S$ release is then calculated by the ratio of the difference in count between the treated cells and untreated controls divided by the difference between $NP_{40}$ treated cells and untreated controls, i.e., by the ratio:

$$\% \text{ release} = \frac{\text{sample} - \text{cell control}}{NP_{40} - \text{cell control}} \times 100.$$

Higher TNF potency results in higher values of this ratio.

Example 5

Preparation of Modified High Titer Provirion Containing Protein

Drug Encoding Sequences

The coding sequences for human TNF, IL-2, and MDR were cloned into the high titer retroviral vector, pLNL6. The vector is described by Bender, et al., 1987, *J. of Virol.*, 61(5): 1639–1646. FIG. 6 shows the construction strategy for infective drug delivery retroviruses pLMDRL6, pLTNFL6 and pLIL-2L6.

Isolation of MDR Sequence/pLMDRL6

The initial step in the production of pLMDRL6 was the isolation of the DNA sequence that encodes MDR. The DNA sequence that encodes MDR is described in U.S. patent application, Ser. Nos. 892,575, and 845,610, and also in PCT/US87/00758. The full length cDNA sequence that encodes the MDR protein is shown in Table 5 of the PCT application. It was initially cloned into a commercially available vector, pGEM3Z(f-), as a Xba I-Cla I fragment. To accomplish this, Cla I-Hind III linker adaptors were ligated to the Cla I-Xba I MDR fragment. This construct was then ligated into the Xba I-Hind III site of pGEM3Z(f-) resulting in pGEM3Z(f-)MDR.

Using pGEM3Z(f-)MDR, the high titer vector pLMDRL6 was produced as follows. Fifty μg of pGEM3Z(f-)MDR was digested with 200 units of Cla I (New England Bio Labs) in Tris-acetate buffer consisting of 33 mM Tris-acetate, pH 7.9 (66 mM potassium acetate, 10 mM magnesium acetate, 0.5 mM dithiothreitol) in a total volume of 500 λ. The reaction was conducted at 37° C. for 60 minutes after which the DNA was phenol extracted and ethanol precipitated in an ethanol solution containing 2.5M ammonia acetate. The precipitate was resuspended in 400 λ of water and the Cla I digested pGEM3Zf(-)MDR subjected to a second digestion with Eco RI as follows.

To the 450 λ of ethanol precipitated and resuspended material was added 50 λ of 10×Tris acetate buffer and 38 units of Eco RI (New England Bio Labs). The mixture was incubated at 37° C. for 60 minutes, and the material phenol extracted, and ethanol precipitated as described above. The ethanol precipitate was resuspended in 100 λ of Tris-EDTA buffer (10 mM Tris (pH 8.0) 1 mM EDTA). A sample was prepared for electrophoresis by adding 20 λ of loading buffer consisting of 0.25% bromophenol blue, 0.25% xylene cyanol (15% Ficol) type 400 in water. The sample was electrophoresed in a 1% agarose preparative gel in Tris acetate buffer consisting of 40 mM Tris-acetate, pH 8.0 (2 mM EDTA) electrophoresis buffer.

Following electrophoresis, a gel fragment containing the 4.2 kb MDR Eco RI-Cla I fragment was excised from the gel, and the DNA isolated using standard glass bead purification techniques.

Preparation of pLMDRL6

The high titer retrovirus vector, pLNL6 was prepared to receive the 4.2 kb MDR Eco RI-Cla I fragment as follows. The procedures employed were similar to those used to insert the fragment into the pGEM3Z(f-) vector. Briefly, 50 μg of pLNL6 was digested with Cla I and subsequently with 38 units of Eco RI. This produced a 4.7 kb Eco RI-Cla I fragment which was isolated using standard electrophoresis techniques. Next, the 4.2 kb MDR Eco RI-Cla I fragment and the 4.7 kb Eco RI-Cla I pLNL6 fragment were ligated to produce the high titer MDR expression vector, pLMDRL6. The procedure consisted of ligating 1 μg of the MDR Eco RI-Cla I fragment to 1 μg of the 4.7 kb Eco RI-Cla I pLNL6 fragment in a total volume of 25 λ in Tris-acetate buffer containing 4 mM ATP and 400 units T4 DNA ligase (New England Bio Labs). The reaction was run for 16 hours at 4° C., after which the ligation mixture was diluted 1:4 with TE buffer. Five λ of this mixture was transformed into competent DH5α cells (Bethesda Research Labs). Eight clones were picked, grown up overnight, and analyzed for the presence of MDR inserts as follows.

One ml of an overnight of each of the eight clones was centrifuged in a microfuge, supernatants removed, and the bacterial pellets cracked using a cracking buffer consisting of 200 λ phenol, 170 λ TE buffer, and 30 λ 6×loading buffer. The samples were vortexed, centrifuged for 5 minutes, and the supernatants electrophoresed on a 0.8% agarose gel in TAE buffer at 50 volts for 16 hours. The slowest migrating clones were chosen for further analysis, and one of the clones, clone 5 was selected for further analysis by miniprep restriction digestion, and based on the results of the restriction analysis, was shown to carry the plasmid pLNL6-MDR.

Production of Amphotropic MDR1 Virus

Using the pLMDRL6 vector, amphotropic virions containing the MDR sequence were produced as follows. About 4×10$^5$ PSI-2 cells were plated in 100 mm tissue culture dishes and 16 hours subsequently, 3 hours before transfection of the vector pLMDRL6 into PSI-2 cells, the PSI-2 cells were refed fresh media, and the cells transfected via calcium phosphate mediated gene transfer.

PA317 cells were infected with media containing virions harvested from PSI-2 cells as follows. 5×10$^5$ PA317 cells were seeded per 60 mm tissue culture plate, and the cells allowed to grow overnight. The media from transfected PSI-2 cells was removed, and the cells refed 4 ml of fresh media. The PSI-2 cells were allowed to secrete virions into the media overnight, after which the media was harvested, and spun at 8,000 rpm for 5 minutes. The supernatant was used to infect the PA317 cells. Infection consisted of removing the cell culture media from the PA317 cells, and incubating them with 2 ml of the PSI-2 supernatant in the presence of 4 μg/ml polybrene. Twenty four hours later, the PA317 cells were subcultured and seeded at 3–4×10$^4$ cells/ 100 mm tissue culture plate. These cells were then selected for multiple drug resistance 48 hours after subculture by exposure to 20 ng/ml of vinblastine. 7 to 10 days later, colonies were apparent. None were apparent in the untransfected controls. Individual colonies were picked and found to be resistant to 20 ng/ml of vinblastine in continuous passage. Supernatants derived from such colonies were found, upon infection of normally drug sensitive cells, to confer drug resistance with a titer of 1×10$^5$ cfu/ml.

pLTNFL6

The TNF coding sequence used to produce pLTNFL6 was obtained from plasmid B11 described in U.S. Pat. No. 4,677,063. The TNF sequence is present on a Pst I fragment, and thus was removed by Pst I digestion and inserted into the Pst I site of the commercially available vector pGEM-3 (Promega), to produce pGEMTNF14.

Preparation of pLTNFL6

The vector pLTNFL6 was produced in several steps. Firstly, the MDR sequence in the vector pLMDRL6, described above, was excised, as was the sequence from the vector pGEMTNF14 that encodes TNF. The vector fragment lacking the MDR sequence and the TNF sequence were blunt ended and ligated to produce pLTNFL6.

In more detail, what this entailed was excising the MDR sequence by digesting 50 μg of pLNL-MDR in TA buffer with 200 units BamHI, (New England Bio Labs), 200 units Hind III New England Bio Labs), and 90 units Cla-I in a final volume of 500 λ for 2 hours at 37° C. Following this incubation period, the vector fragment lacking the MDR coding sequence was blunt ended by adding 10 λ of 10 mM dNTP (DATP, dCTP, dGTP, and dTTP), and 63 units of T4 DNA polymerase (Promega) and the mixture incubated for an additional 20 minutes at 37° C., followed by further incubation for 10 minutes at 68° C. Next, the reaction digest was phenol extracted, ethanol precipitated, and electrophoresed on a 1% agarose gel, using essentially the procedures described previously. The 4.7 kb blunt ended fragment was excised from the gel and isolated using standard glass bead purification procedures.

Similarly, 50 μg of pGEM TNF14 was digested in TA buffer with 200 units of Pst I in a final volume of 500 λ for 2 hours at 37° C. The reaction digest was treated as described above, and fractionated on a 1% agarose gel. A 1.1 kb encoding fragment that carries the TNF encoding sequence was excised from the gel and isolated as described above using glass beads. This fragment was blunt ended as follows. One μg of the fragment was incubated in 30 λ of TA buffer containing 0.05 mM dNTP's and 0.15 units T4 DNA polymerase. The mixture was incubated for 20 minutes at 37° C., and subsequently for an additional 10 minutes at 68° C. The blunt ended fragment was purified using glass beads, and resuspended in water in preparation for ligation to the blunt ended 4.7 kb vector fragment.

The ligation reaction was conducted as follows. 0.8 μg of the 1.1 kb blunt ended TNF fragment was combined with 1.0 μg of blunt ended 4.7 kb vector fragment in a total volume of 25 λ of TA buffer. The buffer contained 4 mM ATP and 400 units T4 DNA ligase (NEB). Ligation was conducted for 16 hours at 4° C., after which the ligation mixture was diluted 1:4 with TE buffer, and then 5 λ of the mixture was transformed into 100 λ of competent DH5α cells. Next, various dilutions of the transformed cell mixture were plated onto nitrocellulose filters, and incubated on culture plates containing 50 μg/ml of ampicillin. After 16 hours at 37° C., the plates were replica plated using a second set of nitrocellulose filters. The new nitrocellulose filters served as master plates. The original filters were processed in order to fix the bacterial DNA to the filters using standard alkaline lysis procedures. Subsequently, colonies containing TNF were identified using an end labelled oligonucleotide probe having the sequence:

5'-TCA GCT CCA GCC CAT TGG-3'

Hybridization consisted of preincubating the filters in 5×SSC., 4×Denhardts, 50 mM NaPO4, pH 6.8, 0.1% sodium dodecyl sulfate, and 100 μg/ml salmon sperm DNA. The filters were pre-incubated for 1 hour, followed by 1 hour incubation in 15 ml of the same solution containing kinased probe. Twenty picomoles of the probe was used, and the reaction was conducted at a Tm of 55° C. with shaking at about 120 revolutions per minute. Following the incubation period, the filters were washed with decreasing concentrations of SSC. solution as follows. The first wash consisted of 6×SSC. containing 0.1% SDS, the second wash 4×SSC. solution containing 0.1% SDS, and the third wash containing 2×SSC. containing 0.1% SDS. The first and second wash was repeated twice with the wash period being 15 minutes. The third wash was conducted one time also for a 15 minute wash period. All of the washes were conducted at 60° C. with 120 revolutions per minute agitation. Following washing, the filters were air dried, and autoradiographed at −70° C. Based on the autoradiographic results, 8 clones were picked from the master plates and inoculated into 3.5 ml of R2 media supplemented with 200 μg/ml of ampicillin. The bacteria were grown up under standard conditions and plasmid DNA isolated and restricted with Eco RI to identify those that have the TNF fragment inserted in the proper orientation. Eco RI digestion was carried out in 31.5 λ of 10×buffer (0.33M Tris-acetate, pH 7.9; 0.66M potassium acetate; 0.10M magnesium acetate; 5 mM dithiothreitol) , 2.5 λ of RNase (10 mg/ml), 265 λ of glass distilled water, and 13 λ of Eco RI (20 units/λ, New England Biolabs). Controls were run wherein the reaction mixture lacked Eco RI. The reaction was started by combining 1 λ of the appropriate clone with 34 λ of the reaction cocktail and subsequent incubation at 37° C. for 1 hour. The reaction digests were run on 1% TEAE gels. Three of the clones, TNF3, TNF6, and TNF7 exhibited the expected fragments having the following number of base pairs 3180, 1613, and 900. Thus, based on these results, which corresponds to the expected orientation for the TNF coding sequence, TNF3, which corresponds to the vector pLTNFL6, was selected for further study. TNF3 was expanded, and a large scale plasmid preparation made and analyzed by restriction digestion using Eco RI to confirm the orientation of the TNF coding sequences.

Transfection of PA317 cells with pLTNFL6

Transfection of PA317 cells was achieved by seeding $3 \times 10^5$ cells per 100 mm tissue culture dish containing 10 ml of media. The cells were allowed to grow for 24 hours, and then transfected by removing the media and adding the following solution: 10 μg of pLTNFL6, 1 μg of a β-actin-neomycin vector 10 μg of sheared LTK- carrier DNA, and 500 λ of 2×HBS (10 mM KCl, 11 mM D-glucose, 1.4 mM Na2HPO4, 42 mMHepes, and 171 mM, NaCl, pH 7.05). Water was added to make a final volume of 950 λ. Next, 50 λ of 2.5M CaCl2 was added, and the two immediately vortexed for 15 seconds. After a precipitate had formed the tube was incubated for 30 minutes at room temperature. The entire solution was then added to a 100 mm tissue culture dish containing PA317 cells, and the dish incubated overnight at 37° C. Subsequently, the media was changed with fresh media, incubated for another 24 hours at 37° C. and the cells trypsinized and plated at serial 1:4 dilutions into medium supplemented with 400 μg/ml of G418. The media was changed every 3 to 4 days, and 15 days after the transfection, clones were isolated using cloning cylinders, and the resulting clones grown up in mass culture and assayed for TNF expression as described in U.S. Pat. No. 4,677,063, or essentially as described above, using the L929 assay. Of 10 clones tested, 5 exhibited between about 13 and slightly more than 70 units of TNF/ml after 2 days of growing the transfected PA317 cells.

To show that PA317 pLTNFL6 transfected cells could produce infectious virions, transfected cells were seeded at a density of $3 \times 10^5$ cells/100 ml dish in Dulbecco's Modified Eagles Media supplemented with 10% fetal calf serum and incubated for 16 hours. Subsequently, virus was harvested by removing the media and subjecting it to centrifugation at 3,000×g for 5 minutes to remove any cellular debris, as well as intact cells. The resulting media supernatant containing virions was used to infect recipient cell cultures.

Various cell types were infected and included NIH 3T3 cells, human tumor infiltrating lymphocytes (TIL cells), or human melanoma cells. NIH 3T3 cells are well known to those skilled in the art and readily accessible. Human TIL and melanoma cells were obtained as described by Rosenberg, S. A. et al., 1986, Science, 233:1318; Topalian, S. et al., 1988, J. Clin. Oncol., 6:839; Belldegrun, A et al., 1988, Cancer Res., 48:206; or Rosenberg, S. et al., 1988, New Eng. J. Med. Infection of the recipient cultures consisted of removing the cell culture media and replacing it with virion containing supernatant culture media which was supplemented with 4 μg/ml of polybrene to facilitate infection. Sixteen hours later, fresh media was added to the cultures, and the cultures metabolically labelled to permit determination of TNF by immunoprecipitation.

Metabolic labelling of the cells, as well as control cell lines known to produce TNF, consisted of rinsing the cultures twice in phosphate buffered saline without calcium or magnesium for the following cell types: TNF6–8, NIH 3T3, and PA317 and incubating the cells in cysteine-minus minimal essential media at 37° C. Melanoma cells were incubated in Roswell Park Memorial Institute cysteine-minus media. Regardless of the type of media used, it was supplemented with 5% dialyzed fetal calf serum. The cells were then labelled with [35S] cysteine via aspirating off the media from the cell culture dishes, and replacing it with media containing 100–300 μCi/ml of [35S] cysteine for 3 hours at 37° C. Two ml of the radioactive media was used per 100 mm dish. Cultures were agitated during the labelling period after which the media was aspirated and the cells lysed in 1 ml of lysis buffer consisting of 20 mM Tris, pH 8.0, 200 mM LiCl, 1 mM EDTA, and 0.5% NP-40. Following the addition of the lysis buffer, the cell culture dishes were incubated for 5 minutes at 4° C., and the lysate immunoprecipitated to determine the presence of TNF.

Immunoprecipitation consisted of precipitating TNF present in the lysates using rabbit anti-TNF sera which was raised against human recombinant TNF. Before the lysates were reacted with TNF antibody, they were preabsorbed with 30 λ of a 50% suspension of protein A Sepharose CL-4B beads for 1 hour at 4° C. with continual agitation. The tubes were centrifuged to pellet the beads, and the supernatants transferred to new tubes to which was added 3.75 λ of rabbit anti-TNF sera. The tubes were incubated for 1 hour at 4° C. with agitation, and centrifuged for 15 seconds at 14,000 rpm. The supernatants were removed and pipetted into new tubes after which 30 λ of protein A sepharose CL-4B beads was added to the supernatants, followed by incubating the mixtures for 1 hour at 4° C. with agitation. Next, the beads were pelleted and washed 3 times with lysis buffer, and 2 times with buffer B (20 mM Tris pH 8.0, 100 mM NaCl, 0.5% NP40). Washing consisted of pelleting the beads for 8 seconds at 7,000 rpm, discarding the supernatant, and adding 1 ml of the appropriate wash solution. Finally, after the last wash, the material bound to the beads was subjected to electrophoresis by adding 30 λ of gel electrophoresis loading buffer consisting of 4% SDS, 15% glycerol, 6.25 mM Tris pH 6.8, 0.1% bromophenol blue, and 1 mM DTT. Immediately after adding the electrophoresis buffer, the samples were boiled for 5 minutes and subjected to electrophoresis on a 12% polyacrylamide gel. FIGS. 7 and 8 show the results. FIG. 7 shows immunoprecipitation analysis of cells transfected or infected with either the LTNFL6 plasmid or the high titer TNF retrovirus derived from LTNFL6. Lane A, PA317 cells transfected with the high titer retrovirus encoding both 26 kD and 17 kD TNF, LTNFL6; lane B, NIH 3T3 cells uninfected; and lane C, NIH 3T3 cells infected with the high titer TNF retrovirus, LTNFL6 clone 8 present in the cell culture supernatant of LTNFL6 transfected PA317 cells.

FIG. 8 shows immunoprecipitation analysis of 35S-cysteine labelled human melanoma cells infected with the TNF retrovirus LTNFL6. Lane A, PA317 cells transfected with LTNFL6; lanes B and C, uninfected and infected, respectively, NIH 3T3 cells with pLTNFL6 virus; and lanes D and E show uninfected and infected, respectively, human melanoma cells with the pLTNFL6 virus.

Confirmation of the integration of TNF encoding DNA sequences in human TILs was obtained by polymerase chain reaction amplification of a 500 base pair segment present in human TILs infected with pLTNFL6.

The reaction was conducted using standard PCR techniques and the following oligonucleotide primers:

CP484:  5'-TNF primer
    5'-GCT GGA GAA GGG TGA CCG AC-3'

CP487:  3'-MoMLV primer
    5'-CTA TAG GCT TCA GCT GGT GA-3'

FIG. 9 shows the results. Lane A presents uninfected TILs, while lanes B and C show infected TILs. Lane D is a positive control and presents PA317 cells transfected with pLTNFL6. The amplification of 500 base pair TNF sequence establishes that the TILs cells have been infected with the TNF retrovirus.

Additionally, immunoprecipitation experiments performed essentially as described above showed that the TIL cells were secreting TNF.

pLIL-2L6

The vector pLIL-2L6 was generated using essentially the same materials and methods described above that were employed to generate pLNL-MDR or pLNL-TNF with the following exceptions.

Firstly, the sequence that encodes IL-2 is present on a Pst I fragment that is described in detail in U.S. Pat. No. 4,518,584, inventor Mark et al.

Secondly, the oligonucleotide used to probe transformed bacteria containing the IL-2 sequence has the following sequence:

KD 12: 5'-GAGTTGCATCCTGTACATTGTGGCAGGAGT-3'

The hybridization conditions were essentially those described that were used to identify clones containing MDR or TNF sequences, except that the Tm was 69° C. Screening for IL-2 clones revealed the presence of 8 colonies by autoradiography that when restricted with Eco RI and Stu I in a double digestion revealed clones that had the proper orientation of the IL-2 encoding sequence. Eco RI and Stu I digestion was carried out in a solution consisting of 31.5 λ of 10×TA, 2.5 λ of RNase A (10 mg/ml), 252 λ of glass distilled water, 13 λ of Eco RI (20 units/λ), and 13 λ of Stu I (8 units/λ).

Example 6

Applications of pLMDRL6

The effectiveness of chemotherapeutic treatment of cancer is partly limited by the dose that can be administered to a patient without untoward side effects. These side effects include the elimination of normal lymphoid cells necessary for the immune responsiveness of the patient. Thus, an important application of the retrovirus, pLMDRL6, is its capacity to confer drug resistance on normal lymphoid cells, thereby permitting greater doses of a particular chemotherapeutic to be administered.

The procedures and advantages of conferring drug resistance on lymphoid cells can be demonstrated by infecting tumor infiltrating lymphocytes, or TILs, with pLMDRL6 in vitro, and returning these cells to an immunologically receptive host animal experiencing a chemotherapeutically sensitive tumor load. The procedures for obtaining TILs, as well as the procedures for infecting TILs with MDR amphotropic virus are presented above. When the infected TIL cells are returned to the animal an effective number of the cells adhere to, or infiltrate the tumor mass. Subsequently, the animal is administered one or more chemotherapeutics that are effective in treating the tumor load. Because the transfected TIL cells are resistant to concentrations of chemotherapeutics that are toxic to the tumor, the physician may gradually increase the dose of chemotherapeutics that are effective against the tumor beyond the dose that could be given without killing the TIL cells. In this way, a patients natural anti-tumor defenses are spared, and, indeed, augmented by exposing the tumor to elevated doses of chemotherapeutics.

Example 7

Two Gene Retroviral DNA Constructs

Retroviruses capable of expressing both the neomycin gene and TNF were constructed. The construction strategy for producing the two gene retroviral vectors is shown in FIG. 10. The vectors pLNSX, pLXSN and pLNCX all carry the neomycin gene sequences. Further, these vectors are described by Miller and Rosman, 1989, *Biotechniques*, 7(9):980.

The TNF construct contained the nucleotide sequence that encodes the γ-interferon signal peptide that is present in the vector pUC.FVXM Δ HIII TNF γ sig. The procedure consisted of digesting 150 μg of pGEMTNF14 and 150 μg of pUC.FVXM Δ HIII TNF γ sig with 600 units Pst I (New England Biolabs). The digestion was carried out in 1500 μl of restriction enzyme buffer consisting of 33 mM Tris-acetate, pH 7.9, 66 mM potassium acetate, 10 mM magnesium acetate, 0.5 mM dithiothreitol, at 37° C. for 60 minutes. The digests were phenol extracted, ethanol precipitated, and fractionated on a 1% Agarose gel in Tris-acetate electrophoresis buffer (40 mM tris, 1 mM EDTA, 5 mM sodium acetate, pH 7.5). The 1070 bp wild-type TNF fragment and the 902 TNF γ sig fragments, respectively, were isolated by glass beads.

Each Pst I fragment was made blunt by treatment with T4 DNA polymerase Four μg of each fragment was treated with 6.3 units of T4 DNA polymerase (New England Biolabs) in a volume of 125 μl consisting 33 mM Tris-acetate, pH 7.9, 66 mM potassium acetate, 10 mM magnesium acetate, 0.5 mM dithiothreitol and 0.10 mM each of dATP, dCTP, dTTP, and dGTP, at 37° C., for 10 minutes, then at 68° C., for 5 minutes. Each blunt-end fragment was purified by glass bead isolation.

Four μg of each vector was digested with an appropriate enzyme that generated blunt ends, in a volume of 100 μl (33 mM Tris-acetate, pH 7.9, 66 mM potassium acetate, 10 mM magnesium acetate, 0.5 mM dithiothreitol) as follows: pLNCX with 10 units Hpa I (NEB), pLNSX with 16 units STU I (NEB), pLXSN with 10 units HpaI (NEB), 37° C., 60 minutes.

Each digested vector was ligated to each blunt-ended TNF fragments in a 25 μl ligation mixture that contained 16 μg/ml of vector and 16 μg/ml of TNF fragment, 33 mM Tris-acetate, pH 7.9, 66 mM potassium acetate, 10 mM magnesium acetate, 0.5 mM dithiothreitol, 4 mM ATP, 16,000 units/ml, T4 DNA ligase (NEB). Ligations were incubated at 16° C., for 16 hours. Ligated DNA was transformed into competent DH5α cells (Bethesda Research Labs) following manufacturer's instructions. Resultant colonies were screened by standard methods using TNF oligonucleotide primer CP365 (5'-TCAGCTCCACGCCATTGG- 3') as a probe. Orientation was confirmed by restriction endonuclease analyses.

One of the plasmids carrying the TNF gene, pLTNFSN, was transfected into PA317 cells, and transfected clones isolated. Virus was rescued from one of the clones denoted LTNFSN-22. It was characterized, using standard techniques, as having a titer of $1.6 \times 10^6$ neo$^r$ cfu/ml and produced 62 units of TNF/ml.

Two gene viruses that encodes both neomycin resistance and IL-2 were constructed using the above described vectors, pLNSX, pLXSN and pLNCX. The procedures were similar with the following exceptions: a Pst I fragment that encodes IL-2 was blunt ended and inserted into the vectors. The L-2 fragment is described in U.S. Pat. No. 4,518,584, inventor Mark et al. IL-2 colonies were screened using the oligonucleotide KD12.

One of the plasmids carrying the L-2 gene pLIL2SN was transfected into PA317 cells, and transfected clones isolated. Virus was rescued from two clones and denoted pLIL2SN-16, and pLIL2SN-20. They exhibited the following titers, respectively, $2.0 \times 10^5$ and $2.2 \times 10^5$ neo$^r$ cfu/rnl and each produced about 8 units/ml of IL-2.

Finally, a two gene construct was made using the TNF mutein, TNF Δ (1→12). Briefly, the Pst I fragment from pFVXM Δ HIII TNF Δ12 was made blunt ended and cloned into the Hpa I site of pLXSN to generate pLTNFΔ12SN.

Example 8

Synergistic Effect of TNF and Neomycin

A surprising property of cells infected with virions that encode TNF and neomycin resistance is their increased sensitivity to selection with the antibiotic G418, if G418 is added immediately after infection. This is shown by infecting cells with the virion pLTNFSN-22 and subjecting the cells to immediate selection in G418. A suitable target cell for infection is PA317, and a suitable concentration of G418 is 400 ug/ml.

Using these conditions, about 60 per cent of the cells that carry pLTNFSN-22 are killed in the presence of G418 at the end of 24 hours in the selection media. In contrast, less than 10 per cent of cells infected with the same virus, but lacking the TNF sequences are killed.

Without intending to be held to any particular theory, it is thought that the sensitivity of cells expressing TNF in the presence of G418 selection occurs because the infected cells have insufficient time to express the neomycin resistant phenotype. This, in turn, permits G418 to inhibit the synthesis of a protein that normally renders the cells resistant to TNF killing. Thus, in the presence of G418 the cells are killed by TNF.

Support for this hypothesis is borne out if G418 selection is not applied to cells infected with pLTNFSN-22 until about 48 hours after infection, little cell death occurs during the subsequent 24 hours.

It will be appreciated by those skilled in the art that if cells that harbor TNF virions are to be successfully isolated using G418, or other similar antibiotic selection, that there must be sufficient expression time for the neomycin gene to confer G418 resistance on the infected cells.

Example 9

Cytotoxic Properties of TNF Muteins

The following TNF deletion muteins of TNF, produced using the oligonucleotides described above, were tested for cytotoxic activity: TNF Δ (1→12), TNF Δ (1+12), and TNF Δ (1+13), that is, deletion of the first 12 amino acids, of amino acids 1 and 12, and of amino acids 1 and 13, respectively. NIH 3T3 cells were co-transfected with β-actin-neo and with one the the series of pUC.FVXM Δ HIII TNF plasmids and then selected in 400 μg/ml G418. Cytotoxic activity was measured by seeding onto 100 ml tissue culture dishes serial dilutions of the G418 resistant heterogeneous populations. After about 20–50 colonies of cells were apparent, the media was aspirated off, and the colonies were overlaid with about $4 \times 10^6$ L929 cells in Dulbecco's Modified Eagles Medium supplemented with 10% fetal calf serum. Thirty minutes after plating the cells, the media was aspirated, and the cells overlaid with a solution consisting of 10 ml Dulbecco's Modified Eagles Medium, 0.9% Noble agar (Difco), and 10% fetal calf serum. This composition was kept molten at 45° C. prior to overlay, cooled and overlaid onto the cells. Next, the agar was hardened at room temperature for 30 minutes, and the plates incubated at 37° C. for 48 hours, after which the agar was removed, 10 ml phosphate buffered saline added, followed by 1 ml of a solution containing 12% glutaraldehyde, 1% methylene blue. The latter solution fixes and stains the cells which permits cell colonies and killing zones to be readily visualized. Finally, the plates were incubated at room temperature for 60 minutes, and rinsed in water and air dried.

Cytotoxic activity was scored as killing zones surrounding the transfected colonies. Two types of killing zones were observed; diffuse and non-diffuse zones. Non-diffuse killing indicates that the TNF mutein remains membrane bound and does not diffuse away from the transfected colonies to cause L929 death. In contrast, diffuse killing indicates that the TNF mutein is capable of diffusing away from the cell and causing killing over a wide area Table I summarizes the results. In addition to the muteins that were tested for cytotoxic activity, a vector control, wild-type TNF, and TNF γ sig were also tested for comparative purposes. It is apparent from the table that only the vector control, and TNF Δ (1+13) do not exhibit cytotoxicity by the L929 overlay assay. Further, wild-type TNF and the TNF γ sig have cytotoxic activity, but the activity exhibited a diffuse pattern about the transfected colonies thus showing that wild-type TNF and TNF γ sig are secreted from the transfected colonies. In contrast, TNF Δ (1→12), and TNF Δ (1+12) exhibit a non-diffuse killing pattern. This shows that these molecules exert their killing by being cell surface bound and coming into direct contact with L929 cells.

TABLE I

| Cell Population | TNF Bioassay on Population Supernatants | Bioassay by L929 Overlay |
| --- | --- | --- |
| Vector Control | <5 | – |
| TNF W.T. | 134 | + |
| TNFΔ(1 → 12) | <5 | +[b] |
| TNFΔ(1 + 12) | <5 | +[b] |
| TNFΔ(1 + 13) | <5 | – |
| TNF γnsig | 3125 | + |

Notes:
a. Positive results scored as diffuse killing zones surrounding target colonies.
b. No diffuse killing zones about colonies, but L929 cell killing observed directly on cell colonies (cell to cell contact).

A second experiment was done to assess the cytotoxic activities of the instant muteins, and particularly to confirm the cell surface location of TNF Δ (1→12) and TNF Δ (1+12). The experiment consisted of two parts. First, cells harboring the various TNF muteins were cell surface radio-iodinated using techniques well known in the art. The results revealed that, surprisingly, both muteins are bound to the cell surface. Secondly, transfected cells expressing each of the TNF muteins were grown in culture media, and labelled with $^{35}$S-cysteine after which the media was harvested and immunoprecipitated with anti-TNF polyclonal antibodies. Such antibodies and immunoprecipitation methods are known in the art. The inmmunoprecipitates were run on 12% polyacrylamide/SDS gels, and it was observed that for cells transfected with TNF Δ (1+12) and TNF Δ (1+13) there was a molecule about 17 kD that was immunoprecipitated. Nothing was detected in the TNF Δ (1→12) derived media.

The above results, when considered together, establish the following: TNF Δ (1→12), is membrane bound and not secreted into the cell culture media, and the membrane bound form is cytotoxic. TNF Δ (1+12) is also membrane bound and the membrane bound form is cytotoxic. Surprising, there is also secreted by the transfected cells a molecule about 17 kD. Finally, TNF Δ (1+13) appears to be membrane bound, but the membrane bound form is not cytotoxic. This construct also yields a secreted molecule of about 17 kD.

An experiment was conducted to determine if the soluble molecules having molecular weights about 17 kD secreted by cells transfected with TNF Δ (1+12) and TNF Δ (1+13) have cytotoxic activity. This experiment was done by growing the appropriately transformed 3T3 cells, and separating the cells and media containing the secreted molecules. The media was assayed in L929 cells as previously described, and shown not to have cytotoxic activity. Thus, the secreted 17 kD molecules are, unlike wild-type 17 kD TNF, not cytotoxic.

FIG. 12 shows a restriction map of the cDNA sequence that encodes 26 kD TNF and the regions of the molecule that were deleted to produce the various muteins.

Example 10

Therapeutic Applications for Two Gene Retrovirions that Encode Neomycin Resistance and IL-2 or TNF The virion pLIL2SN-16, described above, is utilized in tumor therapy by infecting isolated human TIL cells using standard techniques. The procedures are described by Rosenberg, S. A. et al., 1986, *Science*, 233:1318; Topalian, S. et al., 1988, *J. Clin. Oncol.*, 6:839; Belldegrun, A et al., 1988, *Cancer Res.*, 48:206; or Rosenberg, S. et al., 1988, *New Eng. J. Med.* Infection of the recipient cultures consists of removing the cell culture media and replacing it with virion containing supernatant culture media which is supplemented with 4 μg/ml of polybrene to facilitate infection.

The TIL cells are washed to remove debris, polybrene, etc., and in other ways made suitable for infusion into a cancer patient. The dose of infected TIL cells may vary, with the optimal dose being empirically determinable by the attending physician. It is anticipated that more than one infusion of infected TIL cells will be desirable for satisfactory treatment. Following the initial treatment and thereafter, the patients tumor mass is monitored and significant shrinkage would be apparent at the end of 4 weeks.

Using essentially the same procedures, TIL cells may be infected with retrovirions that encode the TNF mutein TNF Δ (1→12) using retrovirions generated by transfection of pLTNFΔ12SN into an appropriate host cell, and isolating virions secreted into the cell culture media.

The following materials have been deposited at the American Type Culture Collection, Rockville, Md., USA (ATCC) under the terms of the Budapest Treaty on the International Recognition of the Deposit of Microorganisms for the Purposes of Patent Procedure and Regulations thereunder (Budapest Treaty) and are thus maintained and made available according to the terms of the Budapest Treaty. Availability of such stains is not to be construed as a license to practice the invention in contravention of the rights granted under the authority of any government in accordance with its patent laws.

The following materials have been deposited with the ATCC. and have been assigned the indicated ATCC. deposit numbers. They have also been deposited with the Master Culture Collection (CMCC) of Cetus Corporation, Emeryville, Calif., USA, the assignee of the present application, and assigned the indicated CMCC deposit numbers:

| Plasmids | CTCC Deposit No. | CMCC Deposit No. | ATCC Deposit No. | Date of ATCC Deposit |
|---|---|---|---|---|
| pB11(pE4) | | 2138 | 39894 | 15 October 1984 |
| pAW711 | | 2162 | 39918 | 8 November 1984 |
| pFVXM | | 2701 | 67103 | 23 April 1986 |
| pLTNFL6 | | 3684 | 68118 | 12 October 1989 |
| pLIL-2L6 | | 3685 | 68119 | 13 October 1989 |
| pLMDRL6 | | 3687 | 68120 | 13 October 1989 |
| p U.C. FVXM ΔHIII TNF γ sig | | 3688 | 68121 | 13October1989 |
| pLTNFSN | | 3759 | | |
| pLTNF γ sig SN | | 3758 | | |
| pLNSTNF γ sig | | 3756 | | |
| pLNSTNF | | 3757 | | |
| pLNCTNF γ sig | | 3760 | | |
| PLNCTNF | | 3761 | | |
| pLIL2SN | | | | |
| Packaging Cell Line | | | | |
| PA317 | | | CRL9078 | |
| Transfected NIH 3T3 Cells Lines* | | | | |
| TNFΔ(1 + 13) [TNFAY] | 10729 | | | |
| TNT γ sig | 10726 | | CRL10333 | |
| TNF6[wild-type TNF] | 10730 | | | |
| TNFΔ(1 + 12)[TNFA12] | 10728 | | CRL10334 | |
| TNFΔ(1 + 12) [TNFAW] | 10727 | | | |

*Cells were transfected with pUCFVXM Δ HIII containing the appropriate TNF construct.

The foregoing written specification is considered to be sufficient to enable one skilled in the art to practice the invention. The deposit of materials herein does not constitute an admission that the written description herein contained is inadequate to enable the practice of any aspect of the invention, including the best mode thereof, nor is this deposit to be construed as limiting the scope of the claims to the specific illustrations which materials deposited represent.

We claim:

1. A transformed TIL cell containing an exogenous gene encoding a recombinant human TNF that is expressible therein, said recombinant human TNF being a mutein of TNF prohormone selected from the group consisting of TNFΔ(1→12), TNFΔ(1+12), and TNF γ sig prohormone.

2. The TIL cell of claim 1, wherein said recombinant TNF is a deletion mutein of TNF prohormone selected from the group consisting of TNFΔ(1→12) and TNFΔ(1+12).

3. The TIL cell of claim 2, wherein said recombinant TNF is TNFΔ(1→12).

4. The TIL cell of claim 2, wherein said recombinant TNF is TNFΔ(1+12).

5. The TIL cell of claim 1, wherein said recombinant TNF is TNF γ sig.

6. A culture of transformed human TIL cells, said cells containing an expressible gene encoding a recombinant TNF said recombinant TNF being a mutein of TNF prohormone selected from the group consisting of TNF Δ(1→12), TNFΔ(1+12) and TNF γ sig prohormone.

7. The culture of claim 6, wherein said recombinant TNF is a deletion mutein of TNF prohormone selected from the group consisting of TNFΔ(1→12) and TNFΔ(1+12).

8. The culture of claim 7, wherein said recombinant TNF is TNFΔ(1→12).

9. The culture of claim 7, wherein said recombinant TNF is TNFΔ(1+12).

10. The culture of claim 6, wherein said recombinant TNF is TNF γ sig.

11. A pharmaceutical composition comprising:

a) a transformed human TIL cell containing an exogenous gene encoding a recombinant TNF, said recombinant TNF being a mutein of TNF prohormone selected from the group consisting of TNFΔ(1→12), TNFΔ(1+12) and TNF γ sig prohormone; and b) a pharmaceutical excipient.

12. The pharmaceutical composition of claim 11, wherein said recombinant TNF is TNFΔ(1→12).

13. The pharmaceutical composition of claim 11, wherein said recombinant TNF is TNFΔ(1+12).

14. The pharmaceutical composition of claim 11, wherein said recombinant TNF is TNF γ sig.

* * * * *